US007230002B2

(12) United States Patent
Thomas et al.

(10) Patent No.: US 7,230,002 B2
(45) Date of Patent: Jun. 12, 2007

(54) DIPEPTIDYL PEPTIDASE IV INHIBITORS; PROCESSES FOR THEIR PREPARATION AND COMPOSITIONS THEREOF

(75) Inventors: Abraham Thomas, Navi Mumbai (IN); Balasubramanian Gopalan, Mumbai (IN); V. S. Prasada Rao Lingam, Navi Mumbai (IN); Daisy Manish Shah, Mumbai (IN)

(73) Assignee: Glenmark Pharmaceuticals Ltd., Mumbai (IN)

( * ) Notice: Subject to any disclaimer, the term of this patent is extended or adjusted under 35 U.S.C. 154(b) by 29 days.

(21) Appl. No.: 11/050,663

(22) Filed: Feb. 2, 2005

(65) Prior Publication Data
US 2005/0192324 A1    Sep. 1, 2005

Related U.S. Application Data

(60) Provisional application No. 60/549,759, filed on Jul. 29, 2004, provisional application No. 60/590,603, filed on Jul. 23, 2004.

(30) Foreign Application Priority Data
Feb. 3, 2004  (IN)  .................. 112/2004
Jul. 29, 2004  (IN)  .................. 808/2004

(51) Int. Cl.
*C07D 239/42*  (2006.01)
*C07D 401/12*  (2006.01)
*A61K 31/4439*  (2006.01)
*A61K 31/506*  (2006.01)

(52) U.S. Cl. ................. 514/275; 514/343; 544/332; 546/279.1

(58) Field of Classification Search .............. None
See application file for complete search history.

(56) References Cited

U.S. PATENT DOCUMENTS

| 5,691,356 A | 11/1997 | Das et al. |
| 5,939,560 A | 8/1999 | Jenkins et al. |
| 6,011,155 A | 1/2000 | Villhauer |
| 6,172,081 B1 | 1/2001 | Damon |
| 6,380,398 B2 * | 4/2002 | Kanstrup et al. ........... 548/530 |
| 2004/0072892 A1 | 4/2004 | Fukushima et al. |
| 2004/0121964 A1 * | 6/2004 | Madar et al. ................. 514/19 |

FOREIGN PATENT DOCUMENTS

| EP | 1354882 | 10/2003 |
| EP | 1 464 335 A2 | 10/2004 |
| WO | WO-93/01167 | 1/1993 |
| WO | WO-93/17020 A2 | 9/1993 |
| WO | WO-94/24093 A1 | 10/1994 |
| WO | WO-97/40832 | 11/1997 |
| WO | WO98/19998 | 5/1998 |
| WO | WO-01/46199 A1 | 6/2001 |
| WO | WO-01/96295 | 12/2001 |
| WO | WO-01/96346 A1 | 12/2001 |
| WO | WO-03/013526 A1 | 2/2003 |
| WO | WO-03/037327 | 5/2003 |
| WO | WO-03/084940 | 10/2003 |
| WO | WO2004/016587 | 2/2004 |
| WO | WO-2004-087680 A1 | 10/2004 |
| WO | WO2005/023762 | 3/2005 |
| WO | WO-2005/033072 A2 | 4/2005 |

OTHER PUBLICATIONS

Madar et al., STN International, HCAPLUS Database, Columbus, OH, Accession No. 2004:1127082, Reg. No. 813433-88-4P (2007).*
Varljen et al., "Clinical Relevance of the Serum Dipeptidyl Peptidase IV (DPP IV/CD26) Activity in Adult Patients with Crohn's Disease and Ulcerative Colitis," Croatica Chemica Acta, 78(3), 427-432 (2005).*
Mitani et al., "Dipeptidyl Peptidase IV Inhibition: Improves Impaired Glucose Tolerance in High-Fat Diet-Fed Rats: Study Using a Fischer 344 Rat Substrain Deficient in Its Enzyme Activity," Jpn. J. Pharmacol., 88, 442-450 (2002).*
Ashworth, et al., *Bioorganic & Medicinal Chem. Ltrs.* vol. 6, No. 10 pp. 1163-1166, 1996; *2-Cyanopyrrolidides as Potent, Stable Inhibitors of Dipeptidyl Peptidase IV.*
Coutts et al., *J. Med. Chem.* 1996, 38, 2087-2094, *Structure-Activity Relationships of Boronic Acid Inhibitors of Dipeptidyl Peptidase IV. 1. Variation of the $P_2$ Position of $X_{88}$-boroPro Dipeptides.*
Hughes et al., *Biochemistry* 1999, 38, 11597-11603, (1-[[[2-[(5-Cyanopyridin-2-yl) amino]ethyl]amino]acetyl]-2-cyano(S)-pyrrolidine) , *a Slow-Binding Inhibitor of Dipeptidyly Peptidase IV.*
Villhauer et al., *J. Med. Chem.* 2003, 46 2774-2789, 1-[[(3-Hydrody-1-adamantyl) amino]acetyl]-2-cyano-(S)-pyrrolidine: *A Potent, Selective, and Orally Bioavailable Dipeptidyl Peptidase IV Inhibitor with Antihyperglycemic Properties.*
International Search Report for International Application No. PCT/US 03/29018 mailed Mar. 30, 2004.
Campbell, Jeffrey A., et al., "Chirospecific Syntheses of Precursors of Cyclopentane and Cyclopentane Carbocyclic Nucleosides by [3+3]-Coupling and Transannular Alkylation", J. Org. Chem., 1995, vol. 60, pp. 4602-4616.
Mekrami, Mounia, et al., "Enzymatic Asymmetric Synthesis of Cis-4-cyclopentene- 1,3-dimethanol monoacetate", Tetrahedron: Asymmetry, 1992, vol. 3, No. 3, pp. 431-436.
Fortt, Simon M., et al., "An Approach to a Carbocyclic Analogue of Cyclic Adenosine 5'-Diphosphate Ribose. The Synthesis and Biphosphorylation of $N^1$-[(1S,3R)-3-(Hydroxymethyl)cyclopent-1-yl]inosine.", Tetrahedron Letters, 1997, vol. 38, No. 30, pp. 5371-5374.
Grumann, Arne, et al., "The Synthesis of trans-Carbovir via the Ramberg-Backlund Reaction", Tetrahedron Letters, 1995, vol. 36, No. 42, pp. 7767-7768.

* cited by examiner

*Primary Examiner*—Kamal A. Saeed
*Assistant Examiner*—Andrew B. Freistein
(74) *Attorney, Agent, or Firm*—Darby & Darby

(57) ABSTRACT

The present invention relates to novel dipeptidyl peptidase IV (DPP-IV) inhibitors their analogs, isomers, pharmaceutical compositions, therapeutic uses and methods of making the same.

29 Claims, No Drawings

DIPEPTIDYL PEPTIDASE IV INHIBITORS; PROCESSES FOR THEIR PREPARATION AND COMPOSITIONS THEREOF

RELATED APPLICATIONS

This application claims priority to Indian Patent Application No. 112/MUM/2004, filed Feb. 03, 2004, Indian Patent Application No. 808/MUM/2004, filed Jul. 29, 2004, U.S. Provisional Application No. 60/549,759, filed Mar. 2, 2004, and U.S. Provisional Application No. 60/590,603, filed Jul. 23, 2004 each of which are incorporated herein by reference in their entirety.

FIELD OF THE INVENTION

The present invention relates to novel organic compounds, their analogs, tautomers, regioisomers, stereoisomers, enantiomers, diastereomers, polymorphs, pharmaceutically acceptable salts, N-oxides, and pharmaceutically acceptable solvates thereof and pharmaceutical compositions containing them useful as dipeptidyl peptidase IV (DPP-IV) inhibitors. The present invention also relates to methods of preparing the cyclopentyl compounds and methods of treating diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases, AIDS, intestinal diseases, inflammatory bowel syndrome, anorexia nervosa, osteoporosis, hyperglycemia, syndrome X, diabetic complications, hyperinsulinemia, obesity, atherosclerosis and related diseases, as well as various immunomodulatory diseases and chronic inflammatory bowel disease (such as Crohn's disease and ulcerative colitis) by administering such compounds.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutic control of glucose homeostasis, lipid metabolism and hypertension are critically important in the clinical management and treatment of diabetes mellitus.

There are two generally recognized forms of diabetes. In Type I diabetes, or insulin-dependent diabetes mellitus (IDDM), patients produce little or no insulin, the hormone which regulates glucose utilization. In Type II diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type II diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of a sulfonylurea (e.g., tolbutamide and glipizide) or meglitinide, which stimulate the pancreatic β-cells to secrete more insulin, and/or by injection of insulin when a sulphonylurea or meglitinide becomes ineffective, can result in insulin concentration levels high enough to stimulate the very insulin-resistant tissues. However, dangerously low levels of plasma glucose can result from administration of insulin or insulin secretagogues (sulfonylureas or meglitinides), and an increased level of insulin resistance due to the even higher plasma insulin levels can occur. Biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type II diabetes.

The glitazones (i.e., 5-benzylthiazolidine-2,4-diones) are a more recently described class of compounds with potential for ameliorating many symptoms of Type II diabetes. These agents substantially increase insulin sensitivity in muscle, liver and adipose tissue in several animal models of Type II diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type II diabetes are agonists of the alpha, gamma or delta subtype, or a combination of these, and in many cases are chemically different from the glitazones (i.e., they are not thiazolidinediones). Serious side effects (e.g., liver toxicity) have occurred with some of the PPAR agonists, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly Type II diabetes. See for example WO 97/40832, WO 98/19998; U.S. Pat. No. 5,939,560; Bioorg. Med. Chem. Lett., 6(10), 1163–1166 (1996); and Bioorg. Med. Chem. Lett., 6(22), 2745–2748 (1996). The usefulness of DP-IV inhibitors in the treatment of Type II diabetes is based on the fact that DP-IV in vivo readily inactivates glucagon like peptide-1 (GLP-1) and gastric inhibitory peptide (GIP). GLP-1 and GIP are incretins and are produced when food is consumed. The incrertins stimulate production of insulin. Inhibition of DP-IV leads to decreased inactivation of the incretins, and this in turn results in increased effectiveness of the incretins in stimulating production of insulin by pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues. DP-IV inhibitors may also have other therapeutic utilities, as discussed herein. DP-IV inhibitors have not been studied extensively to date, and generally have been used for indicators other than diabetes. Improved DP-IV inhibitors for the treatment of diabetes and potentially other diseases and conditions are needed.

Various compounds shown below are DPP-IV inhibitors, have reached advanced stages of human clinical trials:

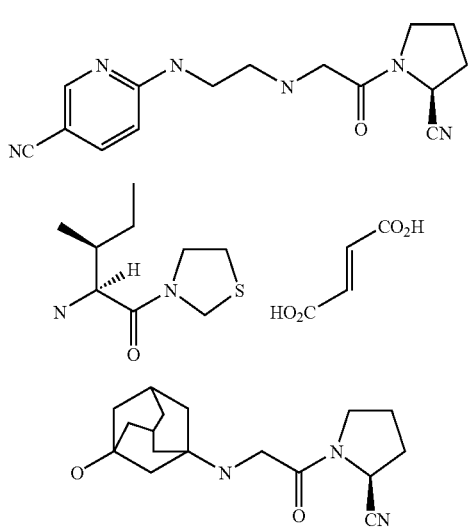

Novartis "NVP-DPP-728" which has the formula A, Probiodrug "P32/98 which has the formula B and Novartis "NVP-LAF-237" which has the formula C.

Although a number of DPP-IV inhibitors have been described in the literature, all have limitations relating to potency, stability or toxicity. It is clear that a great need exists for new DPP-IV inhibitors which are useful in treating conditions mediated by DPP-IV inhibition. During the course of our research aimed at the development of novel antidiabetic compounds having potential DPP-IV inhibitory activity, we have found in the literature a number of patents and publications as follows: PCT Patent publication WO 2003084940 A1 (published on, Oct. 16, 2003, Sankaranarayanan), JMC (2003), 46(13), 2774–2789 , Novartis Institute for Biomedical Research, NJ, USA, PCT Patent publication WO 03037327A1 (published on, Jul. 10, 2003, Hoffmann-La-Roche), EP-Patent publication EP 1354882 A1 (published on Oct. 22, 2003, Kyowa Hakko Kogyo Co., Ltd., Japan), PCT Patent publication WO 9819998 A2 (published on May 14, 2003 , Novartis A.-G., Switz.), U.S. Pat. No. 6,011,155 A, patent granted on Jan. 4, 2000 (Novartis A.-G., Switz).

SUMMARY OF THE INVENTION

The present invention relates to novel organic compounds, their analogs, tautomers, regioisomers, stereoisomers, enantiomers, diastereomers, polymorphs, pharmaceutically acceptable salts, N-oxides, pharmaceutically acceptable solvates and pharmaceutical compositions containing them. The present invention more particularly relates to novel dipeptidyl peptidase IV (DPP-IV) inhibitors of the formula (I), their analogs, tautomers, regioisomers, stereoisomers, enantiomers, diastereomers, polymorphs, pharmaceutically acceptable salts, N-oxides, pharmaceutically acceptable solvates and pharmaceutical compositions containing them.

The novel compounds are of general formula (I)

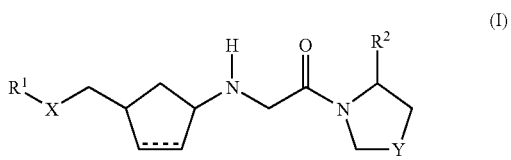

wherein:
  Y is —S (O) m, —CH$_2$—, CHF, or —CF$_2$;
  X is NR$^3$, O or S (O)$_m$;
  m is 0, 1 or 2;
  the dotted line [----] in the carbocyclic ring represents an optional double bond (i.e., a single or double bond);
  R$^1$ is substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl;
  R$^2$ is hydrogen, nitrile (—CN), COOH, or isosteres of carboxylic acids, including, but not limited to, SO$_3$H, CONOH, B(OH)$_2$, PO$_3$R$^4$R$^5$, SO$_2$N R$^4$R$^5$, tetrazole, amides, esters and acid anhydrides;
  R$^3$ is hydrogen, hydroxy, acetyl, substituted or unsubstituted alkyl, or substituted or unsubstituted alkoxy;
  R$^4$ and R$^5$ may be the same or different and are independently hydrogen, nitro, hydroxy, cyano, formyl, acetyl, halogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, substituted or unsubstituted carboxylic acid derivatives or analogs, tautomeric forms, regioisomers, stereoisomers, enantiomers, diastereomers, polymorphs, solvates, N-oxides, or pharmaceutically acceptable salts thereof.

According to one preferred embodiment is a compound according to formula I, wherein X is —NR$^3$—wherein R$^3$ is hydrogen.

Further preferred is a compound according to formula I, wherein X is O.

Further preferred is a compound according to formula I, wherein X is S(O)$_m$ and m is 0 or 2.

Further preferred is a compound according to formula I, wherein Y is $CH_2$.

Further preferred is a compound according to formula I, wherein Y is CHF.

Further preferred is a compound according to formula I, wherein Y is $S(O)_m$ and m is 0.

Further preferred is a compound according to formula I, wherein $R^1$ is phenyl.

Further preferred is a compound according to formula I, wherein $R^1$ is 4-cyano phenyl.

Further preferred is a compound according to formula I, wherein $R^1$ is 3-fluro-4-cyano phenyl.

Further preferred is a compound according to formula I, wherein $R^1$ is 2-fluro-4-nitro phenyl.

Further preferred is a compound according to formula I, wherein $R^1$ is 4-nitro phenyl.

Further preferred is a compound according to formula I, wherein $R^1$ is 4-fluro phenyl.

Further preferred is a compound according to formula I, wherein $R^1$ is 2-fluro-4-nitro phenyl.

Further preferred is a compound according to formula I, wherein $R^1$ is 2,4,5 trifluro phenyl.

Further preferred is a compound according to formula I, wherein $R^1$ is pyridin-2-yl.

Further preferred is a compound according to formula I, wherein $R^1$ is 5-cyano pyridin-2-yl.

Further preferred is a compound according to formula I, wherein $R^1$ is Pyrimidin-2-yl.

Further preferred is a compound according to formula I, wherein $R^1$ is benzimidazole-2-yl.

Further preferred is a compound according to formula I, wherein $R^1$ is 4-cyano dibenzofuran-1-yl.

Further preferred is a compound according to formula I, wherein $R^1$ is 1-phenyl-1,2,3,4-terazol-5-yl Further preferred is a compound according to formula I, wherein $R^2$ is Hydrogen.

Further preferred is a compound according to formula I, wherein $R^2$ is a cyano group.

The present invention also includes any combination of the aforementioned preferred X, Y, $R^1$ and $R^2$ groups.

Yet another preferred embodiment is a compound according to formula I, wherein $R^1$ is 5-cyanopyridin-2-yl, pyrimidin-2-yl, 2-fluoro-4-nitrophenyl, or 4-cyano-3-nitrophenyl; $R^2$ is a cyano group, X is —NH or O; Y is —$CH_2$, —CHF, or S; and the dotted line is a single bond. Accordingly, in one embodiment, X is —NH.

Intermediates useful for the preparation of compounds of formula I include compounds of general formula (II)

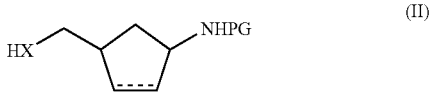

wherein:
X is $NR^3$, O or S $(O)_m$;
m is 0, 1 or 2;
$R^3$ is hydrogen, hydroxy, acetyl, substituted or unsubstituted alkyl, or substituted or unsubstituted alkoxy;
PG is a suitable amino protecting group including, but not limited to, tertiary butyloxy (Boc), fluorenenylmethyl (Fmoc), carbenzyloxy (Cbz) or analogs, tautomeric forms, regioisomers, stereoisomers, enantiomers, diastereomers and the salts thereof.

Other intermediates useful for the preparation of the compounds of formula I include compounds of general formula (III)

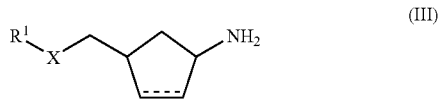

wherein:
X is $NR^3$, O or S $(O)_m$;
m is 0, 1 or 2;
the dotted line [- - - -] in the carbocyclic ring represents an optional double bond (i.e., a single or double bond);
$R^1$ is substituted or unsubstituted aryl, substituted or unsubstituted arylalkyl, substituted or unsubstituted heteroaryl, substituted or unsubstituted heterocyclic ring, substituted or unsubstituted heterocyclylalkyl, or substituted or unsubstituted heteroarylalkyl;
$R^3$ is hydrogen, hydroxy, acetyl, substituted or unsubstituted alkyl, substituted or unsubstituted alkoxy or analogs, tautomeric forms, regioisomers, stereoisomers, enantiomers, diastereomers and the salts thereof.

Compounds of the invention having a cyclopentane or a cyclopentene ring bearing 1,3-substituents can fall into a cis or trans geometry leading to mixture of compounds. Again, in principle, such substitution patterns with two chiral centers can result in up to two pairs of diastereomers. Therefore, the compounds of interest of the present invention may be prepared as a mixtures as well as single diastereomers. Mixtures as well as single diasteriomers of the above mentioned isomers are within the scope of this invention. The optically active 1-aminocyclopentane carboxylic acid compounds of the present invention may be obtained by resolution or by asymmetric synthesis.

Some of the representative compounds according to the present invention are specified below but should not construed to be limited thereto:

1. cis-(±)-6-(3-[2-(1-Pyrrolidinyl)-2-oxoethylamino]cyclopentylmethylamino)nicotinonitrile
2. 6-{(3-[2-Oxo-2-(1,3-thiazolan-3-yl)ethylamino] cyclopentylmethylamino}nicotino-nitrile
3. 6-((1SR,3RS)-3-{2-[(2S)-2-Cyanopyrrolidin-1-yl]-2-oxoethylamino}cyclopentyl-methylamino)nicotinonitrile
4. 6-((1SR,3RS)-3-{2-[(2S)-2-Cyanopyrrolidin-1-yl]-2-oxoethylamino}cyclopentyl-methylamino)nicotinonitrile dihydrochloride
5. 6-((1SR,3RS)-3-{2-[(2S)-2-Cyanopyrrolidin-1-yl]-2-oxoethylamino}cyclopentyl-methylamino)nicotinonitrile maleate
6. 6-((1SR,3RS)-3-{2-[(2S)-2-Cyanopyrrolidin-1-yl]-2-oxoethylamino}cyclopentyl-methylamino)nicotinonitrile fumarate
7. 6-((1SR,3RS)-3-{2-[(2S)-2-Cyanopyrrolidin-1-yl]-2-oxoethylamino}cyclopentyl-methylamino)nicotinonitrile citrate
8. 6-((1S,3R)-3-{2-[(2S)-2-Cyanopyrrolidin-1-yl]-2-oxoethyhmino}cyclopentyl methyl-amino)nicotinonitrile
9. 6-((1S,3R)-3-{2-[(2S)-2-Cyanopyrrolidin-1-yl]-2-oxoethylamino}cyclopentyl methyl-amino)nicotinonitrile dihydrochloride 10. 6-((1R,3S)-3-{2-[(2S)-2-Cyanopyrrolidin-1-yl]-2-oxoethylamino}cyclopentyl methyl-amino)nicotinonitrile
11. 6-((1R,3S)-3-{2-[(2S)-2-Cyanopyrrolidin-1-yl]-2-oxoethylamino}cyclopentyl methyl-amino)nicotinonitrile dihydrochloride
12. 6-((4SR,1RS)-4-{2-[(2S)-2-cyanopyrrolidin-1-yl]-2-oxoethylamino}-2-cyclopentenyl-methylamino)nicotinonitrile
13. 6-((1RS,3RS)-3-{2-[(2S)-2-Cyanopyrrolidin-1-yl]-2-oxoethylamino}cyclopentyl-methylamino)nicotinonitrile
14. 6-((1SR,3RS)-3-{2-[(2S,4S)-2-Cyano-4-fluoropyrrolidin-1-yl]-2-oxoethylamino}-cyclopentylmethylamino)nicotinonitrile
15. 6-((1S,3R)-3-{2-[(2S,4S)-2-Cyano-4-fluoropyrrolidin-1-yl]-2-oxoethylamino}cyclopentylmethylamino)nicotinonitrile
16. (4S)-3-{2-(1SR,3RS)-3-[(5-Cyano-2-pyridylaminomethyl)cyclopentyl amino]acetyl}-1,3-thiazolane-4-carbonitrile dihydrochloride
17. (4S)-3-{2-(1RS,3RS)-3-[(5-Cyano-2-pyridylaminomethyl)cyclopentylamino]acetyl}-1,3-thiazolane-4-carbonitrile dihydrochloride
18. (2S)-1-{2-[(3SR,1RS)-3-(2-Pyrimidinylaminomethyl)cyclopentylamino)acetyl}-pyrrolidine-2-carbonitrile
19. (2S)-1-{2-[(3SR,1RS)-3-(2-Pyrimidinylaminomethyl)cyclopentylamino)acetyl}-pyrrolidine-2-carbonitrile dihydrochloride
20. (2S)-1-{2-[(3S,1R)-3-(2-Pyrimidinylaminomethyl)cyclopentylamino)acetyl}-pyrrolidine-2-carbonitrile
21. (2S)-1-{2-[(3R,1S)-3-(2-Pyrimidinylaminomethyl)cyclopentylamino]acetyl}-pyrrolidine-2-carbonitrile
22. (2S)-1-{2-[(3S,1R)-3-(1-Phenyl-1H-1,2,3,4-tetrazol-5-ylaminomethyl)cyclopentyl-amino]acetyl}-pyrrolidine-2-carbonitrile
23. (2S)-1-{2-[(3SR,1RS)-3-(3-Chloro-4-nitroanilinomethyl)cyclopentylamino]acetyl}-pyrrolidine-2-carbonitrile
24. (2S)-1-{2-[(3SR,1RS)-3-(2-Fluoro-4-nitroanilinmethyl)cyclopentylamino]acetyl}-pyrrolidine-2-carbonitrile
25. (2S)-1-{2-[(1R,3S)-3-(2-Fluoro-4-nitroanilinmethyl)cyclopentylamino]acetyl}-pyrrolidine-2-carbonitrile
26. (2S,4S)-4-Fluoro-1-{2-[(1R,3S)-3-(2-fluoro-4-nitroanilinomethyl)cyclopentyl amino]-ethyl}-pyrrolidine-2-carbonitrile
27. (2S)-1-{2-[(3SR,1RS)-3-(2,4,5-Trifluoroanilinomethyl)cyclopentylamino]acetyl}-pyrrolidine-2-carbonitrile
28. (2S)-1-{2-[(3SR,1RS)-3-Phenylsulfanylmethylcycopentylamino]acetytl}-pyrrolidine-2-carbonitrile
29. (2S)-1-{2-[(3SR,1RS)-3-Phenylsulfonylmethylcyclopentylamino]acetytl}-pyrrolidine-2-carbonitrile
30. (2S)-1-{2-[(3S,1R)-3-Phenylsulfanylmethylcycopentylamino]acetytl}-pyrrolidine-2-carbonitrile
31. (2S)-1-{2-[(3S,1R)-3-Phenylsulfonylmethylcyclopentylamino]acetytl}-pyrrolidine-2-carbonitrile
32. (2S)-1-{2-[(1S,3R)-3-Phenylsulfanylmethylcyopentylamino]acetytl}-pyrrolidine-2-carbonitrile
33. (2S)-1-{2-[(1S,3R)-3-Phenylsulfonylmethylcyclopentylamino]acetytl}-pyrrolidine-2-carbonitrile
34. (2S)-1-{2-[(1S,3R)-3-(4-Fluorophenylsulfanylmethyl)cyclopentylamino]acetyl}-pyrrolidine-2-carbonitrile
35. (2S)-1-{2-[(4S,1R)-4-(2-Pyridylsulfanylmethyl)cyclopent-2-eneamino]acetyl}-pyrrolidine-2-carbonitrile
36. (2S)-1-{2-[(1S,3R)-3-(2-Pyridylsulfanylmethyl)cyclopentylamino]acetyl}-pyrrolidine-2-carbonitrile
37. (2S)-1-{2-[(1S,3R)-3-(2-Pyridylsulfonylmethyl)cyclopentylamino]acetyl}-pyrrolidine-2-carbonitrile
38. 6-((1SR,3RS)-3-{2-[(2S)-2-Cyanopyrrolidin-1-yl]-2-oxoethylamino}cyclopentyl-methylsulfanyl)nicotinonitrile
39. 6-((1SR,3RS)-3-{2-[(2S)-2-Cyanopyrrolidin-1-yl]-2-oxoethylamino}cyclopentyl-methylsulfanyl)nictinonitrile maleate
40. 6-((1SR,3RS)-3-{2-[(2S)-2-Cyanopyrrolidin-1-yl)-2-oxoethylamino}cyclopentyl-methylsulfonyl)nicotinonitrile
41. (2S)-1-{2-[(3S,1R)-3-(2-Pyrimidinylsulfanylmethyl)cyclopentylamino]acetyl}-pyrrol-idine-2-carbonitrile
42. (2S)-1-{2-[(3S,1R)-3-(1H-Benzo[d]imidazol-2-ylsulfanylmethyl)cyclopentyl amino]-acetyl pyrrolidine-2-carbonitrile
43. (2S)-1-{2-[(3SR,1RS)-3-(4-Nitrophenoxymethyl)cyclopentylamino]acetyl}-pyrro-lidine-2-carbonitrile
44. (2S)-1-{2-[(3S,1R)-3-(4-Nitrophenoxymethyl)cyclopentylamino]acetyl}-pyrrolidine-2-carbonitrile
45. (2S)-1-{2-[(3R,1S)-3-(4-Nitrophenoxymethyl)cyclopentylamino]acetyl}-pyrrolidine-2-carbonitrile
46. (2S)-1-{2-[(1S,3R)-3-(4-Cyanophenoxymethyl)cyclopentylamino]acetyl}-pyrrolidine-2-carbonitrile
47. (2S)-1-{2-[(3S,1R)-3-(4-Cyanophenoxymethyl)cyclopentylamino]acetyl}-pyrrolidine-2-carbonitrile
48. (2S)-1-{2-[(3S,1R)-3-(4-Cyanophenoxymethyl)cyclopentylamino]acetyl}-pyrrolidine-2-carbonitrile dihydrochloride
49. (2S)-1-{2-[(3S,1R)-3-(4-Cyano-3-fluorophenoxymethyl)cyclopentylamino]acetyl}-pyrrolidine-2-carbonitrile
50. (2S,4S)-1-{2-[(3S,1R)-3-(4-Cyano-3-fluorophenoxymethyl)cyclopentylamino]acetyl}-4-fluoro-pyrrolidine-2-carbonitrile
51. (2S)-1-{2-[(3S,1R)-3-(1-Cyanodibenzo[b,d]furan-4-yloxymethyl)cyclopentylamino]-acetyl}-pyrrolidine-2-carbonitrile

DEFINITIONS

The term "aryl" refers to aromatic radicals having 6 to 14 carbon atoms, such as phenyl, naphthyl, tetrahydronapthyl, indanyl, and biphenyl.

The term "arylalkyl" refers to an aryl group directly bonded to an alkyl group, e.g., —CH$_2$C$_6$H$_5$, —C$_2$H$_5$C$_6$H$_5$ and the like.

The term "heterocyclic ring" refers to a stable 3- to 15 membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, and isochromanyl.

The term "heteroaryl" refers to an aromatic heterocyclic ring radical. The heteroaryl ring radical may be attached to the main structure at any heteroatom or carbon atom.

The term "heteroarylalkyl" refers to a heteroaryl ring radical directly bonded to an alkyl group. The heteroarylalkyl radical may be attached to the main structure at any carbon atom from the alkyl group.

The term "heterocyclyl" refers to a heterocyclic ring radical. The heterocyclyl ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at carbon atom in the alkyl group that results in the creation of a stable structure.

The term "alkyl" refers to a straight or branched hydrocarbon chain radical consisting solely of carbon and hydrogen atoms, having no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "alkenyl" refers to an aliphatic hydrocarbon group containing a carbon-carbon double bond and which may be a straight or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radicals having at least one carbon-carbon triple bond, and having in the range of about 2 up to 12 carbon atoms (with radicals having in the range of about 2 up to 10 carbon atoms presently being preferred) e.g., ethynyl, propynyl, and butnyl.

The term "alkoxy" denotes an alkyl group attached via an oxygen linkage to the rest of the molecule. Representative examples of those groups include, but are not limited to, —OCH$_3$, and —OC$_2$H$_5$.

The term "cycloalkyl" denotes a non-aromatic mono or multicyclic ring system of about 3 to 12 carbon atoms. Nonlimiting examples of noncyclopropyl, cyclobutyl, cyclopentyl, cyclohexyl and examples of non-aromatic mono multicyclic rings include perhydronapththyl, adamantyl and norbornyl groups, bridged cyclic groups or sprirobicyclic groups e.g. sprio (4,4) non-2-yl.

The term "cycloalkylalkyl" refers to a cycloalkyl radical containing about 3 to 8 carbon atoms directly attached to an alkyl group which are then attached to the main structure at any carbon from the alkyl group that results in the creation of a stable structure, such as cyclopropylmethyl, cyclobutylethyl, and cyclopentylethyl.

The term "cycloalkenyl" refers to a non-aromatic cyclic ring-containing radical containing about 3 to 8 carbon atoms with at least one carbon-carbon double bond such as cyclopropenyl, cyclobutenyl, and cyclopentenyl.

The substituents in the 'substituted alkyl', 'substituted alkoxy', 'substituted alkenyl', 'substituted alkynyl', 'substituted cycloalkyl', 'substituted cycloalkylalklyl', 'substituted cycloalkenyl', 'substituted aryl', 'substituted arylalkyl', 'substituted heteroaryl', 'substituted heterocyclic ring', 'substituted heterocycloalkyl', 'substituted heteroarylalkyl', 'substituted amino' and 'substituted carboxylic acid' derivatives, may be the same or different and may be one or more independently selected from the groups such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

As used herein, the term "treat" includes one or more of the following:

(a) arresting, delaying the onset (i.e., the period prior to clinical manifestation of a disorder) and/or reducing the risk of developing or worsening a disorder;

(b) relieving or alleviating at least one symptom of a disorder in a mammal, including for example, hypercalcemia; or (c) relieving or alleviating the intensity and/or duration of a manifestation of a disorder experienced by a mammal including, but not limited to, those which are in response to a given stimulus (e.g., pressure, tissue injury or cold temperature). The term "treat" also includes prophylaxis, i.e., prophylactically preventing, curing, healing, alleviating, relieving, altering, remedying, ameliorating, improving, or affecting a condition (e.g., a disease), the symptoms of the condition, or the predisposition toward the condition.

The phrase "pharmaceutically acceptable" refers to compounds or compositions that are physiologically tolerable and do not typically produce an allergic or similar untoward reaction, including, but not limited to, gastric upset or dizziness, when administered to a mammal.

An "effective amount" or "therapeutically effective amount " means the amount of a compound of the invention (including its solvates, active metabolites, prodrugs, or racemates or enantiomers thereof (assuming the salt has a chiral center)) that, when administered to a mammal for treating or preventing a state, disorder or condition is sufficient to effect such treatment or prophylaxis. The "effective amount" will vary depending on the active ingredient, the state, disorder, or condition to be treated and its severity, and the age, weight, physical condition and responsiveness of the mammal to be treated.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, andserine; quaternary ammonium salts of the compounds of invention with alkyl halides, alkyl sulphates such as MeI, and $(Me)_2SO_4$; non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate and include sulphates, nitrates, phosphates, perchlorates, borates, hydrohalides, acetates such as trifluroacetate, tartrates, maleates, citrates, fumarates, succinates, palmoates, methanesulphonates, benzoates, salicylates, benzenesulfonates, ascorbates, glycerophosphates, and ketoglutarates. Pharmaceutically acceptable solvates may be hydrates or comprise other solvents of crystallization such as alcohols.

The compounds of the present invention may form solvates with standard low molecular weight solvents using methods known to the skilled artisan.

In another aspect, the present invention includes within its scope pharmaceutical compositions comprising, as an active ingredient, at least one compound of the invention which inhibits the enzymatic activity of DPP-IV or a pharmaceutically acceptable salt or prodrug or hydrate thereof together with a pharmaceutically acceptable carrier or diluent.

Pharmaceutical compositions containing a compound of the present invention may be prepared by conventional techniques, such as described in *Remington: The Science and Practice of Pharmacy*, $20^{th}$. Ed., 2000. The compositions may be unit dosage forms, including, but not limited to, capsules, tablets, aerosols, solutions, suspensions or topical formulations.

Typical compositions include a compound of the invention which inhibits the enzymatic activity of DPP-IV or a pharmaceutically acceptable basic addition salt or prodrug or hydrate thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used.

For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

The pharmaceutical compositions can be sterilized and/or mixed, if desired, with auxiliary agents, emulsifiers, salt for influencing osmotic pressure, buffers and/or coloring substances, which do not deleteriously react with the active compounds.

The route of administration may be any route, which effectively transports the active compound of the invention which inhibits the enzymatic activity of DPP-IV to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment. The oral route is preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: 1 Core: Active compound (as free compound or salt thereof) 250 mg Colloidal silicon dioxide (Aerosil®) 1.5 mg Cellulose, microcryst. (Avicel®) 70 mg Modified cellulose gum (Ac-Di-Sol®) 7.5 mg Magnesium stearateAd. Coating: HPMC approx. 9 mg *Mywacett 9–40 T approx. 0.9 mg *Acylated monoglyceride used as plasticizer for film coating.

Where the term "compound of Formula I" is used, it is understood that this also encompasses subgeneric formulas II and III.

A further aspect of the present invention is the use of a compound of formula (I) as a pharmaceutical composition in a therapeutically effective amount for the treatment of a condition that may be regulated or normalized via inhibition of DPP-IV.

A further aspect of the present invention is the use of a compound of formula (I) as a pharmaceutical composition in a therapeutically effective amount for the treatment of metabolic disorders.

A further aspect of the present invention is the use of a compound of formula (I) as a pharmaceutical composition in a therapeutically effective amount for lowering blood glucose.

A further aspect of the present invention is the use of a compound of formula (I) as a pharmaceutical composition in a therapeutically effective amount for the treatment of Type II diabetes.

A further aspect of the present invention is the use of a compound of formula (I) as a pharmaceutical composition in a therapeutically effective amount for the treatment of impaired glucose tolerance (IGT).

A further aspect of the present invention is the use of a compound of formula (I) as a pharmaceutical composition in a therapeutically effective amount for the treatment of impaired fasting glucose (IFG).

A further aspect of the present invention is the use of a compound of formula (I) as a pharmaceutical composition in a therapeutically effective amount for the prevention of hyperglycemia.

A further aspect of the present invention is the use of a compound of formula (I) as a pharmaceutical composition in a therapeutically effective amount for delaying the progression of impaired glucose tolerance (IGT) to Type II diabetes.

A further aspect of the present invention is the use of a compound of formula (I) as a pharmaceutical composition in a therapeutically effective amount for delaying the progression of non-insulin requiring Type II diabetes to insulin requiring Type II diabetes.

A further aspect of the present invention is the use of a compound of formula (I) as a pharmaceutical composition in a therapeutically effective amount for increasing the number and/or the size of beta cells in a subject.

A further aspect of the present invention is the use of a compound of formula (I) as a pharmaceutical composition in a therapeutically effective amount for the treatment of beta cell degeneration, in particular apoptosis of beta cells.

A further aspect of the present invention is the use of a compound of formula (I) as a pharmaceutical composition in a therapeutically effective amount for the treatment of disorders of food intake.

A further aspect of the present invention is the use of a compound of formula (I) as a pharmaceutical composition in a therapeutically effective amount for the treatment of obesity.

A further aspect of the present invention is the use of a compound of formula (I) as a pharmaceutical composition in a therapeutically effective amount for appetite regulation or induction of satiety.

A further aspect of the present invention is the use of a compound of formula (I) as a pharmaceutical composition in a therapeutically effective amount for the treatment of dyslipidemia.

A further aspect of the present invention is the use of a compound of formula (I) as a pharmaceutical composition in a therapeutically effective amount for the treatment of functional dyspepsia, in particular irritable bowel syndrome.

The compounds of the invention may be administered to a mammal, especially a human in need of such treatment, prevention, elimination, alleviation or amelioration of the various diseases as mentioned above, e.g., Type II diabetes, IGT, IFG, obesity, and appetite regulation, or as a blood glucose lowering agent. The compounds of the invention are particularly useful for treating Type II diabetes in mammals. Such mammals include also humans, domestic animals, e.g. household pets, and non-domestic animals such as wildlife.

The compounds of the invention are effective over a wide dosage range. For example, in the treatment of adult humans, dosages from about 0.05 to about 1000 mg, preferably from about 0.1 to about 500 mg, per day may be used. A most preferable dosage is about 0.5 mg to about 250 mg per day. In choosing a regimen for patients it may frequently be necessary to begin with a higher dosage and when the condition is under control to reduce the dosage. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage forms comprising from about 0.05 to about 1000 mg of active ingredient together with a pharmaceutically acceptable carrier per unit dosage.

According to one embodiment, dosage forms suitable for oral, nasal, pulmonary or transdermal administration comprise from about 0.05 mg to about 1000 mg, preferably from about 0.5 mg to about 250 mg of the compounds admixed with a pharmaceutically acceptable carrier or diluent.

Still another embodiment of the present invention encompasses prodrugs of a compound, which on administration undergo chemical conversion by metabolic processes before becoming active pharmacological substances. In general, such prodrugs will be functional derivatives of a compound of the invention, which are readily convertible in vivo into a compound of the invention. Conventional procedures for the selection and preparation of suitable prodrug derivatives are described, for example, in H. Bundgaard, *Design of Prodrugs,* Elsevier (1985 ed.).

The invention also encompasses active metabolites of a compound of the invention.

General Methods:

The compounds of formula (I) maty be synthesized according to the general scheme given below General Scheme Step 1

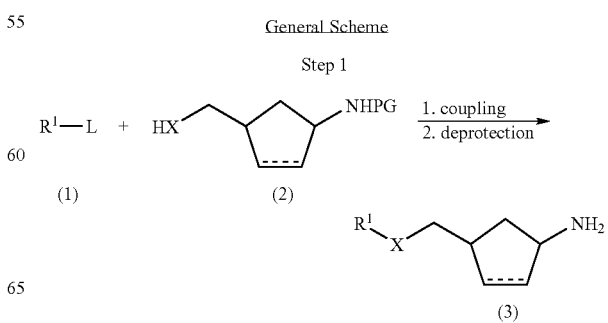

-continued
Step 2

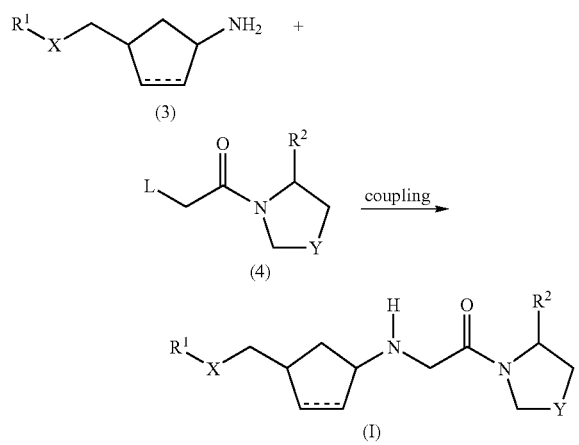

wherein L is a leaving group and PG is protecting group.

The compounds of general formula (I) can be prepared using a variety of methods known in the literature and known to those skilled in the art. One such approach is given in the general synthetic scheme above. The intermediate of general formula (1) can be coupled with a mono-protected bifunctional intermediate of the general formula (2) and the coupled product can be deprotected to yield intermediate of general formula (3). Compounds of the general formula (I) can be obtained by coupling of intermediates (3) and (4) using a suitable base, such as triethylamine or $K_2CO_3$. The coupling sequence of the fragments (1)–(4) can be altered and the compounds of general formula I can be obtained by a variety of other methods known to persons skilled in the art.

The compounds can be isolated and purified by methods known in the art, e.g., by distilling off the solvent in a vacuum and recrystallizing the residue obtained from a suitable solvent or subjecting it to a purification method, such as column chromatography on a suitable support material.

Salts are obtained by dissolving the free compound in a suitable solvent, e.g, in a chlorinated hydrocarbon, such as methylene chloride or chloroform or a low molecular weight aliphatic alcohol (ethanol, isopropanol), which contains the desired acid or base, or to which the desired acid or base is then added. The salts are obtained by filtering, reprecipitating, precipitating with a non-solvent for the addition salt or by evaporating the solvent. Salts obtained can be converted by basification or by acidifying into the free compounds which, in turn can be converted into salts.

In general, the ethereal solvents used in the above described processes for the preparation of compounds of the formula (I) are selected from diethyl ether, 1,2-dimethoxyethane, tetrahydrofuran, diisopropyl ether, and 1,4 dioxane. The chlorinated solvent which may be employed may be selected from dichloromethane, 1,2-dichloroethane, chloroform, and carbontetrachloride. The aromatic solvents which may be employed may be selected from benzene and toluene. The alchoholic solvents which may be employed may be selected from methanol, ethanol, n-propanol, iso propanol, and tert-butanol. The aprotic solvents which may be employed may be selected from N, N-dimethylformamide, dimethyl sulfoxide and the like.

In general, the compounds prepared in the above described processes are obtained in pure form by using well known techniques such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pet.ether), chloroform, ethyl acetate, acetone, methanol or their combinations.

Various polymorphs of a compound of general formula (I) forming part of this invention may be prepared by crystallization of compound of formula (I) under different conditions. example, using different solvents commonly used or their mixtures for recrystallization; crystallizations at different temperatures, various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides novel organic compounds of general formula (I), their analogs, their tautomers, their regioisomers, their stereoisomers, their enantiomers, their diastreomers, their polymorphs, their pharmaceutically acceptable salts, their appropriate N-oxides and their pharmaceutically acceptable solvates.

The present invention also provides with a novel organic compounds of general formula (2) their analogs, their tautomers, their regioisomers, their stereoisomers, their enantiomers, their diastreomers and the salts thereof.

The present invention also provides with a novel organic compounds of general formula (3) their analogs, their tautomers, their regioisomers, their stereoisomers, their enantiomers, their diastreomers and the salts thereof The present invention also provides pharmaceutical compositions, containing compounds of general formula (I) as defined above, their derivatives, their analogs, their tautomeric forms, their stereoisomers, their polymorphs, their enantiomers, their diasteromers, their pharmaceutically acceptable salts or their pharmaceutically acceptable solvates in combination with the usual pharmaceutically employed carriers, diluents and the like. The pharmaceutical compositions according to this invention can be used for the treatment of allergic disorders.

It will be appreciated that some of the compounds of general formula (I) defined above according to the invention can contain one or more asymmetrically substituted carbon atoms. The presence of one or more of these asymmetric centers in the compounds of general formula (I) can give rise to stereoisomers and in each case the invention is to be understood to extend to all such stereoisomers, including enantiomers and diastereomers and their mixtures, including racemic mixtures. The invention may also contain E & Z geometrical isomers wherever possible in the compounds of general formula (I) which includes the single isomer or mixture of both the isomers.

EXAMPLES

The following examples are provided to enable one skilled in the art to practice the invention and are merely illustrative of the invention. The examples should not be read as limiting the scope of the invention as defined in the claims.

Intermediate 1 cis-(±)-4-N—BOC-Aminocyclopent-2-ene-1-carboxylic acid

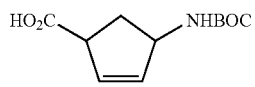

Step 1: (±)-2-N—BOC-Azabicyclo[2,2,1]hept-5-ene-3-one: A solution of di-tert-butyl dicarbonate (144 g, 660.5 mmol) in THF (100 ml) was added (20 min) to a stirred solution of (±)-2-azabicyclo[2,2,1]hept-5-ene-3-one (60 g, 549.8 mmol), triethylamine (83.5 g, 824.6 mmol) and 4-dimethylaminopyridine (6.7 g, 54.8 mmol) in THF (500 ml) at room temperature. The reaction mixture was stirred for another 4 h at room temperature. The solvent was evaporated under reduced pressure and the residue was diluted with EtOAc (800 ml) and washed with water (3×500 ml) and brine (400 ml). The EtOAc extract was dried ($Na_2SO_4$) and evaporated under reduced pressure to give 115 g of the compound as a white solid; IR (KBr) 2979, 1755, 1705, 1455, 1331, 1305, 1149, 1117 $cm^{-1}$; $^1H$ NMR ($CDCl_3$, 300 MHz) δ 1.50 (s, 9H), 2.13–2.16 (m, 1H), 2.33–2.37 (m, 1H), 3.38–3.40 (m, 1H), 4.94–4.96 (m, 1H), 6.44–6.67 (m, 1H), 6.88–6.90 (m, 1H).

Step 2: cis-(±)-4-N—BOC-Aminocyclopent-2-ene-1-carboxylic acid: To a stirred solution of Step 1 intermediate (30.0 g, 143.3 mmol) in tetrahydrofuran (100 ml) was added 1N sodium hydroxide solution (300 ml) and the mixture was stirred at 40° C. for 20 h. The reaction mixture was cooled to 0° C. and acidified to pH 3.5 with 1N hydrochloric acid. The mixture was extracted with dichloromethane (3×200 ml) and the combined extracts were washed with water (2×300 ml), brine (300 ml) and dried ($Na_2SO_4$). The solvent was evaporated under reduced pressure to give 31.5 g of the product as a white solid; IR (KBr) 3408, 3222, 2982, 1724, 1681, 1504, 1392 cm-1; 1H NMR (CDCl3, 300 MHz) δ 1.45 (s, 9H), 1.87–2.03 (m, 1H), 2.37–2.60 (m, 1H), 3.49 (brs, 1H), 4.60 (brs, 1H), 4.49 (brs, 1H), 5.90 (brs, 2H), 9.01 (brs, 1H).

Intermediate 2 cis-(±)-3-N—BOC-Aminocyclopentane-1-carboxylic acid

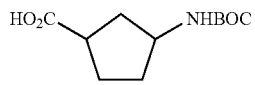

Method A:

To a solution of Intermediate 1 (15 g, 66.0 mmol) in methanol (100 ml) was added 5% Pd—C (1.0 g) and the mixture was maintained under hydrogen pressure (40 psi) for 2 h at room temperature. The catalyst was then filtered off and the filtrate was concentrated under reduced pressure to give 14.9 g of the product as a white solid; IR (KBr) 3304, 3249, 3098, 2978, 1705, 1646, 1403, 1164 $cm^{-1}$; $^1H$ NMR ($CDCl_3$, 300 MHz) δ 1.42 (s, 9 H), 1.53–2.20 (m, 5 H), 2.11–2.35 (m, 1H), 2.73–3.01 (m, 1H), 4.05 (brs, 1H), 4.86 (brs, 1H).

Method B:

Step 1: cis-(±)-2-N—BOC-Azabicyclo[2,2,1]heptane-3-one. To a solution of cis-(±)-2-N—BOC-Azabicyclo[2,2,1]hept-5-ene-3-one (18.0 g, 86.02 mmol) obtained from Intermediate 1, Step 1 in EtOAc (180 ml) was added 5% Pd/C (1.5 g) and the mixture was maintained under hydrogen pressure (40 psi) for 2 h at room temperature. The catalyst was then filtered off and the filtrate was concentrated under reduced pressure to give 18.1 g (99.6%) of the compound as a white solid; IR (KBr) 2982, 1754, 1708, 1349, 1316, 1217, 1155, 1096, 921 $cm^{-1}$; $^1H$ NMR ($CDCl_3$, 300 MHz) δ 1.42 (d, J=10.2 Hz, 1H), 1.52 (s, 9H), 1.73–1.96 (m, 5H), 2.86 (brs, 1H), 4.53 (brs, 1H).

Step 2: cis-(±)-3-N—BOC-Aminocyclopentane-1-carboxylic acid: To a stirred solution of Step 1 intermediate (9.0 g, 42.60 mmol) in tetrahydrofuran (45 ml) was added 1N sodium hydroxide solution (90 ml) and the mixture was stirred at 50° C. for 24 h. The reaction mixture was cooled to 0° C. and acidified to pH 3.5 with 1N hydrochloric acid. The mixture was extracted with dichloromethane (3×100 ml) and the combined extracts were washed with water (2×100 ml), brine (100 ml) and dried ($Na_2SO_4$). The solvent was evaporated under reduced pressure to give 9.5 g (97%) of the product as a white solid. The product isolated was identical in all respects with that obtained from Method A.

Intermediate 3 cis-(±)-3-N—BOC-Aminocyclopentylmethanol

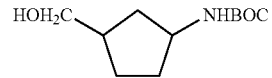

Method A: Sodium borohydride (1.43 g, 37.8 mmol) was added to a stirred solution of (±)-2-N—BOC-Azabicyclo[2,2,1]-heptane-3-one (8.0 g, 37.86 mmol) obtained from Step 1, Method B of Intermediate 2 in 10% aqueous THF (100 ml) at 0° C. A second lot of sodium borohydride (1.43 g, 37.8 mmol) was added after 0.5 h at the same temperature and the mixture was stirred at 0–10° C. for 4 h. The excess reagent was quenched with 1N HCl and the reaction mixture acidified to pH 5.0. The mixture was extracted with ethyl acetate (3×200 ml) and the combined organic extracts were washed with water (3×200 ml) followed by brine (200 ml). The solvent was evaporated under reduced pressure to give 6.9 g (85%) of the compound as a white solid; IR (KBr) 3361, 2969, 1683, 1524, 1366, 1271, 1172, 1017 $cm^{-1}$; $^1H$ NMR ($CDCl_3$, 300 MHz) δ 1.11–1.16 (m, 1H), 1.40–1.53 (m, 2H), 1.44 (s, 9H), 1.71–1.79 (m, 1H), 1.87–1.95 (m, 1H), 2.15–2.01 (m, 2H), 3.57 (t, J=5.1 Hz, 2H), 3.94 (brs, 1H), 4.73 (brs, 1H).

Method B: Ethyl chloroformate (4.73 g, 43.58 mmol) was added to a stirred solution of Intermediate 2 (10 g, 43.66 mmol) and TEA (4.42 g, 43.76 mmol) in dry THF (100 ml) at 0° C. over 5 min under nitrogen atmosphere. The reaction mixture was stirred for another 30 min at the same temperature. It was then filtered to remove the precipitated triethylamine hydrochloride. The filtrate containing the mixed anhydride was slowly added to a stirred suspension of $NaBH_4$ (4.95 g, 130.84 mmol) in 20% aqueous THF (100 ml) maintained at 10° C. The mixture was stirred for another 30 min at the same temperature and then acidified with 1N HCl to pH 4. The mixture was extracted with EtOAc (3×200 ml)

and the organic layer was washed with 2N NaOH solution (2×250 ml), water (2×250 ml) and brine (300 ml). The solvent was evaporated under reduced pressure to give 7.01 (75%) of the alcohol as a white solid. IR and ¹H NMR spectra of the product were identical in all respects with the compound obtained from Method A.

Intermediate 4 cis-(±)-3-N—BOC-Aminocyclopentylmethyl methanesulfonate

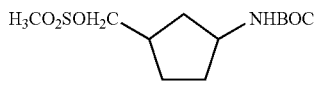

Methanesulfonyl chloride (3.51 g, 30.6 mmol) was added to a stirred and cooled (10° C.) solution of Intermediate 3 (6 g, 27.88 mmol), and triethylamine (3.66 g, 36.16 mmol) in dry dichloromethane (100 ml) under nitrogen atmosphere. The mixture was stirred at the same temperature for 15 min and then diluted with water (150 ml). The organic and aqueous layers were separated. The aqueous layer was extracted with dichloromethane (100 ml) and the combined organic extracts were washed with water (2×200 ml) and dried ($Na_2SO_4$). The solvent was evaporated under reduced pressure to give 8.2 g (100%) of the compound as a white solid: IR (KBr) 3361, 2969, 2870, 1678, 1529, 1349, 1286, 1252, 1167, 1052, 973 cm$^{-1}$; ¹H NMR ($CDCl_3$, 300 MHz) δ 1.11–1.20 (m, 1H), 1.41–1.56 (m, 2H), 1.44 (s, 9H), 1.75–1.88 (m, 1H), 1.94–1.98 (m, 1H), 2.01–2.94 (m, 2H), 3.02 (s, 3H), 3.95 (brs, 1H), 4.15 (d, J=6.6 Hz, 2H), 4.53 (brs, 1H).

Intermediate 5 cis-(±)-3-N—BOC-Aminocyclopentylmethylamine

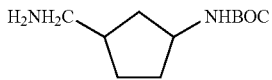

Step 1: cis-(±)-3-N—BOC-Aminocyclopentylmethyl azide: Sodium azide (3.1 g, 47.6 mmol) was added to a stirred solution of Intermediate 4 (7.0 g, 23.8 mmol) in DMF (100 ml) and the mixture was stirred at 60° C. for 6 h under nitrogen atmosphere. The mixture was cooled to room temperature and diluted with EtOAc (500 ml) and water (500 ml). The layers were separated and the organic layer was washed with water (3×300 ml) and brine (300 ml). The solvent was evaporated under reduced pressure to give 5.7 g (100%) of the azide as an oil; IR (neat) 3338, 2965, 2870, 2096, 1696, 1515, 1453, 1365, 1251, 1171 cm$^{-1}$; ¹H NMR ($CDCl_3$, 300 MHz) δ 1.06–1.13 (m, 1H), 1.37–1.52 (m, 2H), 1.44 (s, 9H), 1.75–1.86 (m, 1H), 1.94–2.05 (m, 1H), 2.14–2.29 (m, 2H), 3.28 (d, J=6.6 Hz, 2H), 3.94 (brs, 1H), 4.55 (brs, 1H).

Step 2: cis-(±)-3-N—BOC-Aminocyclopentylmethylamine: To a solution of azide, from Step 1 (5.0 g, 20.8 mmol) in methanol (100 ml) was added 5% Pd—C (300 mg) and the mixture was maintained under hydrogen pressure (40 psi) for 3 h at room temperature. The catalyst was filtered off and the filtrate was concentrated under reduced pressure to give 4.45 g of the amine as a semisolid, which was used as such for the coupling reaction.

Intermediate 6

(1S,3R)-(+)-3-N—BOC-Aninocyclopentane-1-carboxylic acid

Method A:
Step 1: (1S,4R)-(+)-4-N—BOC-Azabicyclo[2,2,1]hept-5-ene-3-one: This intermediate was prepared from (1S,4R)-(+)-2-azabicyclo[2,2,1]hept-5-ene-3-one (10 g, 91.74 mmol) and di-tert-butyl dicarbonate (26 g, 119.26 mmol) in the presence of triethylamine (13.92 g, 137.5 mmol) and DMAP (1.1 g, 9.17 mmol) in THF (50 ml) as described in Intermediate 1, Step 1 to give 19.3 g, (100%) of the product as a white solid; IR and ¹H NMR spectra of the product were identical with that of the racemic product from Intermediate 2.

Step 2: (1R,4S)-(+)-2-N—BOC-Azabicyclo[2,2,1]heptan-3-one: The Step 1 intermediate (9.0 g, 43.26 mmol) was hydrogenated using 5% Pd—C (1.0 g) as described in Method B, Intermediate 2 gave 9.0 g of the product as a white solid; IR and ¹H NMR spectra were identical with that of the racemic product.

Step 3: (1S,3R)-(+)-3-N—BOC-Aminocyclopentane-1-carboxylic acid: Hydrolytic cleavage of Step 2 intermediate (8.5 g, 40.26 mmol) as described in Intermediate 2, Method B, Step 2 gave the desired product as a white solid. IR and ¹H NMR spectra were identical with that of the racemic intermediate. [α]$_D$+12.2° (c=1.0, MeOH).

Method B:
Step 1: (4S,1R)-(+)-4-N—BOC-Aminocyclopent-2-ene-1-carboxylic acid: This intermediate was prepared by the optical resolution of Intermediate I using (S)-(−)-phenyl ethyl amine in a mixture of isopropanol and ethanol. [α]$_D$+48.0° (c=1.0, MeOH).

Step 2: (1S,3R)-(+)-3-N—BOC-Aminocyclopentane-1-carboxylic acid: To a solution of Step 1 intermediate (8.0 g, 35.2 mmol) in ethyl acetate (150 ml) was added 5% Pd—C (1.0 g) and the mixture was maintained under hydrogen pressure (40 psi) for 3 h at RT to give 8.0 g of the product as a white solid, which was identical in all respects with the product obtained from Method A.

Intermediate 7

(1S,3R)-(+)-3-N—BOC-Aminocyclopentylmethanol

Method A: This intermediate was prepared by the reductive cleavage of (1R,4S)-(+)-2-N—BOC-Azabicyclo[2,2,1] heptan-3-one (8.0 g, 37.86 mmol) with sodium borohydride (2.86 g, 75.6 mmol) in 10% aq. THF (100 ml) as described in Intermediate 3, Method A to give 6.95 g (85%) of the product as a white solid; $[\alpha]_D$+8.7° (c=1.0, MeOH).

Method B: The mixed anhydride of (1S,3R)-(+)-3-N—BOC-Aminocyclopentane-1-carboxlic acid (9.0 g, 39.3 mmol) prepared from ethyl chloroformate (4.69 g, 43.21 mmol) and TEA (4.36 g, 43.08 mmol) in dry THF was treated with $NaBH_4$ (4.45 g, 117.6 mmol) in 20% aqueous THF as described in Intermediate 3, Method B to give 7.0 (83.3%) of the alcohol as a white solid, which was identical in all respects with the product obtained from Method A.

Intermediate 8

(1S,3R)-(+)-3-N—BOC-Aminocyclopentylmethyl methanesulfonate

Reaction of Intermediate 7 (6.5 g, 30.2 mmol) with methanesulfonyl chloride (3.8 g, 33.18 mmol) in the presence of triethylamine (3.97 g, 39.2 mmol) in dry dichloromethane (150 ml) as described in Intermediate 4 gave 8.5 g (96.5%) of the product as a white solid; $[\alpha]_D$+15.9° (c=1.0, MeOH).

Intermediate 9

(1S,3R)-3-N—BOC-Aminocyclopentylmethylamine

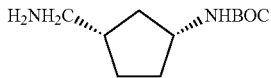

Step 1: (1S,3R)-3-N—BOC-Aminocyclopentylmethyl azide: Reaction of Intermediate 8 (8.0 g, 27.3 mmol) with sodium azide (3.5 g, 53.8 mmol) in dry DMF (150 ml) as described in Intermediate 5 gave 6.5 g (100%) of the azide as an oil.

Step 2: (1S,3R)-3-N—BOC-Aminocyclopentylmethylamine: The azide (6.0 g, 25.0 mmol) from Step 1 dissolved in methanol (150 ml) was reduced with 5% Pd/C (300 mg) as described in Intermediate 5, Step 2 to give 5.35 g (100%) of the amine as a semisolid, which was used as such for the coupling reaction.

Intermediate 10

(3S,1R)-(−)-3-N—BOC-Aminocyclopentane-1-carboxylic acid

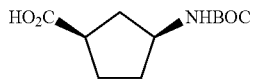

Method A:

Step 1: (4S,1R)-(−)-2-N—BOC-Azabicyclo[2,2,1]hept-5-ene-3-one: This intermediate was prepared from (1R,4S)-(−)-2-azabicyclo[2,2,1]hept-5-ene-3-one (10 g, 91.74 mmol) and di-tert-butyl dicarbonate (23.9 g, 109.6 mmol) in the presence of triethylamine (13.90 g, 137.3 mmol) and DMAP (1.1 g, 9.00 mmol) in THF (50 ml) as described in Intermediate 2, Step 1 (Method B) to give 19.1 g (100%) of the product as a white solid; IR and $^1$H NMR spectra were identical with that of the racemic intermediate.

Step 2: (4R,1S)-(−)-2-N—BOC-Azabicyclo[2,2,1]heptan-3-one: Step 1 intermediate (9.0 g, 43.01 mmol) was hydrogenated using Pd—C (1.0 g) as described in Intermediate 2, Step 1 (Method B) to give 9.0 g of the product as a white solid: IR and $^1$H NMR spectra of the product were identical with that of racemic intermediate.

Step 3: (3S,1R)-(−)-3-N—BOC-Aminocyclopentane-1-carboxylic acid: Hydrolytic cleavage of Step 2 intermediate (8.0 g, 37.8 mmol) as described in Intermediate 2, Step 2 (Method B) gave 6.5 g of the desired product as a white solid; IR and $^1$H NMR spectra were identical with that of the racemic intermediate. $[\alpha]_D$−48.3° (c=1.0, MeOH).

Method B:

Step 1: (1S,4R)-(−)-4-N—BOC-Aminocyclopent-2-ene-1-carboxylic acid: This intermediate was prepared by the optical resolution of Intermediate I using (R)-(+)-phenyl ethyl amine in a mixture of isopropanol and ethanol. $[\alpha]_D$+48.0° (c=1.0, MeOH).

Step 2: (3S,1R)-(−)-3-N—BOC-Aminocyclopentane-l-carboxylic acid: The Step 1 intermediate (8.0 g, 35.2 mmol) in ethyl acetate (100 ml) was reduced with 5% Pd—C (1.0 g) as described in Intermediate 2, Method A to give 8.01 g of the product as a white solid, which was identical in all respects with the product obtained from Method A.

Intermediate 11

(3S,1R)-(−)-3-N—BOC-Aminocyclopentylmethanol

Method A: Reductive cleavage of (4S,1R)-(−)-2-N—BOC-Azabicyclo[2,2,1]heptanene-3-one (10 g, 47.33 mmol) using sodium borohydride (3.58 g, 94.6 mmol) in 10% aqueous THF (100 ml) as described in Intermediate 3, Method A, gave 8.5 g of the product as a white solid, which showed identical IR and $^1$H NMR spectra to its racemate. $[\alpha]_D$−8.7° (c=1.0, MeOH).

Method B:

Reduction of (3S,1R)-(−)-3-N—BOC-Aminocyclopentane-1-carboxylic acid (8.5 g, 37.07 mmol) as described in the preparation of Intermediate 3, Method B gave 7.0 g of the alcohol as a white solid, which was identical in all respects with the product obtained from Method A.

Intermediate 12

(3S,1R)-(−)-3-N—BOC-Aminocyclopentylmethyl methanesulfonate

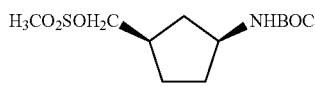

Reaction of Intermediate 11 (6.5 g, 30.2 mmol) with methanesulfonyl chloride (3.8 g, 33.18 mmol) in the presence of triethylamine (3.97 g, 39.2 mmol) in dry dichloromethane (100 ml) under nitrogen atmosphere as described in Intermediate 4 gave 8.5 g (96.5%) of the product as a white solid. $[\alpha]_D$−15.5° (c=1.0, MeOH).

Intermediate 13

(3S,1R)-(−)-3-N—BOC-Aminocyclopentylmethylamine

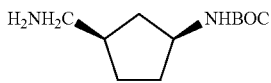

Step 1: (3S,1R)-3-N—BOC-Aminocyclopentylmethyl azide: Intermediate 12 (8.0 g, 27.3 mmol) was treated with sodium azide (3.5 g, 54.4 mmol) in DMF (150 ml) as described in Intermediate 5, Step 1 to give 6.5 g (100%) of the azide as an oil.

Step 2: (3S,1R)-3-Aminocyclopentylmethylamine: The azide (6.0 g, 25.0 mmol) from Step 1 in methanol (150 ml) was reduced with 5% Pd/C (300 mg) as described in Intermediate 5, Step 2 to give 5.35 g (100%) of the amine as a semisolid, which was used as such for the coupling reaction.

Intermediate 14 cis-(±)-4-N—BOC-Aminocyclopent-2-enylmethylamine

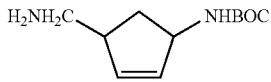

Step 1: cis-(±)-4-N—BOC-Aminocyclopent-2-enylmethanol:

Method A: To a solution of cis-(±)-2-N—BOC-Azabicyclo[2,2,1]hept-5-ene-3-one (5.0 g, 23.89 mmol) obtained from Intermediate 1, Step 1 in 10% aqueous THF (50 ml) was added sodium borohydride (1.8 g, 47.78 mmol) and the mixture was stirred at 0–10° C. for 5 h. Excess reagent was quenched with 1N HCl and the pH was adjusted to 6. The mixture was extracted with ethyl acetate (2×100 ml) and the combined extracts were washed with water (200 ml), brine (100 ml) and dried ($Na_2SO_4$). The solvent was evaporated under reduced pressure to give 4.17 g of the product as a viscous liquid; IR (KBr) 3319, 1960, 1683, 1536, 1366, 1248, 1170, 1043, 1001 cm$^{-1}$; $^1$H NMR (CDCl$_3$, 300 MHz) δ 1.36–1.46 (m, 1H), 1.44 (s, 9H), 2.44–2.55 (m, 1H), 2.84 (brs, 1H), 3.55–3.69 (m, 2H), 4.69 (brs, 1H), 4.85 (brs, 1H), 5.75–5.84 (m, 2H).

Method B: This compound was also prepared by calcium borohydride reduction of Methyl cis-(±)-4-N—BOC-amino-2-cyclopentene-1-carboxylate as described in the literature (J. Chem. Soc. Perkin Trans. 1, 1992, 589–592).

Step 2: cis-(±)-4-N—BOC-Aminocyclopent-2-enylmethyl methanesulfonate: Reaction of Step 1 intermediate (3.5 g, 16.26 mmol) with methanesulfonyl chloride(2.04 g, 17.8 mmol) in the presence of triethylamine (2.14 g, 21.14 mmol) in dry dichloromethane as described in the preparation of intermediate 4 gave 3.9 g of the product as a white solid; IR (KBr) 3356, 2987, 1682, 1514, 1348, 1241, 1167, 1065, 973 cm$^{-1}$; $^1$H NMR (CDCl$_3$, 300 MHz) δ 1.31–1.46 (m, 2H), 1.44 (s, 9H), 2.54–2.62 (m, 1H), 3.03 (s, 3H), 4.17 (dd, J=4.2, 1.5 Hz, 2H), 4.64 (brs, 1H), 4.74 (brs, 1H), 5.77–5.84 (m, 2H)

Step 3: cis-(±)-4-N—BOC-Aminocyclopentenylmethyl azide: This compound was prepared from Step 2 intermediate (3.5 g, 11.94 mmol) and sodium azide (1.58 g, 23.88 mmol) in DMF (35 ml) as described in the preparation of Intermediate 5, Step 1 to give 2.8 g of the product as an oil; IR (neat) 3339, 2976, 2096, 1696, 1511, 1366, 1247, 1170, 1068 cm$^{-1}$; $^1$H NMR (CDCl$_3$, 300 MHz) δ 1.24–1.32 (m, 1H), 1.45 (s, 9H), 2.51–2.61 (m, 1H), 2.86–2.92 (m, 1H), 3.28–3.40 (m, 2H), 4.70 (brs, 2H), 5.76–5.81 (m, 2H). Step 4: cis-(±)-4-N—BOC-Amino-2-cyclopentenylmethylamine. Triphenylphosphine (3.0 g, 11.43 mmol) was added to a stirred solution of the azide from Step 3 (2.5 g, 10.49 mmol) in dry THF (20 ml) at RT over 30 min under nitrogen atmosphere. The reaction was quenched with water (0.5 ml) and further stirred for 1 h. The solvent was evaporated under reduced pressure and the residue was diluted with ethyl acetate. The mixture was filtered to remove the precipitated triphenylphosphine oxide and the filtrate was evaporated to give the crude amine, which was used as such for the coupling reaction.

Intermediate 15 trans-(±)-3-N—BOC-Aminocyclopentylmethylamine

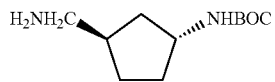

Step 1: cis-(±)-Methyl 3-N—BOC-Aminocyclopentane-1-carboxylate: This intermediate was prepared by the hydrolytic cleavage of cis-(±)-2-azabicyclo[2,2,1]heptane-3-one followed by esterification and amino group protection by following a similar approach as described in the literature (Tetrahedron Lett. 1997, 38, 5371–5374): IR (KBr) 3375, 2976, 2875, 1713, 1519, 1366, 1249, 1201, 1171 cm$^{-1}$; $^1$H NMR (CDCl$_3$, 300 MHz) δ 1.44 (s, 9H), 1.58–1.79 (m, 2H), 1.87–2.01 (m, 2H), 2.10–2.28 (m, 1H), 2.78–2.95 (m, 1H), 3.69 (s, 3H), 4.08 (brs, 1H), 4.95 (brs, 1H).

Step 2: trans-(±)-Methyl-3-N—BOC-Aminocyclopentane-1-carboxylate: To a solution of Step 1 intermediate (20 g, 82.20 mmol) in dry methanol (200 ml) was added sodium methoxide (6.65 g, 123.30 mmol) and the mixture was stirred at 50° C. for 6 h to result an equilibrium mixture of cis- and trans esters. The more polar trans ester was separated from the cis isomer by careful silica gel column chromatography using 5% EtOAc in petroleum ether as eluent.

Step 3: trans-(±)-3-N—BOC-Aminocyclopentylmethanol: To a stirred and cooled (0° C.) solution of Step 2 intermediate (8.0 g, 34.89 mmol) in dry THF (100 ml) was added lithium borohydride (2.64 g, 69.8 mmol) in portions over a period of 30 min. The mixture was further stirred at RT for 12 h. Excess lithium borohydride was quenched with 1N HCl at 0° C. The mixture was extracted with dichloromethane (2×100 ml) and the combined extracts were washed with water (200 ml), brine (100 ml) and dried (Na$_2$SO4). The solvent was evaporated under reduced pressure to give 4.3 g of the product as a white solid; IR (KBr) 3338, 2973, 1688, 1526, 1391, 1366, 1300, 1250, 1171, 1047 cm$^{-1}$; $^1$H NMR (CDCl$_3$, 300 MHz) δ 1.27–1.47 (m, 2H), 1.44 (s, 9H), 1.51–1.65 (m, 1H), 1.67–1.91 (m, 2H), 2.00–2.05 (m, 1H), 2.18–2.30 (m, 1H), 3.51 (d, J=7.2 Hz, 2H), 3.98 (brs, 1H), 4.58 (brs, 1H).

Step 4: trans-(±)-3-N—BOC-Aminocyclopentylmethyl methanesulfonate: Reaction of Step 3 intermediate (4.0 g, 18.57 mmol) with methanesulfonyl chloride (2.34 g, 20.4 mmol) in the presence of triethylamine (2.44 g, 24.1 mmol) in dry dichloromethane (80 ml) as described in Intermediate 4 gave 5.2 g of the product as a white solid; IR (KBr) 3342, 1977, 1681, 1532, 1359, 1346, 1248, 1170, 1103, 976, 950 cm$^{-1}$; $^1$H NMR (CDCl$_3$, 300 MHz) δ 1.32–1.51 (m, 2H), 1.44 (s, 9H), 1.68–1.75 (m, 2H), 1.91–1.96 (m, 1H), 2.04–2.08 (m, 1H), 2.47 (quint, J=7.5 Hz, 1H), 3.01 (s, 3H), 4.00 (brs, 1H), 4.10 (d, J=6.6 Hz, 2H), 4.50 (brs, 1H).

Step 5: trans-(±)-3-N—BOC-Aminocyclopentylmethyl azide: This compound was prepared from Step 4 intermediate (4.8 g, 16.36 mmol) and sodium azide (2.13 g, 32.7 mmol) in DMF (50 ml) as described in the preparation of Intermediate 5, Step 1 to give 3.9 g of the product as an oil; IR (neat) 3345, 1969, 2097, 1703, 1511, 1453, 1365, 1248, 1174, 1016 cm$^{-1}$; $^1$H NMR (CDCl$_3$, 300 MHz) δ 1.23–1.48 (m, 2H), 1.44 (s, 9H), 1.65–1.70 (m, 2H), 1.86–1.97 (m, 1H), 2.01–2.09 (m, 1H), 2.52–2.35 (m, 1H), 3.22 (dd, J=5.7, 1.5 Hz, 2H), 4.00 (brs, 1H), 4.50 (brs, 1H).

Step 6: trans-(±)-3-N—BOC-Aminocyclopentylmethylamine: The azide (3.5 g, 14.56 mmol) from Step 5 in methanol (50 ml) was reduced with 5% Pd/C (180 mg) as described in Intermediate 5, Step 2 to give 3.1 g of the amine as a semisolid; IR (neat) 3321, 2966, 2866, 1690, 1527, 1365, 1172 cm$^{-1}$; $^1$H NMR (CDCl$_3$, 300 MHz) δ 1.17–1.27 (m, 1H), 1.34–1.46 (m, 2H), 1.44 (s, 9H), 1.59–1.68 (m, 2H), 1.61–1.93 (m, 1H), 2.00–2.09 (m, 1H), 2.55 (d, J=7.8 Hz, 1H), 2.62 (d, J=6.9 Hz, 1H), 3.93 (brs, 1H), 4.52 (brs, 1H).

Intermediate 16

1-(2-Chloroacetyl)pyrrolidine

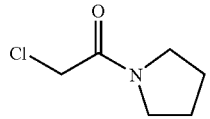

Chloroacetyl chloride (5.25 g, 46.46 mmol) was added to a stirred cooled (0° C.) solution of pyrrolidine (3.0 g, 42.25 mmol) and triethylamine (6.4 g, 63.36 mmol) in dry dichloromethane (50 ml) and the mixture was stirred at the same temperature for 1 h. The mixture was then diluted with dichloromethane (150 ml) and washed with water (2×200 ml), brine (200 ml) and dried (Na$_2$SO$_4$). The solvent was evaporated under reduced pressure to give a viscous residue. The residue was purified by silica gel column chromatography using 10% ethyl acetate in chloroform to give 2.35 g of the product as a white solid; IR (KBr) 3433, 2951,1657, 1641, 1444, 1281 cm$^{-1}$; $^1$H NMR (CDCl$_3$, 300 MHz) δ 1.89 (quint, J=5.7 Hz, 2H), 2.01 (quint, J=5.7 Hz, 2H), 3.51 (q, J=5.7 Hz, 4H), 4.02 (s, 2H).

Intermediate 17

1-(2-Chloroacetyl)thiazolidine

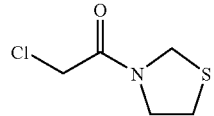

Reaction of thiazolidine (1.0 g, 11.23 mmol) with chloroacetyl chloride (1.4 g, 12.35 mmol) in the presence of triethylamine (1.7 g, 16.85 mmol) in dry dichloromethane (20 ml) as described in Intermediate 16 gave 1.1 g of the product as a semisolid; IR (neat) 3445, 2940, 1651, 1423, 1268 cm$^{-1}$; $^1$H NMR (CDCl$_3$, 300 MHz) δ 3.03 (t, J=6.3 Hz, 1H), 3.13 (t, J=6.3 Hz, 1H) 3.82–3.89 (m, 2H), 4.08 (d, J=6.9 Hz, 2H) 4.59 (d, J=6.9 Hz, 2H).

Intermediate 18

(2S)-1-(2-Chloroacetyl)-2-pyrrolidinecarbonitrile

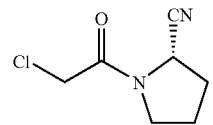

This intermediate was prepared from L-(−)-proline using a literature procedure (*J. Med. Chem.*, 2003, 46, 2774–2789).

Intermediate 19

(2S,4S)-1-(2-Chloroacetyl)-4-fluoropyrrolidine-2-carbonitrile

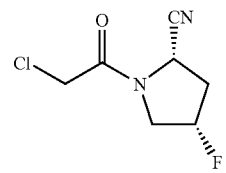

Step 1: (2S,4S)-N—BOC-4-fluoropyrrolidine-2-carboxamide: This intermediate was prepared in 5 steps from L-(−)-4-hydroxyproline using a literature procedure (WO 03/002553 A2)

Step 2: (2S,4S)-N—BOC-4-fluoropyrrolidine-2-carbonitrile: To a stirred and cooled (0° C.) solution of (2S,4S)-N—BOC-4-fluoropyrrolidine-2-carboxamide (10 g, 43.10 mmol) in dry THF (50 ml) was added triethylamine (13.93 g, 138 mmol) and trifluoroacetic anhydride (14.5 g, 69.05 mmol). The resulting clear solution was stirred at the same temperature for 1 h. The reaction was quenched with water (100 ml) and extracted with chloroform (2×100 ml). The combined organic extracts were washed with water (2×100 ml), brine (50 ml) and dried (Na$_2$SO$_4$). The solvent was evaporated under reduced pressure to give 9.0 g (97.6%) of the product as an off-white solid. IR (KBr) 2979, 2243, 1387, 1240, 1168, 1123, 1072, 960 cm$^{-1}$; $^1$H NMR (CDCl$_3$, 300 MHz) δ 1.49–1.53 (d, rotomer, 9H), 2.25–2.47 (m, 1H), 2.64 (t, J=14.7 Hz, 1H), 3.52 (dd, J=9.6, 3.6 Hz, 0.5H, rotomer), 3.64 (dd, J=9.3, 3.3 Hz, 0.5H, rotomer), 3.73–3.94 (m, 1H), 4.64 (d, J=8.7 Hz, 0.6H, rotomer), 4.76 (d, J=8.7 Hz, 0.4 H, rotomer), 5.31 (brd, J=51.3 Hz, 1H).

Step 3: (2S,4S)-4-fluoropyrrolidine-2-carbonitrile p-methylbenzenesulfonate: 4-Methyl-benzenesulfonic acid monohydrate (15.2 g, 79.91 mmol) was added to a solution of step 2 intermediate (8.5 g, 39.72 mmol) in acetonitrile (170 ml) and the mixture was stirred at room temperature for 48 h. The solvent was then evaporated under reduced pressure to afford a brown residue which was taken up in dry diethyl ether (200 ml) and stirred for 1 h. The white crystalline product separated out was collected by filtration and dried under vacuum to give 10.5 g (87%) of the product as a pale pink solid. IR (KBr) 3304, 2927, 2249, 1393, 1167, 1123, 1034, 1010 cm$^{-1}$; $^1$H NMR (CDCl$_3$, 300 MHz) δ 2.31 (s, 3H), 2.37–2.65 (m, 2H), 3.76–3.87 (m, 2H), 5.10 (brs, 2H), 5.33 (brd, J=51.6 Hz, 1H), 7.19 (d, J=8.1 Hz, 2H), 7.75 (d, J=8.1 Hz, 2H).

Step 4: (2S,4S)-1-(2-Chloroacetyl)-4-fluoropyrrolidine-2-carbonitrile: A solution of step 3 intermediate (10 g, 32.89 mmol ) and triethylamine (4.32 g, 42.77 mmol) in dichloromethane (200 ml) was added drop wise to a stirred and cooled (0° C.) solution of chloroacetyl chloride (4.81 g, 32.95 mmol) in dichloromethane (50 ml) over a period of 10 min. The mixture was stirred at the same temperature for 2 h and diluted with dichloromethane (100 ml) and water (100 ml) under stirring. The layers were separated. The organic layer was washed with water (2×50 ml), brine (50 ml) and dried ($Na_2SO_4$). The residue obtained after evaporation of the solvent was triturated with diethyl ether to give 5.89 g (94%) of the product as an off-white solid, IR (KBr) 2924, 2241, 1678, 1407, 1281, 1225, 1076, 1051, 958 $cm^{-1}$; $^1H$ NMR ($CDCl_3$, 300 MHz) δ 2.26–2.48 (m, 1H), 2.66–2.80 (m, 1H), 4.06 (s, 2H), 3.81–4.29 (m, 2H), 4.95 (d, J=9.6 Hz, 0.8H, rotomer), 5.38 (brd, J=51.3 Hz, 0.2H, rotomer) 5.46 (d, J=9.0 Hz, 0.2H, rotomer), 5.46 (dt, J=44.4, 3.3 Hz, 0.8H, rotomer).

Intermediate 20

(4S)-3-(2-Chloroacetyl)-1,3-thiazolane-4-carbonitrile

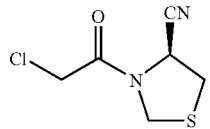

Step 1: (4S)-1,3-thiazolane-4-carboxylic acid: This intermediate was prepared from L-cysteine hydrochloride using a literature procedure (*J. Am. Chem. Soc,* 1937, 59, 200–206)

Step 2: (4S)-N—BOC-1,3-thiazolane-4-carboxylic acid: A solution of di-tert-butyl dicarbonate (21.3 g, 0.977 mol) in acetonitrile (20 ml) was added to a stirred solution of Step 1 intermediate (10.0 g, 0.075 mol) and triethylamine (18.98 g, 0.188 mol) in 50% aqueous acetonitile (100 ml) and the solution was stirred at room temperature for 18 h. Acetonitrile was evaporated under reduced pressure and the residual aqueous solution was acidified with 1N HCl to pH 3–4. The solution was extracted with dichloromethane (2×100 ml) and the combined organic extracts were washed with water (2×100 ml), brine (100 ml) and dried ($Na_2SO_4$). The residue obtained after evaporation of the solvent was triturated with n-pentane to give 17.5 g of the product as a white solid. IR (KBr) 1746, 1634, 1417, 1367, 1309, 1216, 1119, 1142, 894 $cm^{-1}$; $^1H$ NMR ($CDCl_3$, 300 MHz) δ 1.48 (s, 9H), 3.24–3.33 (m, 2H), 4.42–4.84 (m, 3H), 5.26 (brs, 1H).

Step 3: (4S)-N—BOC-1,3-thiazolane-4-carboxamide: To a stirred and cooled (−15° C.) solution of step 2 intermediate (10 g, 42.918 mmol) and triethylamine (7.15 g, 70.79 mmol) in dry tetrahydrofuran (100 ml) was added ethyl chloroformate (7.68 g, 70.79 mmol) under nitrogen atmosphere to result a white precipitate. The mixture was stirred at the same temperature for 30 min and 30% aqueous $NH_4OH$ (100 ml) solution was added drop-wise over a period of 20 min. The temperature of the reaction mixture was slowly raised to room temperature and stirring was continued for another 18 h. The mixture was then extracted into dichloromethane (2×100 ml) and the combined organic extracts were washed with water (100 ml), brine (100 ml) and dried ($Na_2SO_4$). The residue obtained after evaporation of the solvent was triturated with n-pentane (50 ml) to give 7.1 g (71%) of the product as a white solid. IR (KBr) 3406, 1666, 1405, 1365, 1163, 1109, $cm^{-1}$; $^1H$ NMR ($CDCl_3$, 300 MHz) δ 1.49 (s, 9H), 3.20–3.51(m (br), 2H), 4.51–4.54 (m, (br), 2H), 4.51–4.54 (m, br), 2H), 5.61 (m (br), 1H), 6.50 (s (br), 2H).

Step 4: (4S)-N—BOC-1,3-thiazolane-4-carbonitrile: To a stirred and cooled (0° C.) solution of step 3 intermediate (7.0 g, 30.04 mmol) and triethylamine (9.2 g, 91.09 mmol) in dry tetrahydrofuran (35 ml) was added trifluoroacetic anhydride (9.46 g, 45.05 mmol) and the mixture was stirred at the same temperature for 1h. The reaction mixture was diluted with water (50 ml) and extracted with chloroform (2×50 ml). The combined organic extracts were washed with water (2×100 ml), brine (50 ml) and dried ($Na_2SO_4$). The solvent was evaporated under reduced pressure to give 5.98 g (92.6%) of the product as a white solid. IR (KBr) 2988, 2243, 1693, 1368, 1271, 1166, 1142, 1113, 970 $cm^{-1}$; $^1H$ NMR ($CDCl_3$, 300 MHz) δ 1.51 (s, 9H), 3.28 (m, 2H), 4.46 (m, 1H), 4.57 (d, J=9.0 Hz, 1H), 4.87 (m, 0.5H), 5.11 (m, 0.5H).

Step 5: (4S)-1,3-thiazolane-4-carbonitrile p-methylbenzenesulfonate: 4-Methylbenzene-sulfonic acid monohydrate (7.73 g, 40.68 mmol) was added to a stirred solution of step 4 intermediate (5.8 g, 27.10 mmol) in dry acetonitrile (50 ml) and the mixture was stirred at room temperature for 24 h under nitrogen atmosphere. The solvent was evaporated under reduced pressure and the oily residue obtained was triturated with dry diethyl ether (100 ml) to give 7.21 g (93%) of the product as a white crystalline solid. IR (KBr) 2988, 2243, 1693, 1368, 1271, 1166, 1142, 1113, 970 $cm^{-1}$; $^1H$ NMR ($CDCl_3$, 300 MHz) δ 2.37 (s, 3H), 3.33 (dd, J=9.0, 3.3 Hz, 1H), 3.46 (dd, J=6.0, 6.0 Hz, 1H), 4.51 (s, 2H), 5.27–5.30 (m, 1H), 6.15 (brs, 2H), 7.20 (d, J=8.1 Hz, 2H), 7.76 (d, J=8.1 Hz, 2H).

Step 6: (4S)-3-(2-Chloroacetyl)-1,3-thiazolane-4-carbonitrile: A mixture of step 5 intermediate (7.0 g, 23.03 mmol) and triethylamine (3.02 g, 29.90 mmol) in dry dichloromethane (25 ml) was added drop wise (10 min) to a stirred and cooled (0° C.) solution of chloroacetyl chloride (2.58 g, 23.03 mmol) in dry dichloromethane (25 ml) over 20 min. The resulting mixture was stirred at 0° C. for 2 h and diluted with water (100 ml). The organic layer was separated, washed with water (2×50 ml), brine (50 ml) and dried ($Na_2SO_4$). The solvent was evaporated under reduced pressure and the residue obtained was triturated with diethyl ether (30 ml) to give 4.01 g, (91%) of the product as a white solid. IR (KBr) 2953. 2246, 1667, 1393, 1284, 1262, 1182, 985 $cm^{-1}$; $^1H$ NMR ($CDCl_3$, 300 MHz) δ 3.32 (d, J=4.2 Hz, 2H), 4.13 (s, 2H), 4.67 (d, J=8.4 Hz, 1H), 4.73 (d, J=9.0 Hz, 1H), 5.27 (dd, J=3.6, 1.5 Hz, 1H).

Example 1 cis-(±)-6-(3-[2-(1-Pyrrolidinyl)-2-oxoethylamino] cyclopentylmethylamino)nicotino-nitrile

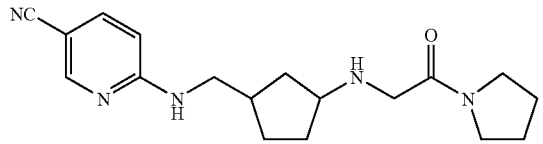

Step 1: cis-(±)-6-[3-N—BOC-Aminocyclopentylmethylamino]nicotinonitrile: A mixture of Intermediate 5 (5.0 g, 23.36 mmol), 6-chloronicotinonitrile (3.3 g, 23.82 mmol) and $KHCO_3$ (2.4 g, 24.0 mmol) in dry DMF (50 ml) was heated at 80° C. for 3 h under a nitrogen atmosphere. The mixture was cooled to room temperature and diluted with EtOAc (200 ml) and water (200 ml) under stirring. The layers were separated and the aqueous layer was extracted with EtOAc (50 ml). The combined organic extracts were washed with water (3×100 ml), and brine (100 ml) and dried (Na2SO4). The solvent was evaporated under reduced pressure and the residue obtained was purified by silica gel column chromatography (20% EtOAc in CHCl$_3$) to give 6.0 g (81%) of the product as a white solid; IR (neat) 3355, 2972, 2216, 1693, 1607, 1518, 1393, 1366, 1299, 1249, 1169, 1077, 1012 cm$^{-1}$; $^1$H NMR (CDCl$_3$, 300 MHz) δ 1.11–1.16 (m, 1H), 1.37–1.56 (m, 2H), 1.44 (s, 9H), 1.81–1.87 (m, 1H), 1.99–2.05 (m, 1H), 2.17–2.29 (m, 2H), 3.28–3.39 (m, 2H), 3.95 (brs, 1H), 6.38 (d, J=9.0 Hz, 1H), 7.58 (d, J=9.0 Hz, 1H), 8.40 (s, 1H).

Step 2: cis-(±)-6-[3-Aminocyclopentylmethylamino] nicotinonitrile: A solution of 12% HCl in EtOAc (20 ml) was added to Step 1 intermediate (1.0 g, 3.16 mmol) at 10° C. and the solution was maintained at the same temperature for 15 min under a nitrogen atmosphere. The solution was diluted with water (20 ml) and the layers were separated. The aqueous layer containing the product was basified to pH 10 with solid K$_2$CO$_3$ and the solution was extracted with DCM (4×50 ml). The combined organic layers were dried (Na$_2$SO$_4$) and concentrated under reduced pressure to give 683 mg of the amine, which was used as such for the next reaction.

Step 3: cis-(±)-6-(3-[2-(1-Pyrrolidinyl)-2-oxoethylamino] cyclopentylmethylamino)-nicotinonitrile: A solution of intermediate 16 (232 mg, 1.57) in dry THF (10 ml) was added (2 h) to a stirred and cooled (10° C.) mixture of the amine from Step 2 (680 mg, 3.15 mmol), K$_2$CO$_3$ (435 mg, 3.15 mmol) and NaI (236 mg, 1.57 mmol) in dry THF (20 ml) under a nitrogen atmosphere. The temperature of the reaction mixture was slowly raised to room temperature and the reaction mixture was stirred for 4 h. The mixture was filtered and the filtrate was concentrated under reduced pressure. The residue obtained was purified by silica gel column chromatography (3% methanol in chloroform) to give 300 mg (27%) of the product as a semisolid; IR (neat) 3299, 2951, 2213, 1633, 1607, 1518, 1442 cm$^{-1}$; $^1$H NMR (CDCl$_3$, 300 MHz) δ 1.40 (m, 1H), 1.59–1.79 (m, 4H), 1.82 (m, 9H), 2.52 (br s, 1H), 3.11–3.15 (m, 1H), 3.20–3.38 (m, 4H), 3.51 (t, J=6.9 Hz, 2H), 6.36 (d, J=9.0 Hz, 1H), 7.48 (d, J=8.7 Hz, 1H), 8.31 (s,1H).

Example 2

6-{(3-[2-Oxo-2-(1,3-thiazolan-3-yl)ethylamino] cyclopentylmethylamino}nicotino-nitrile

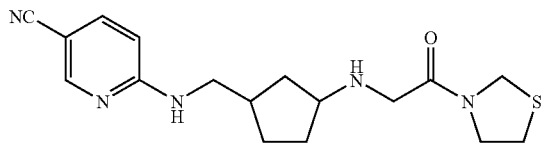

Reaction of cis-(±)-6-[(3-Aminocyclopentylmethylamino]nicotinonitrile (392 mg, 1.814 mmol) with Intermediate 17 (150 mg, 0.909 mmol) using potassium carbonate (500 mg, 3.629 mmol) and NaI (272 mg, 1.814 mmol) in THF (10 ml) as described in Example 1 gave 93 mg of the product as a semisolid; IR (neat) 3324, 2943, 2121, 1651, 1605, 1516, 1410 cm$^{-1}$; $^1$H NMR (CDCl$_3$, 300 MHz) δ 1.38 (m, 1H), 1.59–2.04 (m, 9H), 2.52 (brs, 1H), 3.04 (t, J=6.6 Hz, 1H), 3.11 (t, J=6.3 Hz, 1H), 3.14–3.49 (m, 4H), 3.66 (t, J=6.3 Hz, 1H), 3.89 (t, J=6.3 Hz, 1H), 4.42 (s, 1H), 4.63 (s, 1H), 6.35 (dd, J=6.3, 2.1 Hz, 1H), 7.34 (br s, 1H), 7.46 (d, J=8.7 Hz, 1H), 8.32 (d, J=1.8 Hz, 1H).

Example 3

6-((1SR,3RS)-3-{2-[(2S)-2-Cyanopyrrolidin-1-yl]-2-oxoethylamino}cyclopentyl-methylamino)nicotinonitrile

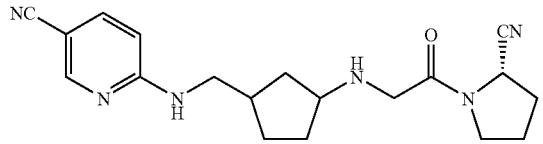

Reaction of cis-(±)-6-[3-Aminocyclopentylmethylamino] nicotinonitrile (680 mg, 3.15 mmol) with Intermediate 18 (272 mg, 1.57 mmol) using K$_2$CO$_3$ (435 mg, 3.15 mmol) and NaI (236 mg, 1.57 mmol) in dry THF (15 ml) as described in Example 1 gave 300 mg (27%) mg of the product as a semisolid: IR (neat) 3360, 2949, 2213, 1658, 1606, 1517, 1410, 1302, 1211, 1142 cm$^{-1}$; $^1$H NMR (CDCl$_3$, 300 MHz) δ 1.25–1.40 (m, 1H), 1.59–2.35 (m, 10H), 2.53 (brs, 1H), 3.16–2.59 (m, 7H), 4.19 (d, J=5.4 Hz, 0.8H, rotomer), 4.65 (dt, 0.2H, rotomer), 6.36 (d, J=9.0 Hz, 1H), 7.31 (brs, 1H, D$_2$O exchangeable), 7.48 (t, J=8.7 Hz, 1H), 8.31 (dd, J=4.5, 2.4 Hz, 1H).

Example 4

6-((1SR,3RS)-3-{2-[(2S)-2-Cyanopyrrolidin-1-yl]-2-oxoethylamino}cyclopentyl-methylamino)nicotinonitrile dihydrochloride

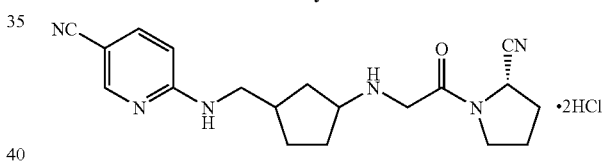

Dry HCl gas was bubbled into a solution of the free base (150 mg, 0.42 mmol) from Example 3 in dichloromethane (5 ml) at 10° C. The white solid precipitated out was allowed to stir at the same temperature for 15 min. The product was then collected by filtration, washed with dry diethyl ether (5 ml) and dried under vacuum for 3 h to give 152 mg of the product as a white solid: IR (KBr) 3435, 2946, 2236, 1664, 1616, 1434, 1342, 1206, cm$^{-1}$; $^1$H NMR (D$_2$O, 300 MHz) δ 1.35–1.57 (m, 2H), 1.74–1.94 (m, 2H), 2.08–2.21 (m, 3H), 2.22–2.43 (m, 4H), 3.41–3.47 (m, 3H), 3.56–3.69 (m, 2H), 4.02 (s, 2H), 4.80 (m, 1H, merged with HOD peak), 7.00 (d, J=9.6 Hz, 1H), 7.87 (d, J=8.1 Hz, 1H), 8.32 (s, 1H).

Example 5

6-((1SR,3RS)-3-{2-[(2S)-2-Cyanopyrrolidin-1-yl]-2-oxoethylamino}cyclopentyl-methylamino)nicotinonitrile maleate

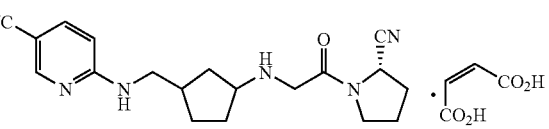

A solution of maleic acid (33 mg, 0.284 mmol) in acetone (3 ml) was added to a stirred solution of the free base (100 mg, 0.284 mmol) from Example 3 in acetone (3 ml) at room temperature. The mixture was stirred for 20 min and the solid separated out was collected by filtration. The product was dried under vacuum to give 130 mg (100%) of product as a white solid; IR (neat) 3421, 3247, 2978, 2217, 1669, 1606, 1580, 1447, 1352 1194 cm$^{-1}$; $^1$H NMR (D$_2$O, 300 MHz) δ 1.20–1.43 (m, 2H), 1.58–1.79 (m, 2H), 1.93–2.05 (m, 3H), 2.07–2.26 (m, 4H), 3.19 (d, J=6.3 Hz, 2H), 3.27–3.35 (m, 1H), 3.44–3.55 (m, 2H), 3.89 (s, 2H), 4.57–4.70 (m, rotomer, 1H), 6.12 (s, 2H), 6.43 (d, J=9.0 Hz, 1H), 7.47 (dd, J=7.2, 1.8 Hz, 1H), 8.10 (s, 1H).

Example 6

6-((1SR,3RS)-3-{2-[(2S)-2-Cyanopyrrolidin-1-yl]-2-oxoethylamino}cyclopentyl-methylamino)nicotinonitrile fumarate

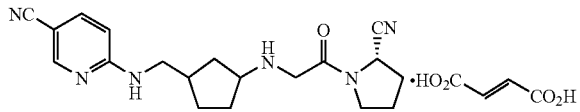

A solution of fumaric acid (33 mg, 0.284 mmol) in acetone (3 ml) was added to a stirred solution of base (100 mg, 0.284 mmol), from Example 3, in acetone (3 ml) at room temperature for 20 min. The solid precipitated out was collected by filtration and dried for 1 h under vacuum to give 130 mg of product as a white solid; IR (KBr) 3376, 2963, 2217, 1670, 1608, 1519, 1302, 1262 cm$^{-1}$; $^1$H NMR (D$_2$O, 300 MHz) δ 1.31–1.34 (m, 1H), 1.48–1.51 (m, 1H), 1.73–1.88 (m, 2H), 2.09–2.15 (m, 4H), 2.24–2.35 (m, 3H), 3.31 (d, J=6.0 Hz, 2H), 3.37–3.66 (m, 3H), 4.00 (s, 2H), 4.71–4.73 (m, 1H), 6.59–6.64 (m, 3H), 7.65 (d, J=9.0 Hz, 1H), 8.23 (s, 1H).

Example 7

6-((1SR,3RS)-3-{2-[(2S)-2-Cyanopyrrolidin-1-yl]-2-oxoethylamino}cyclopentyl-methylamino)nicotinonitrile citrate

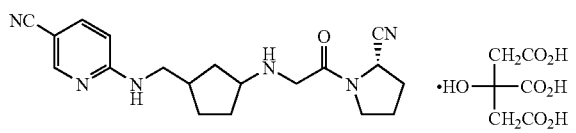

A solution of citric acid (55 mg, 0.284 mmol) in acetone (3 ml) was added to a stirred solution of base (100 mg, 0.284 mmol), from Example 3, in acetone (3 ml) at RT and stirred for 20 min at the same temperature. The solid precipitated out was collected by filtration and then dried for 1 h under vacuum to give 140 mg of the product as white solid: IR (KBr) 3384, 2963, 2218, 1667, 1609, 1519 1411 1213 cm$^{-1}$; $^1$H NMR (D$_2$O, 300 MHz) δ 1.20–1.40 (m, 2H), 1.60–1.77 (m, 2H), 1.88–2.05 (m, 3H), 2.07–2.26 (m, 4H), 2.75 (d, J=15.6 Hz, 2H), 2.70 (d, J=15.6 Hz, 2H), 3.20 (d, J=6 Hz, 2H), 3.27–3.55 (m, 3H), 3.89 (s, 2H), 4.57–4.70 (m, rotomer, 1H), 6.48 (d, J=9 Hz, 1H), 7.50 (dd, J=6.9, 2.1 Hz, 1H), 8.13 (d, J=1.2 Hz, 1H).

Example 8

6-((1S,3R)-3-{2-[(2S)-2-Cyanopyrrolidin-1-yl]-2-oxoethylamino}cyclopentylmethyl-amino)nicotinonitrile

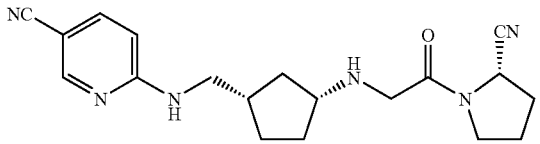

Step 1: 6-[(1S,3R)-3-N—BOC-Aminocyclopentylmethylamino]nicotinonitrile: This product was synthesized from Intermediate 9 (5.0 g, 23.36 mmol) and 6-chloronicotinonitrile (3.3 g, 23.82 mmol) using KHCO$_3$ (2.4 g, 24 mmol) in dry DMF (50 ml) as described in Example 1 to give 6.0 g (81%) of the product as a white solid: IR (KBr) 3359, 2968, 2216, 1680, 1607, 1521, 1171 cm$^{-1}$; $^1$H NMR (CDCl$_3$, 300 MHz) δ 1.11–1.15 (m, 1H), 1.38–1.55 (m, 2H), 1.44 (s, 9H), 1.82–1.87 (m, 1H), 1.99–2.05 (m, 1H), 2.17–2.28 (m, 2H), 3.30–3.38 (m, 2H), 3.96 (m, 1H), 4.75 (brs, 1H), 5.13 (brs, 1H), 6.38 (d, J=8.7 Hz, 1H), 7.56 (dd, J=6.6, 2.4 Hz, 1H), 8.35 (d, J=1.5 Hz, 1H).

Step 2: 6-[(1S,3R)-3-Aminocyclopentylmethylamino]nicotinonitrile: This product was prepared from Step 1 intermediate (1.0 g, 3.16 mmol) using a solution of 12% HCl in EtOAc (20 ml) as described in Example 1, step 2 to give 683 mg of the amine, which was used as such for next reaction.

Step 3: 6-((1S,3R)-3-{2-[(2S)-2-Cyanopyrrolidin-1-yl]-2-oxoethylamino}cyclopentyl-methyl-amino)nicotinonitrile: This product was synthesized from Step 2 intermediate (680 mg, 3.15 mmol) and Intermediate 18 (232 mg, 1.57) using K$_2$CO$_3$ (435 mg, 3.15 mmol) and NaI (236 mg, 1.57 mmol) in dry THF (20 ml) as described in Example 1 to give 300 mg (27%) of the product as a semisolid: IR (neat) 3359, 2926, 2214, 1658, 1606, 1518, 1410, 1302 cm$^{-1}$; $^1$H NMR (CDCl$_3$, 300 MHz) δ 1.34–1.41 (m, 1H), 1.59–1.91 (m, 5H), 1.97–2.36 (m, 5H), 2.51 (brs, 1H), 3.17–3.64 (m, 5H), 3.39 (d, J=6 Hz, 2H), 4.61–4.67 (m, rotomer, 0.15H), 4.76–4.80 (m, rotomer, 0.85H), 6.37 (d, J=9.0 Hz, 1H), 7.26 (brs, 1H), 7.46 (d, J=8.7 Hz, 1H), 8.30 (d, J=1.8 Hz, 1H).

Example 9

6-((1S,3R)-3-{2-[(2S)-2-Cyanopyrrolidin-1-yl]-2-oxoethylamino}cyclopentylmethyl-amino)nicotinonitrile dihydrochloride

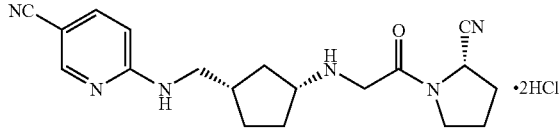

This dihydrochloride salt was synthesized from the base (150 mg, 0.42 mmol) from Example 8 using dry HCl gas as described in Example 4 to give 152 mg of the product as a white solid: IR (KBr) 3430, 2946, 2232, 1665, 1612, 1433, 1354, 1206 cm$^{-1}$; $^1$H NMR (D$_2$O, 300 MHz) δ 1.35–1.55 (m, 2H), 1.74–1.95 (m, 2H), 2.07–2.18 (m, 3H), 2.22–2.41 (m, 4H), 3.41–3.48 (m, 3H), 3.56–3.69 (m, 2H), 4.02 (s, 2H), 4.68 (m, 1H), 7.00 (d, J=9.6 Hz, 1H), 7.87 (d, J=9.0 Hz, 1H), 8.31 (d, J=1.5 Hz, 1H).

Example 10

6-((1R,3S)-3-{2-[(2S)-2-Cyanopyrrolidin-1-yl]-2-oxoethylamino}cyclopentylmethyl-amino)nicotinonitrile

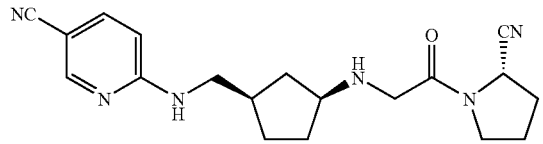

Step 1: 6-[(1R,3S)-3-N—BOC-Aminocyclopentylmethylamino]nicotinonitrile: This product was synthesized from Intermediate 13 (5.0 g, 23.36 mmol) and 6-chloronicotinonitrile (3.3 g, 23.82 mmol) using KHCO$_3$ (2.4 g, 24 mmol) in dry DMF (50 ml) as described in Example 1 to give 5.98 g (81%) of the product as a white solid; IR (neat) 3339, 2969, 2096, 1697, 1517, 1365, 1170 cm$^{-1}$; $^1$H NMR (CDCl$_3$, 300 MHz) δ 1.11–1.5 (m, 1H), 1.37–1.56 (m, 2H), 1.44 (s, 9H), 1.80–1.86 (m, 1H), 1.99–2.05 (m, 1H), 2.17–2.28 (m, 2H), 3.29–3.39 (m, 2H), 3.94 (brs, 1H), 4.74 (brs, 1H), 5.12 (brs, 1H), 6.37 (d, J=8.7 Hz, 1H), 7.55 (dd, J=6.6, 2.1 Hz, 1H), 8.55 (d, J=2.1 Hz, 1H).

Step 2: 6-[(1R,3S)-3-Aminocyclopentylmethylamino]nicotinonitrile: This product was prepared from Step 1 intermediate (1.0 g, 3.16 mmol) using 12% HCl in EtOAc (20 ml) as described in Example 1, step 2 to give 683 mg of the amine, which was used as such for next reaction.

Step 3: 6-((1R,3S)-3-{2-[(2S)-2-Cyanopyrrolidin-1-yl]-2-oxoethylamino}cyclopentyl-methylamino)nicotinonitrile: This product was synthesized from Step 2 intermediate (680 mg, 3.15 mmol) and Intermediate 18 (232 mg, 1.57) using K$_2$CO$_3$ (435 mg, 3.15 mmol) and NaI (236 mg, 1.57 mmol) in dry THF (20 ml) as described in Example 1, step 3 gave 300 mg (27%) of the product as a semisolid; IR (neat) 3359, 2947, 2215, 1659, 1608, 1516, 1410, 1302, 1211 cm$^{-1}$; $^1$H NMR (CDCl$_3$, 300 MHz) δ 1.40 (m, 1H), 1.59–1.79 (m, 4H), 1.82 (m, 9H), 2.52 (br s, 1H), 3.11–3.15 (m, 1H), 3.20–3.38 (m, 4H), 3.51 (t, J=6.9 Hz, 2H), 6.36 (d, J=9.0 Hz, 1H), 7.48 (d, J=8.7 Hz, 1H), 8.31 (s, 1H).

Example 11

6-((1R,3S)-3-{2-[(2S)-2-Cyanopyrrolidin-1-yl]-2-oxoethylamino}cyclopentyl-methylamino)nicotinonitrile dihydrochloride

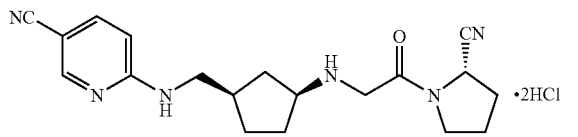

The base (150 mg, 0.42 mmol) from Example 7 in dichloromethane (5 mL) was treated with dry HCl gas as described in Example 4 to give 152 mg of the product as a white solid: IR (KBr) 3430, 2946, 2232, 1665, 1612, 1433, 1354, 1206 cm$^{-1}$; $^1$H NMR (D$_2$O, 300 MHz) δ 1.35–1.55 (m, 2H), 1.74–1.95 (m, 2H), 2.07–2.18 (m, 3H), 2.22–2.41 (m, 4H), 3.41–3.48 (m, 3H), 3.56–3.69 (m, 2H), 4.02 (s, 2H), 4.68 (m, 1H), 7.00 (d, J=9.6 Hz, 1H), 7.87 (d, J=9.0 Hz, 1H), 8.31 (d, J=1.5 Hz, 1H).

Example 12

6-((4SR,1RS)-4-{2-[(2S)-2-cyanopyrrolidin-1-yl]-2-oxoethylamino}-2-cyclopentenyl-methylamino)nicotinonitrile

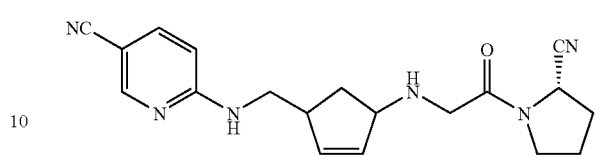

Step 1: cis-(±)-6-[4-N—BOC-Amino-2-cyclopentenylmethylamino]nicotinonitrile: This compound was prepared from Intermediate 14 (2.83 g, 8.96 mmol) and 6-chloronicotinonitrile (1.24 g, 8.96 mmol) using KHCO3 (1.41 g, 13.97 mmol) in dry DMF (20 ml) as described in Example 1 to give 1.1 g (40%) of the product as a solid; IR (neat) 3327, 2978, 2219, 1687, 1605, 1511, 1365, 1251, 1164, 1068 cm$^{-1}$; $^1$H NMR (CDCl$_3$, 300 MHz) δ 1.35–1.48 (m, 1H), 1.45 (s, 9H), 2.51–2.61 (m, 1H), 3.43 (t, J=4.8 Hz, 2H), 4.60 (dd, J=8.4, 6.3 Hz, 2H), 4.82 (brs, 1H), 5.64 (brs, 1H), 5.81 (s, 2H), 6.43 (d, J=8.7 Hz, 1H), 7.53 (dd, J=6.6, 2.1 Hz, 1H), 8.35 (d, J=2.1 Hz, 1H).

Step 2: cis-(±)-6-[4-Amino-2-cyclopentenylmethylamino]nicotinonitrile: The amine was prepared from Step 1 intermediate (1.0 g, 3.19 mmol) as described in Example 1, Step 2 to give 650 mg of the product, which was used as such for the next step.

Step 3: cis-(±)-6-((4SR,1RS)-4-{2-[(2S)-2-cyanopyrrolidin-1-yl]-2-oxoethylamino}-2-cyclopentenylmethylamino) nicotinonitrile: This compound was prepared by coupling reaction of free amine from Step 2 (650 mg, 3.00 mmol) with Intermediate 18 (274 mg, 1.58 mmol) using K$_2$CO$_3$ (437 mg, 3.15 mmol) and NaI (238 mg, 1.58 mmol) in dry THF (30 ml) as described in Example 1 to give 250 mg of the product as a viscous residue: IR (neat) 3313, 2953, 2214, 1655, 1518, 1412, 1301, 1212, 1145 cm$^{-1}$; $^1$H NMR (CDCl$_3$, 300 MHz) δ 1.53 (d, J=14.1 Hz, 1H), 2.13–2.45 (m, 4H), 3.14–3.65 (m, 8H), 3.79 (t, J=6.9 Hz, 1H), 4.56–4.58 (m, 0.2H, rotomer), 4.78 (d, J=5.7 Hz, 0.8H, rotomer), 5.84–5.89 (m, 2H), 6.40 (d, J=8.7 Hz, 1H), 7.44 (t, J=6.3 Hz, 1H), 7.56 (brs, 1H), 7.56 (brs, 1H), 8.31 (s, 1H).

Example 13

6-((1RS,3RS)-3-{2-[(2S)-2-Cyanopyrrolidin-1-yl]-2-oxoethylamino}cyclopentyl-methylamino)nicotinonitrile

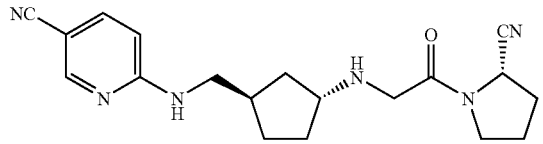

Step 1: trans-(±)-6-(3-N—BOC-Aminocyclopentylmethylamino)nicotinonitrile: This compound was prepared from Intermediate 15 (5.0 g, 23.36 mmol) and 6-chloronicotinonitrile (3.3 g, 23.82 mmol) as described in Example 1, Step 1 to give 6.0 g (81%) mg of the product as a white solid; IR (neat) 3340, 2972, 2222, 1682, 1602, 1515, 1364, 1295, 1169, 1135 cm$^{-1}$; $^1$H NMR (CDCl$_3$, 300 MHz) δ 1.23–1.46 (m, 2H), 1.45 (s, 9H), 1.67–1.72 (m, 2H), 1.89–1.99 (m, 1H), 2.04–2.11 (m, 1H), 2.29–2.40 (m, 1H), 3.27 (t, J=6.3 Hz, 2H), 3.59–4.03 (m, 1H), 4.49 (brs, 1H), 5.10 (brs, 1H), 6.36 (d, J=8.7 Hz, 1H), 7.56 (dd, J=6.9, 1.8 Hz, 1H), 8.35 (dd, J=4.5, 2.1, Hz, 1H).

Step 2: trans-(±)-6-(3-Aminocyclopentylmethylamino) nicotinonitrile: The free amine was generated from Step 1 intermediate (1.0 g, 3.18 mmol) as described in Example 1, Step 2 to give 671 mg of the amine as a viscous liquid which was used as such for the next step.

Step 3: 6-((1RS,3RS)-3-{2-[(2S)-2-cyanopyrrolidin-1-yl]-2-oxoethylamino}cyclopentyl-methylamino)nicotinonitrile: The amine from Step 2 (655 mg, 3.03 mmol) was coupled with Intermediate 18 (274 mg, 1.58 mmol) using K$_2$CO$_3$ (437 mg, 3.15 mmol) and NaI (238 mg, 1.58 mmol) in dry THF (30 ml) as described in Example 1, Step 3 to give 282 mg of the product as a viscous residue: IR (neat) 3360, 2949, 2213, 1658, 1606, 1517, 1410, 1302, 1211, 1142 cm$^{-1}$; $^1$H NMR (CDCl$_3$, 300 MHz) δ 1.25–1.40 (m, 1H), 1.59–2.35 (m, 10H), 2.53 (brs, 1H), 3.16–2.59 (m, 7H), 4.19 (d, J=5.4 Hz, 0.8H, rotomer), 4.65 (dt, 0.2H, rotomer), 6.36 (d, J=9.0 Hz, 1H), 7.31 (brs, 1H, D$_2$O exchangeable), 7.48 (t, J=8.7 Hz, 1H), 8.31 (dd, J=4.5, 2.4 Hz, 1H).

Example 14

6-((1SR,3RS)-3-{2-[(2S,4S)-2-Cyano-4-fluoropyrrolidin-1-yl]-2-oxoethylamino}-cyclopentylmethylamino)nicotinonitrile

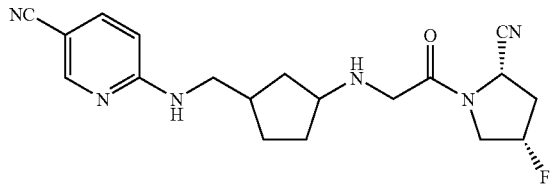

This compound was prepared from cis-(±)-6-(3-Aminocyclopentylmethylamino)-nicotinonitrile (680 mg, 3.15 mmol) and Intermediate 19 (300 mg, 1.57 mmol) using K$_2$CO$_3$ (435 mg, 3.15 mmol) and NaI (236 mg, 1.57 mmol) in dry THF (30 ml) as described in Example 1, Step 3 to give 275 mg (26%) of the product as a semisolid: IR (KBr) 3378, 2948, 2214, 1654, 1608, 1412, 1301, 1226, 1077 cm$^{-1}$; $^1$H NMR (CDCl$_3$, 300 MHz) δ 1.33–1.39 (m, 1H), 1.59–1.90 (m, 6H), 1.97–2.08 (m, 1H), 2.20–2.52 (m, 2H), 2.71 (t, J=45.6 Hz, 1H), 3.17–3.97 (m, 6H), 4.85 (m, 0.25H, rotomer), 4.97 (d, rotomer, J=9.0 Hz, 0.75H), 5.38 (d, rotomer, J=50.0 Hz, 0.25H), 5.44 (d, rotomer, J=50.0 Hz, 0.75H), 6.35 (d, J=9.0 Hz, 1H), 7.11 (brs, 1H), 7.45 (t, J=8.7 Hz, 1H), 8.30 (dd, J=8.1, 2.4 Hz, 1 H).

Example 15

6-((1S,3R)-3-{2-[(2S,4S)-2-Cyano-4-fluoropyrrolidin-1-yl]-2-oxoethylamino}cyclo-pentylmethylamino)nicotinonitrile

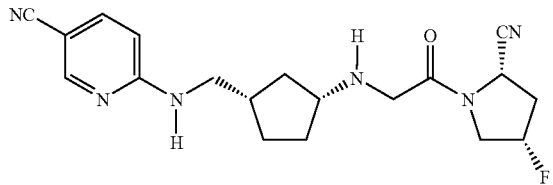

This compound was prepared from 6-[(1S,3R)-3-Aminocyclopentylmethylamino]-nicotinonitrile (680 mg, 3.15 mmol) from Example 8, Step 2 and Intermediate 19 (300 mg, 1.57 mmol) using K$_2$CO$_3$ (435 mg, 3.15 mmol) and NaI (236 mg, 1.57 mmol) in dry THF (30 ml) as described in Example 1 to give 275 mg (26%) of the product as a semi solid: IR (KBr) 3378, 2948, 2214, 1654, 1608, 1412, 1301, 1226, 1077 cm$^{-1}$; $^1$H NMR (CDCl$_3$, 300 MHz) δ 1.33–1.39 (m, 1H), 1.59–1.90 (m, 6H), 1.97–2.08 (m, 1H), 2.20–2.52 (m, 2H), 2.71 (t, J=45.6 Hz, 1H), 3.17–3.97 (m, 6H), 4.85 (m, 0.25H, rotomer), 4.97 (d, rotomer, J=9.0 Hz, 0.75H), 5.38 (d, rotomer, J=50.0 Hz, 0.25H), 5.44 (d, rotomer, J=50.0 Hz, 0.75H), 6.35 (d, J=9.0 Hz, 1H), 7.11 (brs, 1H), 7.45 (t, J=8.7 Hz, 1H), 8.30 (dd, J=8.1, 2.4 Hz, 1H).

Example 16

(4S)-3-{2-(1SR,3RS)-3-[(5-Cyano-2-pyridylaminomethyl)cyclopentylamino]acetyl}-1,3-thiazolane-4-carbonitrile dihydrochloride

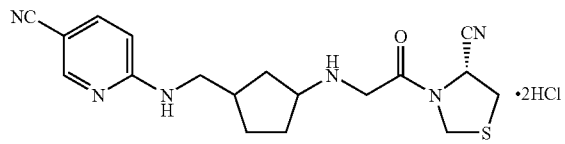

Step 1: (4S)-3-{2-(1SR,3RS)-3-[(5-Cyano-2-pyridylaminomethyl) cyclopentylamino]-acetyl}-1,3-thiazolane -4-carbonitrile: Reaction of cis-(±)-6-(3-Aminocyclopentylmethyl-amino)nicotinonitrile (680 mg, 3.15 mmol) with Intermediate 20 (300 mg, 1.58 mmol) using K$_2$CO$_3$ (435 mg, 3.15 mmol) and NaI (236 mg, 1.57 mmol) in dry THF (30 ml) as described in Example 1, Step 3 gave 276 mg of the product as a white solid: IR (KBr) 3366, 2943, 2213, 1664, 1607, 1517, 1405, 1302, 1211 cm$^{-1}$; $^1$H NMR (CDCl$_3$, 300 MHz) δ 1.33 (m, 1H), 1.60–2.09 (m, 7H), 2.50 (m, 1H), 3.18–3.56 (m, 6H), 4.54–4.60 (m, 2H), 5.31 (dd, J=4.8, 4.5 Hz, 1H), 6.35 (dd, J=5.7, 3.3 Hz, 1H), 6.91 (brs, 1H), 7.52 (m, 1H), 8.32 (d, J=8.1 Hz, 1H).

Step 2: (4S)-3-{2-(1SR,3RS)-3-[(5-Cyano-2-pyridylaminomethyl)cyclopentylamino]-acetyl}-1,3-thiazolane-4-carbonitrile dihydrochloride: The dihydrochloride salt was prepared form Step 1 intermediate (50 mg) using dry HCl gas in dichloromethane as described in Example 4 gave 52 mg of the product as a white solid: IR (KBr) 3429, 2938, 2237, 1666, 1616, 1426, 1342, 1208 cm$^{-1}$; $^1$H NMR (D$_2$O, 300 MHz) δ 1.33–1.53 (m, 2H), 1.74–1.93 (m, 2H), 2.08–2.15 (m, 1H), 2.29–2.40 (m, 2H), 3.34–3.41 (m, 4H), 3.63–3.68 (m, 1H), 4.03–4.18 (m, 2H), 4.51 (d, J=8.7 Hz, 1H), 4.61 (d, J=8.7 Hz, 1H), 5.22–5.25 (m, 1H), 6.98 (d, J=9.6 Hz, 1H), 7.86 (d, J=9.3 Hz, 1H), 8.29 (d, J=1.5 Hz, 1H).

Example 17

(4S)-3-{2-(1RS,3RS)-3-[(5-Cyano-2-pyridylaminomethyl)cyclopentylamino]acetyl}-1,3-thiazolane-4-carbonitrile dihydrochloride

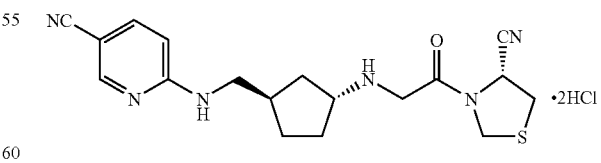

Step 1: (4S)-3-{2-(1RS,3RS)-3-[(5-Cyano-2-pyridylaminomethyl)cyclopentylamino]-acetyl}-1,3-thiazolane-4-carbonitrile: This compound was prepared from trans-(±)-6-(3-Aminocyclopentylmethylamino)nicotinonitrile from Example 13, Step 2 (680 mg, 3.15 mmol) and Intermediate 20 (300 mg, 1.58 mmol) using K$_2$CO$_3$ (435 mg, 3.15 mmol)

and NaI (236 mg, 1.57 mmol) in dry THF (30 ml) as described in Example 1, step 3 to give 270 mg of the product as a white solid: IR (KBr) 3414, 2935, 2214, 1666, 1607, 1401, 1303 cm$^{-1}$; $^1$H NMR (CDCl$_3$, 300 MHz) δ 1.26–1.36 (m, 1H), 1.39–1.80 (m, 4H), 1.93–2.03 (m, 2H), 2.38–2.46 (m, 1H), 3.19–3.54 (m, 5H), 3.45 (s, 2H), 4.55–4.68 (m, 2H), 5.10 (br s, 1H), 5.31 (br s, 1H), 6.37 (d. J=9.0 Hz, 1H), 7.56 (dd, J=6.6, 2.1 Hz, 1H), 8.35 (d, J=2.1 Hz, 1H)

Step 2: (4S)-3-{2-(IRS,3RS)-3-[(5-Cyano-2-pyridylaminomethyl)cyclopentylamino]-acetyl}-1,3-thiazolane-4-carbonitrile dihydrochloride: The dihydrochloride salt was prepared form Step 1intermediate (50 mg) using dry HCl gas in dichloromethane (5 ml) as described in Example 4 to give 53 mg of the product as a white solid: Mp. 228–232° C.; IR (KBr) 3414, 2963, 2236, 1663, 1614, 1412 cm$^{-1}$; $^1$H NMR (D$_2$O, 300 MHz) 1.29–1.42 (m, 1H), 1.61–1.74 (m, 1H), 1.83–2.02 (m, 4H), 2.18–2.24 (m, 1H), 2.42–2.58 (m, 1H), 3.27–3.41 (m, 5H), 3.70–3.75 (m, 1H), 4.03–4.17 (m, 2H), 5.22–5.25 (m, 1H), 6.06 (d, J=9.3 Hz, 1H), 7.85 (d, J=9.3 Hz, 1H), 8.30 (dd, J=0.9 Hz, 1.2 Hz, 1H).

Example 18

(2S)-1-{2-[(3SR,1RS)-3-(2-Pyrimidinylaminomethyl)cyclopentylamino)acetyl}-pyrrolidine-2-carbonitrile

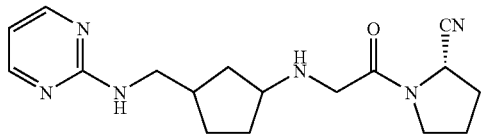

Step 1: cis-(±)-1-BOC-3-(2-pyrimidinylaminomethyl)cyclopentan-1-amine: A mixture of Intermediate 5 (2.0 g, 9.34 mmol), 2-chloropyrimidine (1.07 g, 9.34 mmol) and KHCO$_3$ (1.41 g, 13.974 mmol) in dry DMF (20 ml) was stirred at 80° C. for 18 h under nitrogen atmosphere. The reaction mixture was worked-up as described in Example 1, Step 1 to afford a viscous residue, which was purified by silica gel column chromatography (10% acetone in petroleum ether) to give 1.4 g of the product as a white solid: IR (KBr) 3369, 3260, 1682, 1599, 1525, 1453, 1366, 1170 cm$^{-1}$; $^1$H NMR (CDCl$_3$, 300 MHz) δ 1.12–1.21 (m, 1H), 1.37–1.56 (m, 2H), 1.44 (s, 9H), 1.75–1.85 (m, 1H), 1.98–2.04 (m, 1H), 2.15–2.75 (m, 2H), 3.29–3.50 (m, 2H), 3.96 (brs, 1H), 4.99 (brs, 1H), 5.19 (brs, 1H), 6.52 (t, J=4.8 Hz, 1H), 8.27 (d, J=4.8 Hz, 2H).

Step 2: cis-(±)-3-(2-pyrimidinylaminomethyl)cyclopentan-1-amine: This compound was prepared from Step 1 intermediate (1.3 g) as described in Example 1, Step 2 to give 890 mg of the product as a semisolid, which was used as such for the next step.

Step 3: (2S)-1-{2-[(3SR,1RS)-3-(2-Pyrimidinylaminomethyl)cyclopentylamino)acetyl}-pyrrolidine-2-carbonitrile: This compound was prepared from Intermediate 18 (373 mg, 2.16 mmol) and Step 2 intermediate (830 mg, 4.32 mmol) using K$_2$CO$_3$ (597 mg, 4.32 mmol) and NaI (324 mg, 2.16 mmol) in dry THF (30 ml) as described in Example 1, step 3 to give 300 mg of the product as a semisolid: IR (neat) 3307, 2949, 2240, 1659, 1589, 1535, 1414, 1367 cm$^{-1}$; $^1$H NMR (CDCl$_3$, 300 MHz) δ 1.17–1.26 (m, 1H), 1.54–1.60 (m, 2H), 1.77–1.84 (m, 2H), 1.90 (brs, 2H), 2.04–2.33 (m, 5H), 3.12–3.16 (m, 1H), 3.31–3.59 (m, 6H), 4.75–4.79 (m, 1H), 5.89 (brs, 1H), 6.48 (t, J=4.8 Hz, 1H), 8.25 (d, J=4.8 Hz, 2H).

Example 19

(2S)-1-{2-[(3SR,1RS)-3-(2-Pyrimidinylaminomethyl)cyclopentylamino)acetyl}-pyrrolidine-2-carbonitrile dihydrochloride

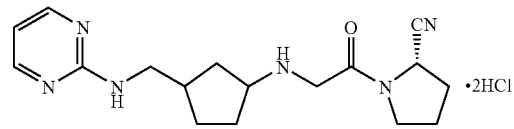

The dihydrochloride salt was prepared from the base (50 mg) from Example 18 using dry HCl gas in dichloromethane as described in Example 4 to give 55 mg of the product as a white solid: IR (KBr) 3426, 2960, 1648, 1430, 1346 cm$^{-1}$; $^1$H NMR (D$_2$O, 300 MHz) δ 1.34–1.53 (m, 2H), 1.72–1.90 (m, 2H), 2.00–2.38 (m, 7H), 3.38–3.67 (m, 4H), 4.01 (s, 3H), 4.67–4.82 (m, 1H), 6.93 (t, J=5.4 Hz, 1H), 8.46 (d, J=4.5 Hz, 2H).

Example 20

(2S)-1-{2-[(3S,1R)-3-(2-Pyrimidinylaminomethyl)cyclopentylamino)acetyl}-pyrrolidine-2-carbonitrile

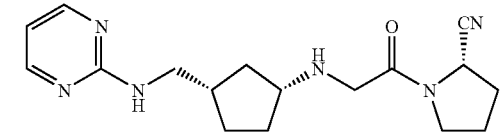

Step 1: N1-BOC-(3S,1R)-3-(2-pyrimidinylaminomethyl)cyclopentan-1-amine: This intermediate was prepared from Intermediate 9 (2.0 g, 9.34 mmol) and 2-chloropyrimidine (1.07 g, 9.34 mmol) in the presence of KHCO$_3$ (1.41 g, 13.974 mmol) in dry DMF (20 ml) as described in Example 18 to give 1.4 g of the product as a white solid: IR (KBr) 3362, 2959, 1680, 1602, 1524, 1253, 1170 cm$^{-1}$; $^1$H NMR (CDCl$_3$, 300 MHz) δ 1.12–1.21 (m, 1H), 1.37–1.56 (m, 2H), 1.44 (s, 9H), 1.75–1.85 (m, 1H), 1.98–2.04 (m, 1H), 2.15–2.75 (m, 2H), 3.29–3.50 (m, 2H), 3.96 (brs, 1H), 4.99 (brs, 1H), 5.19 (brs, 1H), 6.52 (t, J=4.8 Hz, 1H), 8.27 (d, J=4.8 Hz, 2H).

Step 2: (3S,1R)-3-(2-pyrimidinylaminomethyl)cyclopentan-1-amine: This compound was prepared from Step 1 intermediate (1.2 g) as described in Example 1, Step 2 to give 850 mg of the compound as a semisolid, which was used as such for the next step.

Step 3: (2S)-1-{2-[(3S,1R)-3-(2-Pyrimidinylaminomethyl)cyclopentylamino)acetyl}-pyrrolidine-2-carbonitrile: This compound was prepared from Step 2 intermediate (830 mg, 4.32 mmol) and Intermediate 18 (373 mg, 2.16 mmol) using K$_2$CO$_3$ (597 mg, 4.32 mmol) and NaI (324 mg, 2.16 mmol) in dry THF (30 ml) as described in Example 1, Step 3 to give 300 mg of the product as a semisolid: IR (neat) 3307, 2949, 2240, 1659, 1598, 1414, 1367 cm$^{-1}$; $^1$H NMR (CDCl$_3$, 300 MHz) δ 1.17–1.26 (m, 1H), 1.54–1.60 (m, 2H), 1.77–1.84 (m, 2H), 1.90 (brs, 2H), 2.04–2.33 (m, 5H), 3.12–3.16 (m, 1H), 3.31–3.59 (m, 6H), 4.75–4.79 (m, 1H), 5.89 (brs, 1H), 6.48 (t, J=4.8 Hz, 1H), 8.25 (d, J=4.8 Hz, 2H).

Example 21

(2S)-1-{2–1(3R,1S)-3-(2-Pyrimidinylaminomethyl) cyclopentylamino]acetyl}-pyrrolidine-2-carbonitrile

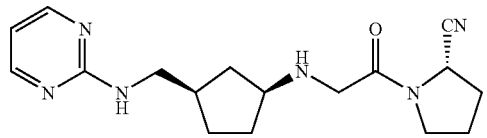

Step 1: N1-BOC-(3R,1S)-3-(2-pyrimidinylaminomethyl) cyclopentan-1-amine: This compound was prepared from Intermediate 13 (2 g, 9.34 mmol) and 2-chloropyrimidine (1.07 g, 9.34 mmol) using $KHCO_3$ (1.41 g, 13.97 mmol) in dry DMF (20 ml) as described in Example 18, to give 1.2 g of the product as a white solid: IR (KBr) 3362, 2959, 1680, 1602, 1524, 1253, 1170 $cm^{-1}$; $^1H$ NMR ($CDCl_3$, 300 MHz) δ 1.12–1.25 (m, 1H), 1.37–1.56 (m, 2H), 1.44 (s, 9H), 1.75–1.84 (m, 1H), 1.99–2.05 (m, 1H), 2.15–2.27 (m, 2H), 3.40 (m, 2H), 3.95 (brs, 1H), 4.99 (brs, 1H), 5.20 (brs, 1H), 6.52 (t, J=4.8 Hz, 1H), 8.27 (d, J=4.8 Hz, 2H).

Step 2: (3R,1s)-3-(2-pyrimidinylaminomethyl)cyclopentan-1-amine: This compound was prepared from Step 1 intermediate (800 mg) as described in Example 1, Step 2 to give 515 mg of the product as a semisolid, which was used as such for the next step. Step 3: (2S)1-{2-[(3R,1S)-3-(2-pyrimidinylaminomethyl)cyclopentylamino]acetyl}-pyrrolidine-2-carbonitrile: This compound was prepared from Step 2 intermediate (500 mg, 2.59 mmol) and Intermediate 18 (224 mg, 1.29 mmol) using $K_2CO_3$ (358 mg, 2.59 mmol) and NaI (194 mg, 1.29 mmol) in THF (30 ml) as described in the Example 1, Step 3 to gave 150 mg of the product as a semisolid: IR (neat) 3293, 2962, 2241, 1657, 1589, 1534, 1411, 1367 $cm^{-1}$; $^1H$ NMR ($CDCl_3$, 300 MHz) δ 1.18–1.27 (m, 1H), 1.52–1.61 (m, 2H), 1.78–1.88 (m, 2H), 1.96–2.35 (m, 7H), 3.13–3.17 (m, 1H), 3.32–3.60 (m, 6H), 4.77–4.80 (m, 1H), 5.92 (brs, 1H), 6.48 (t, J=4.8 Hz, 1H), 8.24 (d, J=4.8 Hz, 2H).

Example 22

(2S)-1-{2-[(3S,1R)-3-(1-Phenyl-1H-1,2,3,4-tetraazol-5-ylaminomethyl)cyclopentyl-amino]acetyl}-pyrrolidine-2-carbonitrile

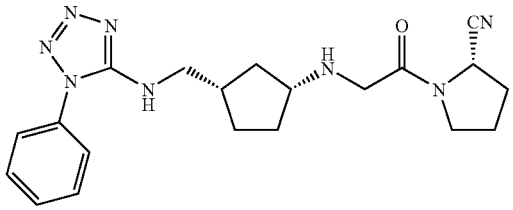

Step 1: N1-BOC-(3S,1R)-3-(1-Phenyl-1H-1,2,3,4-tetraazol-5-ylaminomethyl)-cyclopentan-1-amine: This compound was prepared by the reaction of Intermediate 9 (2.0 g, 9.34 mmol) with 2-chlorophenyltetrazole (1.86 g, 10.30 mmol) in the presence of $K_2CO_3$ (1.55 g, 11.23 mmol) in dry DMF (20 ml) at room temperature for 12 h. The reaction mixture was worked up as described in Example 1, Step 1 to give 1.2 g of the product as white solid: IR (KBr) 3337, 2965, 1682, 1614, 1529, 1252, 1175 $cm^{-1}$; $^1H$ NMR ($CDCl_3$, 300 MHz) δ 1.06–1.12 (m, 1H), 1.36–1.52 (m, 2H), 1.43 (s, 9H), 1.74–1.84 (m, 1H), 1.93–2.06 (m, 1H), 2.17–2.29 (m, 2H), 3.45–3.51 (m, 2H), 3.92 (brs, 1H), 4.36 (brs, 1H), 4.57 (brs, 1H), 7.49–7.63 (m, 5H).

Step 2: (3S,1R)-3-(1-Phenyl-1H-1,2,3,4-tetraazol-5-ylaminomethyl)cyclopentan-1-amine: To a stirred and cooled (10° C.) solution of Step 1 intermediate (500 mg, 1.396 mmol) in dry dichloromethane (3 ml) was added trifluoroacetic acid (3 ml) and the mixture was stirred for 30 min at 10° C. under nitrogen atmosphere. The mixture was evaporated under reduced pressure to give 519 mg of the product as its TFA salt which was used as such for the next step.

Step 3: (2S)-1-{2-[(3S,1R)-3-(1-Phenyl-1H-1,2,3,4-tetraazol-5-ylaminomethyl)cyclo-pentylamino]acetyl}-pyrrolidine-2-carbonitrile: This compound was prepared form Step 2 intermediate (519, 1.396 mmol) and Intermediate 18 (120 mg, 0.695 mmol) using $K_2CO_3$ (578 mg, 4.188 mmol) and NaI (104 mg, 0.695 mmol) in dry THF (30 ml) as described in Example 1, step3 to give (100 mg) of the product as a semisolid: IR (neat) 3306, 2953, 2242, 1659, 1609, 1503, 1410, 1216 $cm^{-1}$; $^1H$ NMR ($CDCl_3$, 300 MHz) δ 1.27 (br d, J=13.5 Hz, 1H), 1.56–1.98 (m, 5H), 2.13–2.33 (m, 4H), 2.50 (d, J=16.8 Hz, 1H), 2.53–2.60 (m, 1H), 2.88 (d, J=16.8 Hz, 1H), 2.99–3.18 (m, 2H), 3.37–3.53 (m, 4H), 4.68 (br d, J=6 Hz, 1H), 7.03 (br s, 1H), 7.41–7.55 (m, 5H).

Example 23

(2S)-1-{2-[(3SR,1RS)-3-(3-Chloro-4-nitroanilinomethyl)cyclopentylamino]acetyl}-pyrrolidine-2-carbonitrile

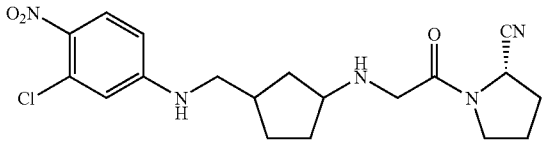

Step 1: cis-(±)-N1-BOC-3-(3-Chloro-4-nitroanilinomethyl)cyclopentan-1-amine: This compound was prepared from Intermediate 5 (2.0 g, 9.34 mmol) and 2,4-dichloronitrobenezene (1.79 g, 9.34 mmol) using $KHCO_3$ (1.40 mg, 14.00 mmol) in DMF (25 ml) as described in Example 1, Step 1 to give 1.0 g of the product as a yellow solid; IR (KBr) 3350, 2935, 1684, 1623, 1568, 1527, 1306, 1253, 1053 $cm^{-1}$; $^1H$ NMR ($CDCl_3$, 300 MHz) δ 1.125–1.17 (m, 1H), 1.44 (s, 9H), 1.47–1.56 (m, 2H), 1.92–2.07 (m, 2H), 2.30–2.41 (m, 2H), 3.22–3.26 (m, 2H), 3.98 (br s, 1H), 4.51 (br s, 1H), 6.61 (dd, J=6.9, 2.4 Hz, 1H), 6.81 (s, 1H), 8.12 (d, J=9.3 Hz, 1H), 8.16 (br s, 1H).

Step 2: cis-(±)-3-(3-Chloro-4-nitroanilinomethyl)cyclopentan-1-amine: This compound was prepared from Step 1 intermediate (600 mg, 1.65 mmol) as described in Example 1, Step 2 to give 470 mg of the amine as a yellow solid, which was used as such for the next step.

Step 3: (2S)-1-{2-[(3SR,1RS)-3-(3-chloro-4-nitroanilinomethyl)cyclopentylamino]-acetyl}-pyrrolidine-2-carbonitrile: This compound was prepared from Step 2 intermediate (469 mg, 1.74 mmol) and Intermediate 18 (150 mg, 0.869 mmol) using $K_2CO_3$ (240 mg, 1.71 mmol), NaI (130 mg, 086 mmol) and dry THF (30 ml) as described in Example 1, Step 3 to give 162 mg of the product as a semisolid: IR (neat) 3369, 2624, 1654, 1614, 1567, 1493, 1413, 1310, 1255 $cm^{-1}$; $^1H$ NMR ($CDCl_3$, 300 MHz) δ 1.18–1.31 (m, 2H), 1.56–1.61 (m, 2H), 1.87–1.91 (m, 3H), 2.13–2.37 (m, 5H), 3.21 (br s, 1H), 3.26 (t, J=5.1 Hz, 2H), 3.39 (s, 2H), 3.42–3.61 (m, 2H), 4.78 (br d, J=6.3 Hz, 1H), 6.59 (dd, J=6.9, 2.1 Hz, 1H), 6.83 (d, J=2.4 Hz, 1H), 8.10 (d, J=9.3 Hz, 1H), 8.18 (br s, 1H).

Example 24

(2S)-1-{2-[(3SR,1RS)-3-(2-Fluoro-4-nitroanilinomethyl)cyclopentylamino]acetyl}-pyrrolidine-2-carbonitrile

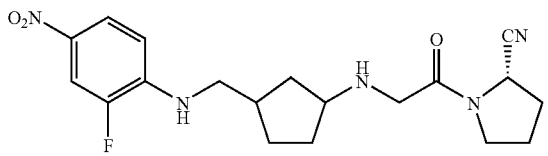

Step 1: cis-(±)-N1-BOC-3-(2-Fluoro-4-nitroanilinomethyl)cyclopentan-1-amine: This compound was prepared from Intermediate 5 (800 mg, 3.738 mmol) and 3,4-difluoronitrobenzene (600 mg, 3.738 mmol) using $KHCO_3$ (561 mg, 5.61 mmol) in DMF (10 ml) as described in Example 1, Step 1 to give 983 mg of the product as a yellow solid; IR (KBr) 3393, 2972, 1697, 1613, 1541, 1365, 1296 cm$^{-1}$; $^1$H NMR (CDCl$_3$, 300 MHz) δ 1.11–1.15 (m, 1H), 1.44 (s, 9H), 1.46–1.52 (m, 2H), 1.88–2.06 (m, 2H), 2.25–2.36 (m, 2H), 3.22 (t, J=5.4 Hz, 2H), 3.96 (brs, 1H), 4.56 (brs, 1H), 4.68 (brs, 1H), 6.62 (t, J=8.4 Hz, 1H), 7.88 (dd, J=9.0, 2.7 Hz, 1H), 8.00 (dd, J=6.6, 5.4 Hz, 1H).

Step 2: cis-(±)-3-(2-Fluoro-4-nitroanilinomethyl)cyclopentan-1-amine: This compound was prepared from Step 1 intermediate (900 mg, 2.535 mmol) as described in Example 1, Step 1 to give 500 mg of the product as a yellow solid.

Step 3: (2S)-1-{2-[(3SR,1RS)-3-(2-Fluoro-4-nitroanilinomethyl)cyclopentylamino]-acetyl}-pyrrolidine-2-carbonitrile: This compound was prepared from Step 2 intermediate (296 mg, 1.160 mmol) and Intermediate 18 (100 mg, 0579 mmol) using $K_2CO_3$ (161 mg, 1.607 mmol), NaI (87 mg, 0.58 mmol) in dry THF (30 ml) as described in Example 1, Step 3 to give 83 mg of the product as a yellow semisolid: IR (neat) 3355, 3195, 2947, 2240, 1659, 1630, 1547, 1324, 1196 cm$^{-1}$; $^1$H NMR (CDCl$_3$, 300 MHz) δ 1.40–1.44 (m, 1H), 1.64–2.05 (m, 6H), 2.17–2.21 (m, 4H), 2.61 (brs, 1H), 3.16–3.48 (m, 6H), 3.52–3.60 (m, 1H), 4.77–4.83 (m, 1H), 6.49–6.55 (m, 1H), 7.17 (brs, 1H), 7.82 (dt, J=9.3, 1.5 Hz, 1H), 7.98 (dd, J=26.6, 2.1 Hz, 1H).

Example 25

(2S)-1-{2-[(1R,3S)-3-(2-Fluoro-4-nitroanilinmethyl)cyclopentylamino]acetyl}-pyrrolidine-2-carbonitrile

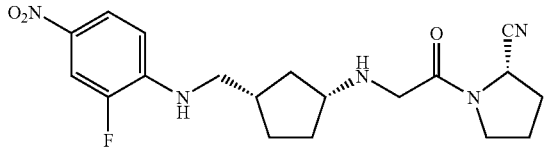

Step 1: N1-BOC-(3S,1R)-3-(2-fluoro-4-nitroanilinomethyl)cyclopentan-1-amine: This compound was prepared from Intermediate 9 (2.1 g, 9.813 mmol) and 3,4-difluoronitrobenzene (1.56 g, 9.813 mmol) using $KHCO_3$ (1.47 mg, 14.719) in DMF (20 ml) as described in Example 1, Step 1 to give 3.0 g of the compound as a yellow solid: IR (KBr) 3312, 2973, 1696, 1551, 1510, 1367, 1162 cm$^{-1}$; $^1$H NMR (CDCl$_3$, 300 MHz) δ 1.11–1.15 (m, 1H), 1.42–1.53 (m, 2H), 1.44 (s, 9H), 1.84–1.93 (m, 1H), 2.01–2.07 (m, 1H), 2.25–2.36 (m, 2H), 3.22 (t, J=6.6 Hz, 2H), 3.96 (m, 1H), 4.50 (brs, 1H), 4.67 (brs, 1H), 6.62 (t, J=8.7 Hz, 1H), 7.88 (dd, J=9.0, 2.7 Hz, 1H), 8.00 (d, J=9.0 Hz, 1H).

Step 2: (3S,1R)-3-(2-fluoro-4-nitroanilinomethy)cyclopentylamine: This compound was prepared from Step 1 intermediate (1.5 g) as described in Example 1, Step 2 to give 1.0 g of the product as a yellow solid, which was used as such for the next step.

Step 3: (2S)-1-{2-[(1R,3S)-3-(2-Fluoro-4-nitroanilinomethyl)cyclopentylamino]acetyl}-pyrrolidine-2-carbonitrile: This compound was prepared form Step 2 intermediate (900 mg, 3.55 mmol) and Intermediate 18 (306 mg, 1.77 mmol) using $K_2CO_3$ (981 mg, 7.108 mmol) and NaI (265 mg, 1.77 mmol) in dry THF (30 ml) as described in Example 1, Step 3 to give 250 mg of the compound as a yellow semisolid: IR (neat) 3315, 2931, 2240, 1659, 1613, 1546, 1408, 1325, 1196 cm$^{-1}$; $^1$H NMR (CDCl$_3$, 300 MHz) δ 1.43 (d, J=14.7 Hz, 1H), 1.64–1.78 (m, 4H), 1.84–2.04 (m, 2H), 2.15–2.36 (m, 4H), 2.63 (brs, 1H), 3.15–3.30 (m, 3H), 3.35–3.62 (m, 4H), 4.80–4.83 (m, 1H), 6.52 (t, J=8.4 Hz, 1H), 7.28 (brs, 1H), 7.80 (dd, J=9.3, 2.7 Hz, 1H), 7.98 (dd, J=6.6, 2.1 Hz, 1H).

Example 26

(2S,4S)-4-Fluoro-1-{2-[(1R,3S)-3-(2-fluoro-4-nitroanilinomethyl)cyclopentylamino]-ethyl}-pyrrolidine-2-carbonitrile

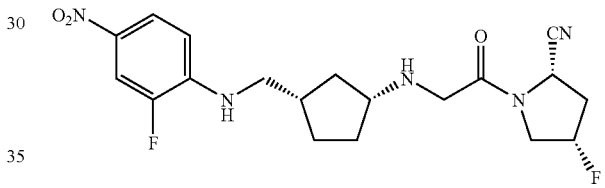

This compound was prepared form (3S,1R)-3-(2-fluoro-4-nitroanilinomethy)-cyclopentylamine (650 mg, 2.569 mmol) obtained from Example 25, Step 2 and Intermediate 19 (245 mg, 1.284 mmol) using $K_2CO_3$ (354 mg, 2.569 mmol) and NaI (385 mg, 2.569 mmol) in dry THF (30 ml) as described in Example 1, Step 3 to give 210 mg of the compound as a yellow solid: IR (KBr) 3392, 3315, 2959, 2243, 1653, 1616, 1559, 1333, 1296 cm$^{-1}$; $^1$H NMR (CDCl$_3$, 300 MHz) δ 1.25–1.46 (m, 2H), 1.64–2.05 (m, 5H), 2.27–2.72 (m, 3H), 3.16–3.94 (m, 7H), 4.86 (d, J=8.7 Hz, rotomer, 0.23H), 5.00 (d, J=9.3 Hz, rotomer, 0.77H), 5.38 (dt, J=4.0, 45.0 Hz, rotomer, 0.23H), 5.43 (dt, J=3.6, 44.4 Hz, rotomer, 0.77H), 6.53 (t, J=9.0 Hz, 1H), 8.21 (brs, 1H), 7.79 (dd, J=9.6, 2.4 Hz, 1H), 7.97 (dd, J=6.6, 2.7 Hz, 1H).

Example 27

(2S)-1-{2-[(3SR,1RS)-3-(2,4,5-Trifluoroanilinomethyl)cyclopentylamino]acetyl}-pyrrolidine-2-carbonitrile

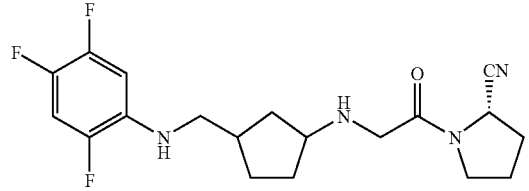

Step 1: cis-(±)-2,4,5-trifluoro1-[3-N—BOC-Aminocyclopentylcarboxamido]benzene: A solution of (±)-2-N—BOC-Azabicyclo[2,2,1]heptane-3-one (500 mg, 3.39 mmol) and 2,4,5-trifluoroaniline (1.07 g, 5.094 mmol) in DMF (10 ml) was added to a suspension of sodium hydride (122 mg, 5.09 mmol) in DMF (5 ml) at 0° C. under nitrogen atmosphere. The mixture was further stirred at the same temperature for 30 min. and then quenched with ice-cold water (50 ml). The mixture was extracted with EtOAc (2×50 ml) and washed with water (2×100 ml), brine (100 ml) and dried (Na$_2$SO$_4$). The solvent was evaporated under reduced pressure and the residue obtained was purified by silica gel column chromatography using 15% acetone in petroleum ether to give (725 mg) of the product as a white solid: IR (neat) 3434, 3304, 2967, 1677, 1539, 1429, 1211, 1021 cm$^{-1}$; $^1$H NMR (CDCl$_3$, 300 MHz) δ 1.44 (s, 9H), 1.52–2.06 (m, 5H), 2.19–2.28 (m, 1H), 2.78–2.85 (m, 1H), 4.11 (brs, 1H), 5.25 (m, 1H), 6.93–7.02 (m, 1H), 7.33 (s, 1H), 2.78–2.85 (m, 1H).

Step 2: cis-(±)-N1-BOC-3-(2,4,5-trifluoroanilinomethyl)cyclopentan-1-amine: Borane-methyl sulfide complex (1.34 ml, 13.95 mmol) was added to a stirred solution of Step 1 intermediate (1.0 g, 2.79 mmol) in dry THF (15 ml) at room temperature. The mixture was then heated at 60° C. for 30 min under nitrogen. The mixture was cooled to room temperature, diluted with water (50 ml) and then extracted with EtOAc (2×100 ml). The organic extract was washed with water (2×100 ml), brine (100 ml) and dried. The solvent was evaporated under reduced pressure and the residue was purified by silica gel column chromatography (10% acetone in petroleum ether) to give 600 mg of the product as a white solid: IR (neat) 3368, 2929, 1677, 1536, 1366, 1169 cm$^{-1}$; $^1$H NMR (CDCl$_3$, 300 MHz) δ 1.04–1.14 (m, 1H), 1.37–1.53 (m, 2H), 1.44 (s, 9H), 1.59 (brs, 1H), 1.89 (m, 1H), 1.98–2.04 (m, 1H), 2.19–2.33 (m, 2H), 3.03 (d, J=x Hz, 2H), 3.95 (brs, 1H), 4.49 (brs, 1H), 6.40–6.49 (m, 1H), 6.81–6.90 (m, 1H).

Step 3: cis-(±)-3-(2,4,5-trifluoroanilinomethyl)cyclopentan-1-amine: This compound was prepared from Step 2 intermediate (300 mg) as described in Example 1, Step 2 to give 190 mg of the compound as a yellow solid, which was used as such for the next step.

Step 4: (2S)-1-{2-[(3SR,1RS)-3-(2,4,5-Trifluoroanilinomethyl)cyclopentylamino]acetyl}-pyrrolidine-2-carbonitrile: Coupling reaction of Step 3 intermediate (185 mg, 0.788 mmol) with Intermediate 18 (65 mg, 0.379 mmol) using potassium carbonate (105 mg, 0.788 mmol) and NaI (113 mg, 0.788 mmol) in dry THF (10 ml) as described in Example 1, Step 3 to give 50 mg of the product as a semisolid: IR (neat) 3318, 2951, 2241, 1661, 1537, 1434, 1222, 1173 cm$^{-1}$; $^1$H NMR (CDCl$_3$, 300 MHz) δ 1.25–1.31 (m, 1H), 1.62–1.66 (m, 2H), 1.79–1.85 (m, 4H), 2.00–2.37 (m, 6H), 3.03 (d, J=6.0 Hz, 2H), 3.16 (t, J=5.1 Hz, 1H), 3.29–3.62 (m, 4H), 4.77–4.79 (m, 1H), 6.35–6.42 (m, 1H), 6.76–6.88 (m, 1H).

Example 28

(2S)-1-{2-[(3SR,1RS)-3-Phenylsulfanylmethylcyclopentylamino]acetyl}-pyrrolidine-2-carbonitrile

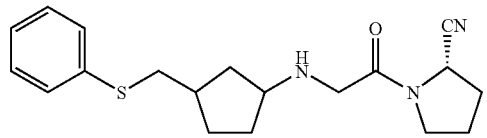

Step 1: cis-(±)-N1-BOC-3-phenylsulfanylmethylcyclopentan-1-amine: A mixture of Intermediate 4 (950 mg, 3.24 mmol), thiophenol (428 mg, 3.89 mmol) and K$_2$CO$_3$ (681 mg, 4.86 mmol) in dry DMF (20 ml) was stirred at 70° C. for 3 h under a nitrogen atmosphere. The mixture was cooled to room temperature, diluted with EtOAc (150 ml) and washed with water (2×100 ml), brine (100 ml) and dried (Na$_2$SO$_4$). The solvent was concentrated under reduced pressure to give 1.01 g of the product as a white solid: IR (KBr) 3399, 2963, 1687, 1515, 1175 cm$^{-1}$; $^1$H NMR (CDCl$_3$, 300 MHz) δ 1.06–1.16 (m, 1H), 1.43 (s, 9H), 1.46–1.51 (m, 2H), 1.81–1.98 (m, 2H), 2.11–2.19 (m, 1H), 2.22–2.35 (m, 1H), 2.95 (d, J=7.2 Hz, 2H), 3.09 (brs, 1H), 3.17 (brs, 1H), 7.14–7.34 (m, 5H).

Step 2: cis-(±)-3-phenylsulfanylmethylcyclopentan-1-amine: This compound was prepared from Step 1 intermediate (1.0 g) as described in Example 1, Step 2 to give 500 mg of the product as a semisolid, which was used as such for the next step.

Step 3: (2S)-1-{2-[(3SR,1RS)-3-phenylsulfanylmethylcyclopentylamino]acetyl}-pyrro-lidine-2-carbonitrile: This compound was prepared form Step 2 intermediate (396 mg, 1.913 mmol) and Intermediate 18 (165 mg, 0.956 mmol) using K$_2$CO$_3$ (264 mg, 1.91 mmol) and NaI (143 mg, 0.956 mmol) in dry THF (30 ml) as described in Example 1, Step 3 to give 147 mg of the product as a semisolid: IR (neat) 3316, 1947, 1661, 1412, 1313 cm$^{-1}$; $^1$H NMR (CDCl$_3$, 300 MHz) δ 1.15–1.29 (m, 1H), 1.52–1.56 (m, 2H), 1.84–1.85 (m, 2H), 2.01–2.32 (m, 7H), 2.98 (d, J=7.2 Hz, 2H), 3.09–3.14 (m, 1H), 3.37 (s, 2H), 3.39–3.62 (m, 2H), 4.74–4.77 (m, 1H), 7.13–7.33 (m, 5H).

Example 29

(2S)-1-{2–1(3SR,1RS)-3-Phenylsulfonylmethylcyclopentylamino]acetyl}-pyrrolidine-2-carbonitrile

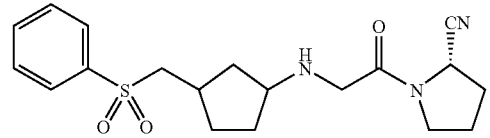

Step 1: cis-(±)-N1-BOC-3-phenylsulfonylmethylcyclopentan-1-amine: m-Chloro-perbenzoic acid (1.4 g, 4.06 mmol) was added to a well-stirred and cooled (10° C.) solution of N1-BOC-3-phenylsulfanylmethylcyclopentan-1-amine (500 mg, 1.62 mmol) from Example 28 in chloroform (25 ml) and the mixture was further stirred at the same temperature for 1 h. The excess m-chloroperbenzoic acid was quenched with aqueous sodium sulfite solution. The mixture was then diluted with chloroform (100 ml) and washed with 2N NaOH solution (2×50 ml), water (100 ml) and brine (100 ml). The organic extract was dried (Na$_2$SO$_4$) and concentrated under reduced pressure to give 450 mg of the product as a white solid: IR (KBr) 2979, 1707, 1500, 1367, 1153 cm$^{-1}$; $^1$H NMR (CDCl$_3$, 300 MHz) δ 1.10–1.17 (m, 1H), 1.42 (s, 9H), 1.45–1.46 (m, 2H), 1.91–1.98 (m, 2H), 2.30–2.38 (m, 2H), 3.16 (d, J=6.6 Hz, 2H), 3.87 (brs, 1H), 4.49 (brs, 1H), 7.54–7.69 (m, 3H), 7.89–7.92 (m, 2H).

Step 2: cis-(±)-3-Phenylsulfonylmethylcyclopentan-1-amine: This compound was prepared from Step 1 intermediate (850 g) as described in Example 1, Step 2 to give 480 mg of the amine as a semisolid which was used as such for the next step.

Step 3: (2S)-1-{2-[(3SR,1RS)-3-Phenylsulfonylmethylcyclopentylamino]acetytl}-pyrro-lidine-2-carbonitrile: This compound was prepared from Step 2 intermediate (300 mg, 2.25 mmol) and Intermediate 18 (107 mg, 1.62 mmol) using K$_2$CO$_3$ (345 mg, 2.50 mmol) and NaI (187 mg, 1.246 mmol) in dry THF (30 ml) as described in Example 1, Step 3 to give 50 mg of the product as a semisolid: IR (neat) 3400, 2953, 2239, 1658, 1446, 1303, 1148 cm$^{-1}$; $^1$H NMR (CDCl$_3$, 300 MHz) δ 1.15–1.33 (m, 2H), 1.45–1.50 (m, 1H), 1.74–1.91 (m, 2H), 2.11–2.40 (m, 7H), 3.09–3.69 (m, 5H), 3.35 (s, 2H), 4.70–4.77 (m, 1H), 7.54–7.68 (m, 3H), 7.80 (d, J=8.4 Hz, 2H).

Example 30

(2S)-1-{2-[(3S,1R)-3-Phenylsulfanylmethylcycopentylamino]acetytl}-pyrrolidine-2-carbonitrile

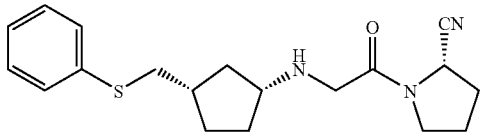

Step 1: N1-BOC-(3S,1R)-3-phenylsulfanylmethylcyclopentan-1-amine: This compound was prepared from Intermediate 8 (3.0 g, 10.23 mmol) and thiophenol (1.13 g, 10.23 mmol) using K$_2$CO$_3$ (2.0 g, 14.49 mmol) in DMF (30 ml) as described in Example 28, Step 1 to give 3.0 g of the product as a white solid: IR (KBr) 3406, 2968, 1687, 1513, 1364, 1297, 1172 cm$^{-1}$; $^1$H NMR (CDCl$_3$, 300 MHz) δ 1.05–1.16 (m, 1H), 1.34–1.49 (m, 2H), 1.43 (s, 9H), 1.81–2.02 (m, 2H), 2.11–2.22 (m, 1H), 2.26–2.35 (m, 1H), 2.95 (d, J=6.9 Hz, 2H), 3.90 (brs, 1H), 4.50 (brs, 1H), 7.14–7.35 (m, 5H).

Step 2: (3S,1R)-3-phenylsulfanylmethylcyclopentan-1-amine: This compound was prepared from Step 1 intermediate (1.0 g) as described in Example 1, Step 2 to give 675 mg of the amine as a semisolid, which was used as such for the next step.

Step 3: (2S)-1-{2-(3S,1R)-3-Phenylsulfanylmethylcyclopentylamino]acetyl}-pyrrolidine-2-carbonitrile: This compound was prepared from Step 2 intermediate (600 mg, 2.88 mmol) and Intermediate 18 (250 mg, 1.44 mmol) using K$_2$CO$_3$ (400 mg, 2.88 mmol) and NaI (217 mg, 1.44 mmol) in dry THF (30 ml) as described in Example 1, Step 3 to give 180 mg of the product as a semisolid: IR (neat) 3316, 2947, 2239, 1661, 1413, 1313, 1144 cm$^{-1}$; $^1$H NMR (CDCl$_3$, 300 MHz) δ 1.13–1.17 (m, 1H), 1.47–1.55 (m, 2H), 1.85 (brs, 2H), 2.10–2.31 (m, 7H), 2.98 (dd, J=5.1, 2.1 Hz, 2H), 3.08–3.13 (m, 1H), 3.36 (s, 2H), 3.39–3.60 (m, 2H), 4.76 (d, J=7.2 Hz, 1H), 7.13–7.18 (m, 1H), 7.24–7.33 (m, 4H), Example 31

(2S)-1-{2-[(3S,1R)-3-Phenylsulfonylmethylcyclopentylamino]acetytl}-pyrrolidine-2-carbonitrile

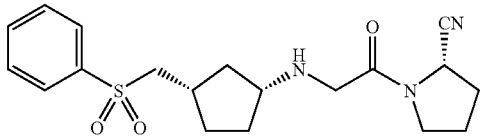

Step 1: N1-BOC-(3S,1R)-3-phenylsulfonylmethylcyclopentan-1-amine: This compound was prepared by the oxidation of N1-BOC-(3S,1R)-3-Phenylsulfanylmethylcyclopentan-1-amine (1.4 g, 4.56 mmol), obtained from Example 30 using 50% m-chloroperbenzoic acid (3.93 g, 11.3 mmol) as described in Example 29, Step 1 to give 1.4 g of the product as a white solid: IR (KBr) 3381, 2975, 1715, 1522, 1448, 1365, 1298, 1251, 1168, 1085 cm$^{-1}$; $^1$H NMR (CDCl$_3$, 300 MHz) δ 1.10–1.14 (m, 1H), 1.40–1.50 (m, 2H), 1.42 (s, 9H), 1.91–1.98 (m, 2H), 2.32–2.36 (m, 2H), 3.16 (d, J=6.6 Hz, 2H), 3.90 (brs, 1H), 4.50 (brs, 1H), 7.54–7.60 (m, 2H), 7.64–7.69 (m, 1H), 7.89–7.93 (m, 2H).

Step 2: (3S,1R)-3-phenylsulfonylmethylcyclopentan-1-amine. This compound was prepared from Step 1 intermediate (1.1 g) as described in Example 1, Step 2 to give 745 mg of the amine as a semisolid which was used as such for the next step.

Step 3: (2S)-1-{2-[(3S,1R)-3-phenylsulfonylmethylcycopentylamino]acetyl}-pyrrolidine-2-carbonitrile: This compound was prepared from Step 2 intermediate (700 mg, 2.92 mmol) and Intermediate 18 (253 mg, 1.46 mmol) using K$_2$CO$_3$ (404 mg, 2.92 mmol) and NaI (220 mg, 1.46 mmol) in THF (30 ml) as described in Example 1, Step 3 to give 217 mg of the product as a semisolid: IR (neat) 3318, 2955, 2240, 1659, 1412, 1303, 1148, 1085 cm$^{-1}$; $^1$H NMR (CDCl$_3$, 300 MHz) δ 1.17–1.27 (m, 1H), 1.44–1.54 (m, 2H), 1.73–1.91 (m, 4H), 2.09–2.40 (m, 5H), 3.07–3.22 (m, 3H), 3.34–3.60 (m, 4H), 4.73–4.77 (m, rotomer, 1H), 7.53–7.65 (m, 3H), 7.88–7.92 (m, 2H).

Example 32

(2S)-1-{2-[(1S,3R)-3-Phenylsulfanylmethylcycopentylamino]acetyl}-pyrrolidine-2-carbonitrile

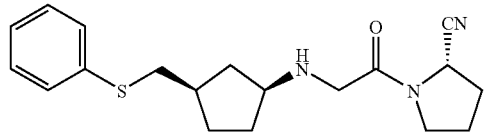

Step 1: N1-BOC-(1S,3R)-3-phenylsulfanylmethylcyclopentan-1-amine: This compound was prepared from Intermediate 12 (3.0 g, 10.23 mmol) and thiophenol (1.35 g, 12.27 mmol) using K$_2$CO$_3$ (2.21 g, 16.00 mmol) in dry DMF (25 ml) as described in Example 28, Step 1 to give 2.9 g of the product as a white solid: IR (neat) 3406, 2968, 1688, 1581, 1513, 1172 cm$^{-1}$; $^1$H NMR (CDCl$_3$, 300 MHz) δ 1.05–1.16 (m, 1H), 1.36–1.51 (m, 2H), 1.43 (s, 9H), 1.81–1.96 (m, 2H), 2.11–2.21 (m, 1H), 2.26–2.35 (m, 1H), 2.95 (d, J=6.9 Hz, 2H), 3.91 (brs, 1H), 4.51 (brs, 1H), 7.14–7.34 (m, 5H).

Step 2: (1S,3R)-3-phenylsulfanylmethylcyclopentan-1-amine: This compound was prepared from Step 1 intermediate (1.0 g) as described in Example 1, Step 2 to give 675 mg of the compound as a semisolid, which was used as such for the next step.

Step 3: (2S)-1-{2-(1S,3R)-3-phenylsulfanylmethylcyclopentylamino]acetyl}-pyrrolidine-2-carbonitrile: This compound was prepared form Step 2 intermediate (600 mg, 2.88 mmol) and Intermediate 18 (250 mg, 1.44 mmol) using K$_2$CO$_3$ (400 mg, 2.88 mmol) and NaI (217 mg, 1.44 mmol) in dry THF (30 ml) as described in Example 1, Step 3 to give 200 mg of the product as a semisolid: IR (neat) 3314, 2947, 2240, 1660, 1414, 1313 cm$^{-1}$; $^1$H NMR (CDCl$_3$, 300 MHz) δ 1.13–1.17 (m, 1H), 1.46–1.55 (m, 2H), 1.72 (brs, 1H, D$_2$O exchangeable), 1.78–1.90 (m, 2H), 2.07–2.31 (m, 6H), 2.98 (d, J=6.9 Hz, 2H), 3.08–3.13 (m, 1H), 3.36 (s, 2H), 3.39–3.61 (m, 2H), 4.75 (m, 1H), 7.13–7.34 (m, 5H).

Example 33

(2S)-1-{2-[(1S,3R)-3-Phenylsulfonylmethylcyclopentylamino]acetyl}-pyrrolidine-2-carbonitrile

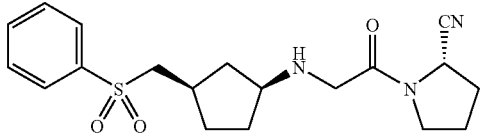

Step 1: N1-BOC-(1S,3R)-3-phenylsulfonylmethylcyclopentan-1-amine: This compound was prepared from N1-BOC-(1S,3R)-3-phenylsulfanylmethylcyclopentan-1-amine (1.4 g, 4.56 mmol) from Example 32 and 50% m-chloroperbenzoic acid (3.93 g of 50%, 11.3 mmol) in chloroform (30 ml) as described in Example 29, Step 1 to give 1.55 g of the product as a white solid: IR (KBr) 3381, 2975, 1715, 1522, 1448, 1365, 1299, 1251, 1147, 1085 cm$^{-1}$; $^1$H NMR (CDCl$_3$, 300 MHz) δ 1.10–1.17 (m, 1H), 1.35–1.50 (m, 2H), 1.42 (s, 9H), 1.91–1.99 (m, 2H), 2.32–2.38 (m, 2H), 3.16 (d, J=6.6 Hz, 2H), 3.88 (brs, 1H), 4.45 (brs, 1H), 7.26–7.59 (m, 2H), 7.64–7.69 (m, 1H), 7.89–7.93 (m, 2H).

Step 2: (1S,3R)-3-phenylsulfonylmethylcyclopentan-1-amine: This compound was prepared from Step 1 intermediate (1.0 g) as described in Example 1, Step 2 to give 702 mg of the amine as a semisolid which was used as such for the next step.

Step 3: (2S)-1-{2-[(1S,3R)-3-phenylsulfonylmethylcyclopentylamino]acetyl}-pyrrolidine-2-carbonitrile: This compound was prepared from Step 2 intermediate (600 mg, 2.88 mmol) and Intermediate 18 (250 mg, 1.44 mmol) using K$_2$CO$_3$ (400 mg, 2.88 mmol) and NaI (217 mg, 1.44 mmol) in dry THF (30 ml) as described in Example 1, Step 3 to give 90 mg of the product as a semisolid: IR (neat) 3317, 2955, 2244, 1659, 1446, 1304, 1148 cm$^{-1}$; $^1$H NMR (CDCl$_3$, 300 MHz) δ 1.17–1.28 (m, 1H), 1.46–1.53 (m, 2H), 1.74–1.93 (m, 2H), 2.10–2.43 (m, 7H), 3.11–3.23 (m, 3H), 3.35 (d, J=1.5 Hz, 2H), 3.39–3.62 (m, 2H), 4.73–4.77 (m, rotomer, 1H), 7.54–7.68 (m, 3H), 7.89–7.92 (m, 2H).

Example 34

(2S)-1-{2-[(1S,3R)-3-(4-Fluorophenylsulfanylmethyl)cyclopentylamino]acetyl}-pyrro-lidine-2-carbonitrile

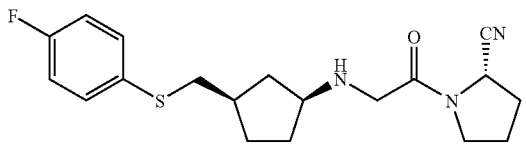

Step 1: N1-BOC-(1S,3R)-3-(4-fluorophenylsulfanylmethyl)cyclopentan-1-amine: This compound was prepared from Intermediate 12 (1.6 g, 5.46 mmol) and 4-fluorothiophenol (0.83 g, 6.54 mmol) using K$_2$CO$_3$ (1.13 g, 8.19 mmol) in dry DMF (30 ml) as described in Example 28, Step 1 to give 1.29 g of the compound as a white solid: IR (KBr ) 3372, 2969, 1678, 1588, 1519, 1152 cm$^{-1}$; $^1$H NMR (CDCl$_3$, 300 MHz) δ 1.03–1.14 (m, 1H), 1.36–1.50 (m, 2H), 1.43 (s, 9H), 1.78–1.87 (m, 1H), 1.93–2.01 (m, 1H), 2.08–2.16 (m, 1H), 2.25–2.34 (m, 1H), 2.89 (d, J=4.2 Hz, 2H), 3.90 (brs, 1H), 4.49 (brs, 1H), 6.94–7.02 (m, 2H), 7.26–7.36 (m, 2H).

Step 2: (1S,3R)-3-(4-fluorophenylsulfanylmethyl)cyclopentan-1-amine: This compound was prepared from Step 1 intermediate (640 g) as described in Example 1, Step 2 to give 470 mg of the compound as a semisolid, which was used as such for the next step.

Step 3: (2S)-1-{2-(1S,3R)-3-(4-fluorophenylsulfanylmethyl)cyclopentylamino]acetyl}-pyrrolidine-2-carbonitrile: This compound was prepared form Step 2 intermediate (400 mg, 2.07 mmol) and Intermediate 18 (178 mg, 1.03 mmol) using K$_2$CO$_3$ (286 mg, 2.07 mmol) and NaI (310 mg, 2.07 mmol) in THF (30 ml) as described in Example 1, Step 3 to give 140 mg of the product as a semisolid: IR (neat) 3316, 2949, 2240, 1661, 1490, 1416, 1222 cm$^{-1}$; $^1$H NMR (CDCl$_3$, 300 MHz) δ 1.10–1.25 (m, 1H), 1.47–1.55 (m, 2H), 1.81–1.84 (m, 4H), 2.05–2.33 (m, 5H), 2.92 (d, J=6.9 Hz, 2H), 3.90–3.13 (m, 1H), 3.37 (s, 2H), 3.39–3.62 (m, 2H), 4.73–4.77 (m, 1H), 6.95–7.01 (m, 2H), 7.29–7.35 (m, 2H).

Example 35

(2S)-1-{2-[(4S,1R)-4-(2-Pyridylsulfanylmethyl)cyclopent-2-enealino]acetyl}-pyrrolidine-2-carbonitrile

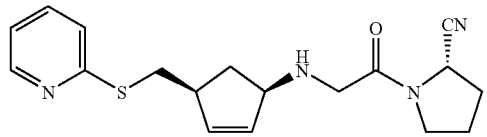

Step 1: N1-BOC-(4S,1R)-4-(2-pyridysulfanylmethyl)cyclopent-2-ene-1-amine: This compound was prepared from (4R,1S)-4-N—BOC-aminocyclopent-2-enylmethyl methane sulfonate (1.0 g, 3.43 mmol) from Intermediate 14, Step 2, Method B and 2-mercaptopyridine (496 mg, 4.46 mmol) using K$_2$CO$_3$ (711 g, 5.15 mmol) in dry DMF (20 ml) as described in Example 28, step 1 to give 1.01 g of the compound as a white solid: IR (neat) 3337, 2974, 1707, 1579, 1454, 1168 cm$^{-1}$; $^1$H NMR (CDCl$_3$, 300 MHz) δ 1.34–1.45 (m, 1H), 1.45 (s, 9H), 2.54–2.58 (m, 1H), 2.98–3.02 (m, 1H), 3.21–3.35 (m, 2H), 4.66 (brs, 1H), 5.02 (brs, 1H), 5.74–5.77 (m, 1H), 5.84–5.87 (m, 1H), 6.96–7.00 (m, 1H), 7.19 (d, J=Hz, 1H), 7.44–7.49 (m, 1H), 8.42 (d, J=4.2 Hz, 1H).

Step 2: (4S,1R)-4-(2-pyridysulfanylmethyl)cyclopent-2-ene-1-amine: This compound was prepared from Step 1 intermediate (600 mg, 1.96 mmol) as described in Example 1, Step 2 to give 344 mg of the compound as a semisolid, which was used as such for the next step.

Step 3: (2S)-1-{2-[(4S,1 R)-4-(2-Pyridylsulfanylmethyl)cyclopent-2-ene-1-amino]acetyl}-pyrrolidine-2-carbonitrile: This compound was prepared form Step 2 amine (340 mg, 1.60 mmol) and Intermediate 18 (142 mg, 0.82 mmol) using K$_2$CO$_3$ (454 mg, 3.29 mmol) and NaI (247 mg, 1.64 mmol) in dry THF (30 ml) as described in Example 1, Step 3 to give 140 mg of the product as a semisolid: IR (neat) 3046, 2943, 1658, 1578, 1414, 1124 cm$^{-1}$; $^1$H NMR (CDCl$_3$, 300 MHz) δ 1.32–1.40 (m, 1H), 2.07–2.33 (m, 4H), 2.42–2.51 (m, 1H), 3.00–3.05 (m, 1H), 3.27–3.29 (m, 2H), 3.42 (s, 2H), 3.35–3.63 (m, 3H), 3.85–3.90 (m, 1H), 4.77 (d, J=6.3 Hz, rotomer, 0.8H), 4.89–4.91 (m, rotomer, 0.2H), 5.78–5.82 (m, 1H), 5.86–5.89 (m, 1H), 6.95–6.98 (m, 1H), 7.18 (dd, J=6.9.0.9 Hz, 1H), 7.44–7.49 (m, 1H), 8.40–8.42 (m, 1H).

Example 36

(2S)-1-{2-[(1S,3R)-3-(2-Pyridylsulfanylmethyl)cyclopentylamino]acetyl}-pyrrolidine-2-carbonitrile

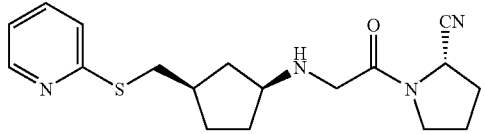

Step 1: N1-BOC-(1S,3R)-3-(2-pyridylsulfanylmethyl)cyclopentyl-1-amine: This compound was prepared from Intermediate 12 (1 g, 3.41 mmol) and 2-mercaptopyridine (455 mg, 4.09 mmol) using $K_2CO_3$ (706 mg, 5.11 mmol) in dry DMF (20 ml) as described in Example 28, Step 1 to give 720 mg of the compound as a white solid: IR (neat) 3335, 2972, 1694, 1505, 1454, 1365, 1247, 1124 $cm^{-1}$; $^1H$ NMR ($CDCl_3$, 300 MHz) δ 1.17–1.26 (m, 1H), 1.44 (s, 9H), 1.47–1.59 (m, 2H), 1.86–1.99 (m, 2H), (m, 2H), 3.19 (dd, J=6.8, 6.6 Hz, 1H), 3.31 (dd, J=6.8, 6.6 Hz, 1H), 3.94 (brs, 1H), 4.93 (brs, 1H), 6.94–6.99 (m, 1H), 7.17 (d, J=9.9 Hz, 1H), 7.43–7.49 (m, 1H), 8.43 (d, J=5.5 Hz, 1H).

Step 2: (1S,3R)-3-(2-pyridysulfanylmethyl)cyclopentyl-1-amine: This compound was prepared from Step 1 intermediate (700 mg) as described in Example 1, Step 2 to give 310 mg of the compound as a semisolid, which was used as such for the next step.

Step 3: (2S)-1-{2-[(1S,3R)-3-(2-pyridylsulfanylmethyl)cyclopentylamino]acetyl}-pyrro-lidine-2-carbonitrile: This compound was prepared from Step 2 intermediate (300 mg, 1.44 mmol) and Intermediate 18 (124 mg, 0.72 mmol) using $K_2CO_3$ (198 mg, 1.42 mmol) and NaI (107 mg, 0.72 mmol) in dry THF (30 ml) as described in Example 1, Step 3 to give 110 mg of the product as a semisolid: IR (neat) 3318, 2948, 2240, 1640, 1414, 1124 $cm^{-1}$; $^1H$ NMR ($CDCl_3$, 300 MHz) δ 1.31–1.22 (m, 1H), 1.48–1.57 (m, 2H), 1.80–1.90 (m, 2H), 2.07–2.32 (m, 7H), 3.09–3.15 (m, 1H), 3.26 (d, J=6.9 Hz, 2H), 3.78 (s, 2H), 3.40–3.62 (m, 2H), 4.75–4.80 (m, 1H), 6.95 (dd, J=4.5, 2.7 Hz, 1H), 7.16 (d, J=8.1 Hz, 1H), 7.46 (dt, J=5.4, 2.1 Hz, 1H), 8.40 (d, J=6.0 Hz, 1H).

Example 37

(2S)-1-{2-[(1S,3R)-3-(2-Pyridylsulfonylmethyl)cyclopentylamino]acetyl}-pyrrolidine-2-carbonitrile

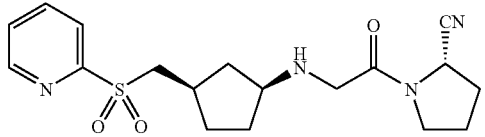

Step 1: N1-BOC-(1S,3R)-2-pyridylsulfonylmethylcyclopentan-1-amine. This compound was prepared by the oxidation of N1-BOC-(1S,3R)-3-(2-pyridylsulfanylmethyl)-cyclopentyl-1-amine (1.4 g, 4.536 mmol) from Example 36, Step 1 using 50% m-chloroperbenzoic acid (3.93 g , 11.3 mmol) as described in Example 29, Step 1 to give 1.3 g of the product as a white solid: IR (KBr) 3372, 2975, 1702, 1524, 1304, 1162 $cm^{-1}$; $^1H$ NMR ($CDCl_3$, 300 MHz) δ 1.14–1.18 (m, 1H), 1.42 (s, 9H), 1.38–1.51 (m, 2H), 1.88–2.01 (m, 2H), 2.27–2.35 (m, 2H), 3.48 (d, J=6.9 Hz, 2H), 3.89 (brs, 1H), 4.48 (brs, 1H), 7.54–7.59 (m, 1H), 7.17 (dt, J=5.7, 1.8 Hz, 1H), 8.13 (d, J=9.9 Hz, 1H), 8.74–8.76 (m, 1H).

Step 2: (1S,3R)-2-pyridylsulfonylmethylcyclopentan-1-amine: This compound was prepared from Step 1 intermediate (1.0 g) as described in Example 1, Step 2 to give 603 mg of the compound as a semisolid, which was used as such for the next step.

Step 3: (2S)-1-{2-[(1S,3R)-3-(2-pyridylsulfonylmethyl)cyclopentylamino]acetyl}-pyrrolidine-2-carbonitrile: This compound was prepared from Step 2 intermediate (500 mg, 2.403 mmol) and Intermediate 18 (207 mg, 1.201 mmol) using $K_2CO_3$ (332 mg, 2.403 mmol) and NaI (180 mg, 1.201 mmol) in dry THF (25 ml) as described in Example 1, Step 3 to give 210 mg of the product as semisolid: IR (neat) 3306, 2946, 2241, 1656, 1427, 1305, 1163 $cm^{-1}$; $^1H$ NMR ($CDCl_3$, 300 MHz) δ 1.18–1.35 (m, 2H), 1.49–1.58 (m, 2H), 1.87–2.00 (m, 2H), 2.07–2.46 (m, 6H), 3.12–3.19 (m, 1H), 3.34–3.58 (m, 6H), 4.76 (d, J=6.9 Hz, 1H), 7.56 (dd, J=6.0, 1.8 Hz, 1H), 7.94–8.00 (m, 1H), 8.10 (d, J=7.8 Hz, 1H), 8.75 (d, J=4.5 Hz, 1H).

Example 38

6-((1SR,3RS)-3-{2-[(2S)-2-Cyanopyrrolidin-1-yl]-2-oxoethylamino}cyclopentyl-methylsulfanyl)nicotinonitrile

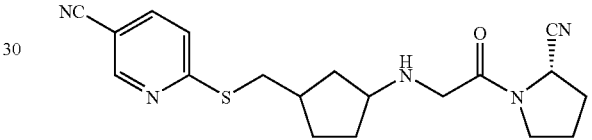

Step 1: cis-(±)-6-(3-N—BOC-aminocyclopentylmethylsulfanyl)nicotinonitrile: This compound was prepared from the Intermediate 4 (2.0 g, 6.825 mmol) and 5-cyano-2-mercaptopyridine (930 mg, 6.838 mmol) using $K_2CO_3$ (1.04 g, 10.15 mmol) in dry DMF (25 ml) as described in Example 28 to give 2.1 g of the product as a white solid: IR (KBr) 3345, 2960, 2235, 1684, 1531, 1464, 1365, 1112 $cm^{-1}$; $^1H$ NMR ($CDCl_3$, 300 MHz) δ 1.14–1.21 (m, 1H), 1.43 (s, 9H), 1.45–1.52 (m, 2H), 1.93–3.00 (m, 2H), 2.30–2.71 (m, 2H), 3.52 (d, J=6.6 Hz, 2H), 3.89 (brs, 1H), 4.51 (brs, 1H), 8.22–8.30 (m, 2H), 8.99 (s, 1H).

Step 2: cis-(±)-6-(3-aminocyclopentylmethylsulfanyl)nicotinonitrile: This compound was prepared from Step 1 intermediate (600 mg) as described in Example 1, Step 2 to give 330 mg of the product as a semisolid, which was used as such for the next step. Step 3: 6-((1SR,3RS)-3-{2-[(2S)-2-cyanopyrrolidin-1-yl]-2-oxoethylamino}cyclopentyl-methylsulfanyl)nicotinonitrile: This compound was prepared form Step 2 intermediate (300 mg, 1.287 mmol) and Intermediate 18 (111 mg, 0.643 mmol) using $K_2CO_3$ (178 mg, 1.287 mmol) and NaI (97 mg, 0.643 mmol) in THF (30 ml) as described in Example 1, Step 3 to give 180 mg of the product as a semisolid: IR (neat) 3317, 2947, 2470, 2229, 1659, 1583, 1460, 1414, 1112 $cm^{-1}$; $^1H$ NMR ($CDCl_3$, 300 MHz) δ 1.12–1.27 (m, 1H), 1.47–1.56 (m, 2H), 1.80–1.87 (m, 3H), 2.08–2.33 (m, 6H), 3.11–3.15 (m, 1H), 3.28 (d, J=6.9 Hz, 2H), 3.37 (s, 2H), 3.40–3.63 (m, 2H), 4.75–4.78 (m, 1H), 7.23 (dd, J=7.5, 0.9 Hz, 1H), 7.63 (dd, J=6.3, 2.1 Hz, 1H), 8.63 (dd, J=1.5, 0.6 Hz, 1H).

Example 39

6-((1SR,3RS)-3-{2-[(2S)-2-Cyanopyrrolidin-1-yl]-2-oxoethylamino}cyclopentyl-methylsulfanyl)nictinonitrile maleate

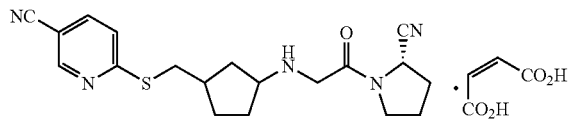

A solution of maleic acid (32 mg, 0.275 mmol) in EtOAc (4 ml) was added to a stirred solution of free base (100 mg, 0.271 mmol) from Example 38 in EtOAc (4 ml) at room temperature. The mixture was stirred for 20 min. and the solid separated out was collected by filtration. The product was dried under vacuum to give 120 mg of the product as a white solid: IR (KBr) 3437, 2981, 2228, 1667, 1584, 1460, 1350, 1110 cm$^{-1}$; $^1$H NMR (D$_2$O, 300 MHz) δ 1.43–1.46 (m, 1H), 1.85–1.64 (m, 1H), 1.78–1.85 (m, 1H), 1.94–2.01 (m, 1H), 2.09–2.47 (m, 7H), 3.34–3.70 (m, 5H), 3.97–4.11 (m, rotomer, 2H), 4.78–4.90 (m, rotomer, 1H), 6.27 (s, 2H), 7.40 (dd, J=7.8, 0.6 Hz, 1H), 7.85 (dd, J=6.3, 2.4 Hz, 1H), 8.70 (d, J=2.4 Hz, 1H).

Example 40

6-((1SR,3RS)-3-{2-[(2S)-2-Cyanopyrrolidin-1-yl]-2-oxoethylamino}cyclopentyl-methylsulfonyl)nicotinonitrile

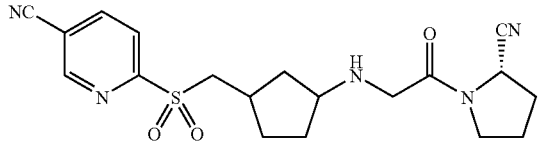

Step 1: cis-(±)-6-(3-N—BOC-aminocyclopentylmethylsulfonyl)nicotinonitrile: This compound was prepared by the oxidation of cis-(±)-6-(3-N—BOC-aminocyclopentylmethylsulfanyl)nicotinonitrile (1.1 g, 3.303 mmol) from Example 38 with 50% m-chloroperbenzoic acid (2.86 g, 8.289 mmol) in chloroform (25 ml) as described in Example 29, Step 1 to give 1.2 g of the product as a white solid: IR (KBr) 3360, 2977, 2239, 1685, 1530, 1317, 1158 cm$^{-1}$; $^1$H NMR (CDCl$_3$, 300 MHz) δ 1.14–1.21 (m, 1H), 1.43 (s, 9H), 1.48–1.52 (m, 2H), 1.93–2.00 (m, 2H), 2.30–2.37 (m, 2H), 3.52 (d, J=6.6 Hz, 2H), 3.89 (brs, 1H), 4.51 (brs, 1H), 8.22–8.30 (m, 2H), 8.99 (s, 1H).

Step 2 cis-(±)-6-(3-aminocyclopentylmethylsulfonyl)nicotinonitrile: This compound was prepared from Step 1 intermediate (600 mg) as described in Example 1, Step 2 to give 328 mg of the amine as a semisolid, which was used as such for the next step.

Step 3: 6-((1SR,3RS)-3-{2-[(2S)-2-Cyanopyrrolidin-1-yl)-2-oxoethylamino}cyclopentyl-methylsulfonyl)nicotinonitrile: This compound was prepared from Step 2 intermediate (300 mg, 1.132 mmol) and Intermediate 18 (98 mg, 0.568 mmol) using K$_2$CO$_3$ (157 mg, 1.137 mmol) and NaI (85 mg, 0.568 mmol) in THF (20 ml) as described in Example 1, Step 3 to give 157 mg of the product as semisolid: IR (neat) 3400, 2955, 2238, 1662, 1456, 1313, 1156 cm$^{-1}$; $^1$H NMR (CDCl$_3$, 300 MHz) δ 0.85–0.089 (m, 1H), 1.25–1.39 (m, 3H), 1.49–1.67 (m, 3H), 1.83–2.47 (m, 6H), 3.20 (brs, 1H), 3.41 (s, 2H), 3.57 (d, J=7.2 Hz, 1H), 3.50–3.69 (m, 2H), 4.68–2.77 (m, 1H), 8.22–8.29 (m, 2H), 8.99 (s, 1H).

Example 41

(2S)-1-{2-[(3S,1R)-3-(2-Pyrimidinylsulfanylmethyl)cyclopentylamino]acetyl}-pyrrol-idine-2-carbonitrile

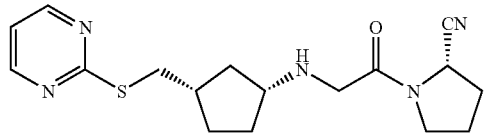

Step 1: N1-BOC-(3S,1R)-3-(2-pyrimidinyllsulfanylmethyl)cyclopentan-1-amine: This compound was prepared from Intermediate 8 (2.0 g, 6.826 mmol) and 2-mercaptopyrimidine (765 mg, 6.83 mmol) using K$_2$CO$_3$ (1.04 g, 7.536 mmol) in dry DMF (25 ml) as described in Example 28, Step 1 to give 1.7 g of the compound as a white solid: IR (KBr) 3330, 2968, 1699, 1566, 1382, 1171 cm$^{-1}$; $^1$H NMR (CDCl$_3$, 300 MHz) δ 1.15–1.25 (m, 1H), 1.44 (s, 9H), 1.41–1.58 (m, 2H), 1.85–2.07 (m, 2H), 2.27–2.34 (m, 2H), 3.15–3.31 (m, 2H), 3.95 (brs, 1H), 4.83 (brs, 1H), 6.96 (t, J=4.8 Hz, 1H), 8.51 (d, J=5.1 Hz, 2H).

Step 2: (3S,1R)-3-(2-pyrimidinyllsulfanylmethyl)cyclopentan-1-amine: This compound was prepared from Step 1 intermediate (700 mg) as described in Example 1, Step 2 to give 351 mg of the compound as a semisolid, which was used as such for the next step.

Step 3: (2S)-1-{2-[(3S,1R)-3-(2-Pyrimidinylsulfanylmethyl)cyclopentylamino]acetyl}-pyrrolidine-2-carbonitrile: This compound was prepared from Step 2 intermediate (300 mg, 1.435 mmol) and Intermediate 18 (124 mg, 0.718 mmol) using K$_2$CO$_3$ (199 mg, 1.443 mmol) and NaI (108 mg, 0.718 mmol) in dry THF (30 ml) as described in Example 1, Step 3 to give 175 mg of the product as a semisolid: IR (neat) 3316, 2949, 2241, 1659, 1565, 1548, 1382, 1189 cm$^{-1}$; $^1$H NMR (CDCl$_3$, 300 MHz) δ 1.13–1.23 (m, 1H), 1.48–1.58 (m, 2H), 1.84–1.90 (m, 2H), 2.09–2.33 (m, 7H), 3.10–3.17 (m, 1H), 3.23 (d, J=6.9 Hz, 2H), 3.37 (s, 2H), 3.37–3.62 (m, 2H), 4.75–2.77 (m, 1H), 6.94 (t, J=4.8 Hz, 1H), 8.50 (d, J=5.1 Hz, 2H).

Example 42

(2S)-1-{2-[(3S,1R)-3-(1H-Benzo[d]imidazol-2-ylsulfanylmethyl)cyclopentylamino]-acetyl}-pyrrolidine-2-carbonitrile

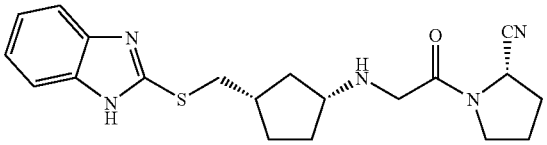

Step 1: N1-BOC-(3S,1R)-3-(1H-benzo[d]imidazol-2-ylsulfanylmethyl)cyclopentyl-1-amine: This compound was prepared from Intermediate 8 (2 g, 6.825 mmol) and 2-mercaptobenzo[d]imidazole (1.03 g, 6.866 mmol) using K$_2$CO$_3$ (1.04 g, 7.536 mmol) in dry DMF (20 ml) as described in Example 28, Step 1 to give 1.5 g of the compound as a white solid: IR (KBr) 3384, 3074, 2972, 1684, 1529, 1404, 1272, 1182 cm$^{-1}$; $^1$H NMR (CD$_3$OD, 300 MHz) δ 1.19–1.25 (m, 1H), 1.42 (s, 9H), 1.39–1.55 (m, 2H), 1.86–200 (m, 2H), 2.20–2.26 (m, 2H), 3.28–3.31 (m, 2H), 3.83 (brs, 1H), 7.16–7.19 (m, 2H), 7.43–7.46 (m, 2H).

Step 2: (3S,1R)-3-(1H-benzo[d]imidazol-2-ylsulfanylmethyl)cyclopentyl-1-amine: This compound was prepared from Step 1 intermediate (800 mg) as described in Example 1, Step 2 to give 450 mg of the compound as a semisolid, which was used as such for the next step.

Step 3: (2S)-1-{2-[(3S,1R)-3-(1H-benzo[d]imidazol-2-ylsulfanylmethyl)cyclopentyl-amino]acetyl}-pyrrolidine-2-carbonitrile: This compound was prepared from Step 2 intermediate (400 mg, 1.619 mmol) and Intermediate 18 (140 mg, 0.812 mmol) using K$_2$CO$_3$ (224 mg, 1.62 mmol) and NaI (123 mg, 0.810 mmol) in dry THF (30 ml) as described in Example 1, Step 3 to give 65 mg of the product as a white solid: IR (KBr) 3304, 2953, 2240, 1659, 1406, 1267 cm$^{-1}$; $^1$H NMR (CDCl$_3$, 300 MHz) δ 1.25–1.41 (m, 2H), 1.53–1.57 (m, 2H), 1.81–1.90 (m, 2H), 2.04–2.36 (m, 7H), 3.14–3.19 (m, 1H), 3.36 (s, 2H), 3.29–3.55 (m, 4H), 4.71–4.75 (m, 1H), 7.15–7.20 (m, 2H), 7.49 (brs, 2

Example 43

(2S)-1-{2-[(3SR,1RS)-3-(4-Nitrophenoxymethyl)cyclopentylamino]acetyl}-pyrro-lidine-2-carbonitrile

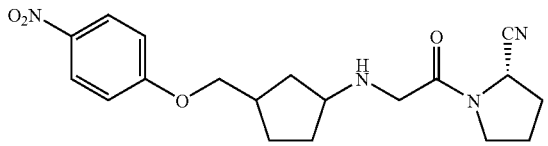

Step 1: cis-(±)-N1-BOC-3-(4-nitrophenoxymethyl)cyclopentan-1-amine: Diethyl azodicarboxylate (2.0 g, 11.47 mmol) was added (5 min) to a well-stirred solution of Intermediate 3 (1.9 g, 8.83 mmol), 4-nitrophenol (1.23 g, 8.83 mmol) and triphenylphosphine (3.47 g, 13.22 mmol) in dry THF (30 ml) at room temperature. The temperature of the mixture was slowly raised to 60–70° C. and further maintained at the same temperature for 3 h under nitrogen atmosphere. The solvent was then evaporated under reduced pressure and the residue obtained was purified by silica gel column chromatography using 10% EtOAc in petroleum ether to give 2.5 g of the product as a white solid: IR (KBr) 3371, 1688, 1530, 1520, 1332, 1258, 1168 cm$^{-1}$; $^1$H NMR (CDCl$_3$, 300 MHz) δ 1.22–1.31 (m, 1H), 1.45 (s, 9H), 1.51–1.62 (m, 2H), 1.85–2.01 (m, 2H), 2.26–2.51 (m, 2H), 3.98 (d, J=5.4 Hz, 2H), 4.02 (brs, 1H), 4.79 (brs, 1H), 6.96 (dd, J=5.1, 2.4 Hz, 2H), 8.20 (dd, J=4.8, 2.1 Hz, 2H).

Step 2: cis-(±)-3-(4-nitrophenoxymethyl)cyclopentan-1-amine: This compound was prepared from Step 1 intermediate (1.0 g) as described in Example 1, Step 2 to give 700 mg of the amine as a semisolid, which was used as such for the next step. Step 3: (2S)-1-{2-[(3SR,1RS)-3-(4-Nitrophenoxymethyl)cyclopentylamino]acetyl}-pyrrolidine-2-carbonitrile: This compound was prepared from Step 2 intermediate (600 mg, 2.56 mmol) and Intermediate 18 (222 mg, 1.29 mmol) using K$_2$CO$_3$ (355 mg, 2.56 mmol) and NaI (194 mg, 1.1.29 mmol) in dry THF (30 ml) as described in Example 1, Step 3 to give 180 mg of the product as a semisolid: IR (neat) 3316, 2951, 2240, 1660, 1592, 1510, 1340, 1262, 1111, 1013 cm$^{-1}$; $^1$H NMR (CDCl$_3$, 300 MHz) δ 1.21–1.65 (m, 3H), 1.54–1.65 (m, 2H), 1.85–1.90 (m, 2H), 2.09–2.47 (m, 5H), 3.17–3.22 (m, 1H), 3.40 (s, 2H), 3.43–3.62 (m, 2H), 3.98 (d, J=6.6 Hz, 2H), 4.75–4.78 (m, rotomer, 1H), 6.94 (dt, J=4.8, 3.3 Hz, 2H), 8.19 (dd, J=4.8, 3.3 Hz, 2H).

Example 44

(2S)-1-{2-[(3S,1R)-3-(4-Nitrophenoxymethyl)cyclopentylamino]acetyl}-pyrrolidine-2-carbonitrile

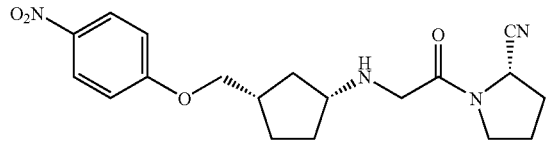

Step 1: N1-BOC-(3S,1R)-3-(4-nitrophenoxymethyl)cyclopentan-1-amine: This compound was prepared from Intermediate 7 (1.9 g, 8.83 mmol) and 4-nitrophenol (1.23 g, 8.83 mmol) using diethyl azodicarboxylate (2.0 g, 11.47 mmol) and triphenylphosphine (3.47 g, 13.22 mmol) in dry THF (30 ml) as described in Example 43, Step 1 to give 2.5 g of the product as a white solid: IR (KBr) 3369, 2921, 1685, 1511, 1334, 1260, 1172, cm$^{-1}$; $^1$H NMR (CDCl$_3$, 300 MHz) δ 1.22–1.31 (m, 1H), 1.45 (s, 9H), 1.51–1.63 (m, 2H), 1.85–2.01 (m, 2H), 2.26–2.52 (m, 2H), 3.98 (d, J=5.4 Hz, 2H), 4.02 (brs, 1H), 4.76 (brs, 1H), 6.96 (dd, J=5.1, 2.4 Hz, 2H), 8.20 (dd, J=4.9, 2.1 Hz, 2H).

Step 2: (3S,1R)-3-(4-nitrophenoxymethyl)cyclopentan-1-amine: This compound was prepared from Step 1 intermediate (900 mg) as described in Example 1, Step 2 to give 625 mg of the amine as a semisolid, which was used as such for the next step.

Step 3: (2S)-1-{2-[(3S,1R)-3-(4-nitrophenoxymethyl)cyclopentylamino]acetyl}-pyrrolidine-2-carbonitrile: This compound was prepared from Step 2 intermediate (600 mg, 2.56 mmol) and Intermediate 18 (222 mg, 1.29 mmol) using K$_2$CO$_3$ (355 mg, 2.56 mmol) and NaI (194 mg, 1.1.29 mmol) in dry THF (30 ml) as described in Example 1, Step 3 to give 180 mg of the product as a semisolid: IR (neat) 3300, 2950, 2225, 1659, 1592, 1509, 1411, 1340, 1262, 1111 cm$^{-1}$; $^1$H NMR (CDCl$_3$, 300 MHz) δ 1.20–1.30 (m, 1H), 1.52–1.63 (m, 2H), 1.87–1.89 (m, 3H), 2.13–2.47 (m, 6H), 3.16–3.20 (m, 1H), 3.39 (s, 2H), 3.40–3.60 (m, 2H), 3.98 (d, J=6.6 Hz, 2H), 4.76–4.79 (m, rotomer, 1H), 6.94 (dd, J=5.1, 2.1 Hz, 2H), 8.19 (dd, J=4.8, 2.1 Hz, 2H).

Example 45

(2S)-1-{2-[(3R,1S)-3-(4-Nitrophenoxymethyl)cyclopentylamino]acetyl}-pyrrolidine-2-carbonitrile

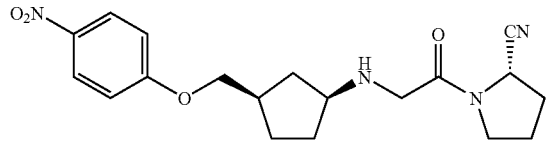

Step 1: N1-BOC-(3R,1S)-3-(4-nitrophenoxymethyl)cyclopentan-1-amine: This compound was prepared form Intermediate 11 (1.9 g, 8.83 mmol) and 4-nitrophenol (1.23 g, 8.83 mmol) using diethyl azodicarboxylate (2.0 g, 11.47 mmol) and triphenylphosphine (3.47 g, 13.22 mmol) in dry THF (30 ml) as described in Example 43, Step 1 to give 2.5 g of the product as a white solid: IR (KBr) 3369, 2966, 1685, 1593, 1511, 1334, 1260, 1172 cm$^{-1}$; $^1$H NMR (CDCl$_3$, 300 MHz) δ 1.22–1.34 (m, 1H), 1.45 (s, 9H), 1.51–1.66 (m, 2H), 1.81–2.04 (m, 2H), 2.26–2.35 (m, 1H), 2.43–2.52 (m, 1H), 3.98 (d, J=6.0 Hz, 2H), 4.02 (brs, 1H), 4.75 (brs, 1H), 9.96 (dd, J=4.8, 2.1 Hz, 2H), 8.20 (dd, J=4.8, 2.1 Hz, 2H).

Step 2: (3R,1S)-3-(4-nitrophenoxymethyl)cyclopentan-1-amine: This compound was prepared from Step 1 intermediate (1.0 g) as described in Example 1, Step 2 to give 670 mg of the amine as a semisolid, which was used as such for the next step.

Step 3: (2S)-1-{2-[(3R,1S)-3-(4-nitrophenoxymethyl)cyclopentylamino]acetyl}-pyrrolidine-2-carbonitrile: This compound was prepared from Step 2 intermediate (600 mg, 2.56 mmol) and Intermediate 18 (222 mg, 1.29 mmol) using $K_2CO_3$ (355 mg, 2.56 mmol) and NaI (194 mg, 1.1.29 mmol) in dry THF (30 ml) as described in Example 1, Step 3 to give 190 mg of the product as a semisolid: IR (neat) 3318, 2953, 2240, 1661, 1592, 1511, 1412, 1340, 1262, 1111 cm$^{-1}$; $^1$H NMR (CDCl$_3$, 300 MHz) δ 1.20–1.30 (m, 2H), 1.54–1.89 (m, 5H), 2.08–2.47 (m, 5H), 3.16–3.21 (m, 1H), 3.39 (s, 2H), 3.37–3.61 (m, 2H), 3.98 (d, J=6.9 Hz, 2H), 4.76–4.78 (m, rotamer, 1H), 6.94 (dd, J=4.8, 2.1 Hz, 2H), 8.18 (dd, J=4.8, 2.1 Hz, 2H).

Example 46

(2S)-1-{2–1(1S,3R)-3-(4-Cyanophenoxymethyl)cyclopentylamino]acetyl}-pyrrolidine-2-carbonitrile

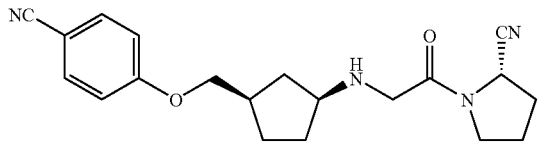

Step 1: N1-BOC-(1S,3R)-3-(4-cyanophenoxymethyl)cyclopentan-1-amine: This compound was prepared from Intermediate 11 (1.5 g, 6.97 mmol) and 4-cyanophenol (830 mg, 6.97 mmol) using diethyl azodicarboxylate (1.58 g, 9.06 mmol) and triphenylphosphine (2.74 g, 10.44 mmol) in dry THF (15 ml) as described in Example 43, Step 1 to give 1.53 g of the product as a white solid: IR (KBr) 3358, 2939, 2224, 1682, 1606, 1521, 1254, 1171 cm$^{-1}$; $^1$H NMR (CDCl$_3$, 300 MHz) δ 1.20–1.31 (m, 1H), 1.45 (s, 9H), 1.38–1.61 (m, 2H), 1.83–1.97 (m, 2H), 2.24–2.33 (m, 1H), 2.40–2.47 (m, 1H), 3.93 (d, J=6 Hz, 2H), 3.98 (brs, 1H), 4.76 (brs, 1H), 6.95 (dd, J=1.8, 5.1 Hz, 2H), 7.58 (dd, J=5.1, 2.4 Hz, 2H).

Step 2: (1S,3R)-3-(4-cyanophenoxymethyl)cyclopentan-1-amine: This compound was prepared from Step 1 intermediate (800 mg) as described in Example 1, Step 2 to give 513 mg of the amine as a semisolid, which was used as such for the next step.

Step 3: (2S)-1-{2-[(1S,3R)-3-(4-cyanophenoxymethyl)cyclopentylamino]acetyl}-pyrrolidine-2-carbonitrile: This compound was prepared from Step 2 intermediate (500 mg, 2.31 mmol) and Intermediate 18 (200 mg, 1.15 mmol) using $K_2CO_3$ (319 mg, 2.31 mmol) and NaI (172 mg, 1.16 mmol) in dry THF (30 ml) as described in Example 1, Step 3 to give 210 mg of the product as a semisolid: IR (neat) 3318, 2951, 2223, 1690, 1605, 1509, 1416, 1303, 1172 cm$^{-1}$; $^1$H NMR (CDCl$_3$, 300 MHz) δ 1.19–1.29 (m, 1H), 1.53–1.65 (m, 2H), 1.80–1.90 (m, 3H), 2.08–2.45 (m, 6H), 3.16–3.21 (m, 1H), 3.39 (s, 2H), 3.37–3.63 (m, 2H), 3.93 (d, J=6.6 Hz, 2H), 4.75–4.78 (m, rotamer, 1H), 6.93 (d, J=9.3 Hz, 2H), 7.57 (d, J=8.7 Hz, 2H).

Example 47

(2S)-1-{2-[(3S,1R)-3-(4-Cyanophenoxymethyl)cyclopentylamino]acetyl}-pyrrolidine-2-carbonitrile

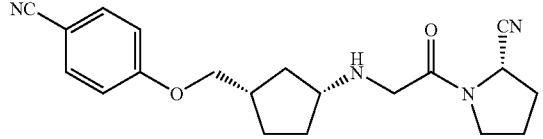

Step 1: N1-BOC-(3S,1R)-3-(4-cyanophenoxymethyl)cyclopentan-1-amine: This compound was prepared form Intermediate 7 (1.5 g, 6.97 mmol) and 4-cyanophenol (830 mg, 6.97 mmol) using diethyl azodicarboxylate (1.58 g, 9.06 mmol) and triphenylphosphine (2.1 g, 10.44 mmol) in dry THF (15 ml) as described in Example 43, Step 1 to give 1.53 g of the product as a white solid: IR (KBr) 3356, 2941, 2219, 1679, 1608, 1509, 1264, 1161 cm$^{-1}$; $^1$H NMR (CDCl$_3$, 300 MHz) δ 1.20–1.30 (m, 1H), 1.45 (s, 9H), 1.50–1.61 (m, 2H), 1.83–1.97 (m, 2H), 2.24–2.49 (m, 2H), 3.93 (d, J=6.5 Hz, 2H), 3.99 (brs, 1H), 4.75 (brs, 1H), 6.95 (dt, J=5.1, 2.7 Hz, 2H), 7.58 (dd, J=5.1, 2.4 Hz, 2H).

Step 2: (3S,1R)-3-(4-cyanophenoxymethyl)cyclopentan-1-amine: This compound was prepared from Step 1 intermediate (550 mg) as described in Example 1, Step 2 to give 400 mg of the amine as a semisolid, which was used as such for the next step.

Step 3: (2S)-1-{2-[(3S,1R)-3-(4-cyanophenoxymethyl)cyclopentylamino]acetyl}-pyrrolidine-2-carbonitrile: This compound was prepared from Step 2 intermediate (350 mg, 1.62 mmol) and Intermediate 18 (140 mg, 0.805 mmol) using $K_2CO_3$ (224 mg, 1.61 mmol) and NaI (243 mg, 1.62 mmol) in dry THF (30 ml) as described in Example 1, Step 3 to give 150 mg of the product as a semisolid; IR (neat) 3020, 2958, 2226, 1664, 1606, 1509, 1257, 1215 cm$^{-1}$; $^1$H NMR (CDCl$_3$, 300 MHz) δ 1.20–1.29 (m, 1H), 1.50–1.64 (m, 2H), 1.82–1.95 (m, 3H), 2.09–2.45 (m, 6H), 3.16–3.21 (m, 1H), 3.38 (s, 2H), 3.38–3.62 (m, 2H), 3.93 (d, J=6.9 Hz, 2H), 4.75–4.78 (m, rotamer, 1H), 6.93 (d, J=8.7 Hz, 2H), 7.57(dt, J=5.1, 2.7 Hz, 2H).

Example 48

(2S)-1-{2-[(3S,1R)-3-(4-Cyanophenoxymethyl)cyclopentylamino]acetyl}-pyrrolidine-2-carbonitrile hydrochloride

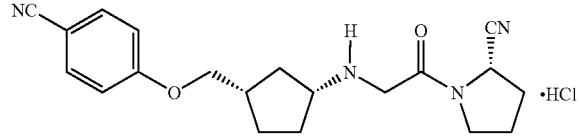

The hydrochloride salt of Example 47 (150 mg) was prepared as described in Example 4 using dry HCl gas in dichloromethane to give 155 mg of the product as a white solid: IR (KBr) 3900, 2956, 2223, 1670, 1605, 1508, 1258, 1172 cm$^{-1}$; $^1$H NMR (D$_2$O, 300 MHz) δ 1.47–1.54 (m, 1H), 1.60–1.69 (m, 1H), 1.76–1.93 (m, 2H), 2.07–2.52 (m, 7H), 3.39–3.72 (m, 3H), 3.97–4.10 (m, 4H), 4.65–4.68 (m, 1H), 7.04 (dd, J=4.8, 2.4 Hz, 2H), 7.66 (dd, J=5.1, 2.4 Hz, 2H).

Example 49

(2S)-1-{2-[(3S,1R)-3-(4-Cyano-3-fluorophenoxymethyl)cyclopentylamino]acetyl}-pyrrolidine-2-carbonitrile

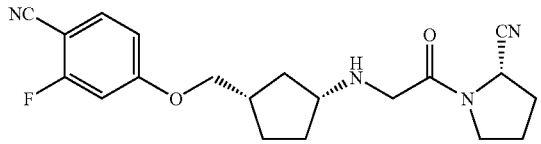

Step 1: N1-BOC-(3S,1R)-3-(4-cyano-3-fluorophenoxymethyl)cyclopentan-1-amine: This compound was prepared form Intermediate 7 (1.0 g, 4.65 mmol) and 4-cyano-3-fluorophenol (638 mg, 4.65 mmol) using diethyl azodicarboxylate (1.05 g, 6.02 mmol) and triphenylphosphine (1.83 g, 6.97 mmol) in dry THF (15 ml) as described in Example 43, Step 1 to give 1.2 g of the product as a white solid: IR (KBr) 3360, 2967, 2231, 1682, 1622, 1525, 1171 cm$^{-1}$; $^1$H NMR (CDCl$_3$, 300 MHz) δ 1.19–1.29 (m, 1H), 1.45 (s, 9H), 1.50–1.60 (m, 2H), 1.84–2.01 (m, 2H), 2.25–2.47 (m, 2H), 3.92 (d, J=5.7 Hz, 2H), 4.00 (brs, 1H), 4.72 (brs, 1H), 6.69–6.78 (m, 2H), 7.51 (dd, J=7.8, 1.2 Hz, 1H).

Step 2: (3S,1R)-3-(4-cyano-3-fluorophenoxymethyl)cyclopentan-1-amine: This compound was prepared from Step 1 intermediate (1.1 g) as described in Example 1, Step 2 to give 555 mg of the amine as a semisolid, which was used as such for the next step.

Step 3: (2S)-1-{2-[(3S,1R)-3-(4-cyano-3-fluorophenoxymethyl)cyclopentylamino]acetyl}-pyrrolidine-2-carbonitrile: This compound was prepared from Step 2 intermediate (500 mg, 2.13 mmol) and Intermediate 18 (184 mg, 1.06 mmol) using K$_2$CO$_3$ (294 mg, 2.13 mmol) and NaI (160 mg, 1.06 mmol) in dry THF (30 ml) as described in Example 1, Step 3 to give 100 mg of the product as a semisolid: IR (neat) 3318, 2952, 2228, 1661, 1621, 1506, 1415, 1301, 1172 cm$^{-1}$; $^1$H NMR (CDCl$_3$, 300 MHz) δ 1.19–1.28 (m, 2H), 1.53–1.60 (m, 2H), 1.82–1.89 (m, 2H), 2.11–2.45 (m, 6H), 3.16–3.22 (m, 1H), 3.39 (s, 2H), 3.42–3.62 (m, 2H), 3.93 (d, J=6.6 Hz, 2H), 4.60–4.78 (m, rotomer, 1H), 6.67–6.77 (m, 2H), 7.50 (t, J=7.8 Hz, 1H).

Example 50

(2S,4S)-1-{2-[(3S,1R)-3-(4-Cyano-3-fluorophenoxymethyl)cyclopentylamino]acetyl}-4-fluoro-pyrrolidine-2-carbonitrile

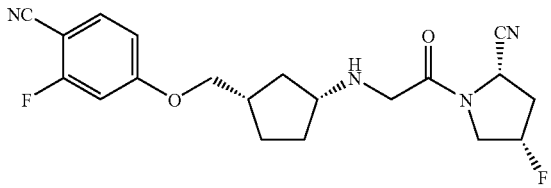

This compound was prepared from (3S,1R)-3-(4-cyano-3-fluorophenoxymethyl)-cyclopentan-1-amine (500 mg, 2.13 mmol) from Example 49, Step 2 and Intermediate 19 (203 mg, 1.06 mmol) using K$_2$CO$_3$ (294 mg, 2.13 mmol) and NaI (160 mg, 1.06 mmol) in dry THF (30 ml) as described in Example 1, Step 3 to give 100 mg of the product as a semisolid: IR (neat) 3328, 2937, 2227, 1659, 1618, 1500, 1416, 1301, 1113 cm$^{-1}$; $^1$H NMR (CDCl$_3$, 300 MHz) δ 1.19–1.28 (m, 1H), 1.44–1.63 (m, 2H), 1.82–1.89 (m, 3H), 2.11–2.48 (m, 3H), 2.64–2.78 (m, 1H), 3.17–3.23 (m, 1H), 3.39 (d, J=6.9 Hz, rotomer, 2H), 3.34–3.98 (m, rotomer, 2H), 3.93 (d, J=6.6 Hz, 2H), 4.96 (d, J=9.3 Hz, 1H), 5.32 (dt, J=5.1, 40.1 Hz, rotomer, 0.25H), 5.42 (dt, J=3.6, 44.1 Hz, rotomer, 0.75H), 6.70 (dd, J=8.4, 3.0 Hz, 1H), 6.75 (dd, J=6.0, 2.4 Hz, 1H), 7.50 (dd, J=7.8, 0.9 Hz, 1H).

Example 51

(2S)-1-{2-[(3S,1R)-3-(1-Cyanodibenzo[b,d]furan-4-yloxymethyl)cyclopentylamino]-acetyl}-pyrrolidine-2-carbonitrile

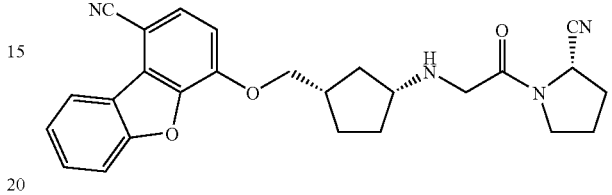

Step 1: N1-BOC-(3S,1R)-3-(1-cyanodibenzo[b,d]furan-4-yloxymethyl)cyclopentan-1-amine: This compound was prepared form Intermediate 7 (4.0 g, 19.13 mmol) and 4-hydroxydibenzo[b,d]furan-1-carbonitrile (4.11 g, 11.13 mmol) using diethyl azodicarboxylate (4.33 mg, 24.88 mmol) and triphenylphosphine (7.52 g, 28.70 mmol) in dry THF (80 ml) as described in Example 43, Step 1 to give 6.01 g of the product as a white solid: IR (KBr) 3356, 2965, 2221, 1684, 1509, 1258, 1105 cm$^{-1}$; $^1$H NMR (CDCl$_3$, 300 MHz) δ 1.44 (s, 9H), 1.48–1.67 (m, 2H), 1.77–2.07 (m, 3H), 2.35–2.57 (m, 2H), 2.06 (brs, 1H), 4.66 (d, J=5.7 Hz, 2H), 4.70 (brs, 1H), 7.41–7.46 (m, 1H), 7.59–7.62 (m, 2H), 8.19 (s, 1H), 8.96 (d, J=6.9 Hz, 1H), 10.17 (s, 1H).

Step 2: (3S,1R)-3-(1-cyanodibenzo[b,d]furan-4-yloxymethyl)cyclopentan-1-amine: This compound was prepared from Step 1 intermediate (1.0 g, 2.46) as described in Example 1, Step 2 to give 750 mg of the amine as a semisolid, which was used as such for the next step.

Step 3: (2S)-1-{2-[(3S,1R)-3-(1-cyanodibenzo[b,d]furan-4-yloxymethyl)cyclopentyl-amino]acetyl}-pyrrolidine-2-carbonitrile: This compound was prepared from Step 2 intermediate (750 mg, 2.44 mmol) and Intermediate 18 (212 mg, 1.23 mmol) using K$_2$CO$_3$ (337 mg, 2.44 mmol) and NaI (10 mg, 0.06 mmol) in dry THF (40 ml) as described in Example 1, Step 3 to give 210 mg of the product as a white solid: IR (neat) 3331, 2931, 2221, 1689, 1657, 1575, 1370, 1104 cm$^{-1}$; $^1$H NMR (CDCl$_3$, 300 MHz) δ 1.40–1.50 (m, 1H), 1.59–1.67 (m,1H), 1.77–1.82 (m, 1H), 1.88–2.33 (m, 9H), 2.54–2.59 (m, 1H), 3.22–3.27 (m, 1H), 3.44 (s, 2H), 3.57–3.63 (m, 1H), 4.67 (d, J=6.6 Hz, 2H), 4.75–4.78 (m, rotomer, 1H), 7.42–7.45 (m, 1H), 7.57–7.64 (m, 2H), 8.18 (s, 1H), 8.94 (d, J=8.1 Hz, 1H), 10.16 (s, 1H).

Protocol for In-Vitro DPP-IV Assay

DPPIV activity was determined by the cleavage rate of 7-amino-4-methyl coumarin (AMC) from synthetic substrate Glycyl-Prolyl-AMC. In brief, the assay was conducted by adding 10 ng of human recombinant Dipeptidyl peptidase IV enzyme (DPPIV, available commercially from R & D Systems) in 50 μl of the assay buffer (25 mM Tris, pH 7.4, 140 mM NaCl, 10 mM KCl, 1% BSA) to 96 well black flat bottom microtiter plates. The reaction was initiated by adding 50 μl of 100 μM substrate Gly-Pro-AMC. The incubation was carried out in the kinetic mode at 30° C. for 30 minutes. Fluorescence was measured using Fluorostar at excitation filter of 380 nm and emission filter of 460 nm).

Test compounds and solvent controls were added as 1 μl additions. A standard curve of free amino methyl coumarin (AMC) was generated using 0–100 μM AMC in the assay buffer. The curve generated, which was linear was used for the interpolation of catalytic activity.

Tests for $IC_{50}$ Studies:

Test compounds dissolved in DMSO at 5–6 concentrations were tested in duplicate along with the solvent control and blank samples. Percent inhibition was calculated at each concentration with respect to the solvent control sample (no test compound added). $IC_{50}$ values were calculated from 3 experiments using the prism software.

TABLE 1

DPP-IV inhibition using human recombinant DPP-IV enzyme (n = 3)

| COMPOUND | $IC_{50}$ (nM) |
|---|---|
| Example-1 | 6% at 300 nM |
| Example-2 | 17% at 300 nM |
| Example-3 | 6.29 |
| Example-4 | 10.03 |
| Example-5 | 10.34 |
| Example-7 | 11.71 |
| Example-8 | 10.55 |
| Example-9 | 6.27 |
| Example-10 | 7.81 |
| Example-11 | 13.88 |
| Example-12 | 11.25 |
| Example-13 | 12.11 |
| Example-14 | 3.58 |
| Example-15 | 3.17 |
| Example-16 | 2.76 |
| Example-17 | 2.93 |
| Example-18 | 9.80 |
| Example-19 | 20.04 |
| Example-20 | 41.29 |
| Example-21 | 6.74 |
| Example-22 | 10.42 |
| Example-23 | 14.58 |
| Example-24 | 6.29 |
| Example-25 | 8.59 |
| Example-26 | 5.16 |
| Example-27 | 17.45 |
| Example-28 | 22.26 |
| Example-29 | 10.00 |
| Example-30 | 63.44 |
| Example-31 | 91.80 |
| Example-32 | 36.99 |
| Example-33 | 57.29 |
| Example-34 | 26.10 |
| Example-35 | 70.87 |
| Example-36 | 10.57 |
| Example-37 | 65.99 |
| Example-38 | 9.42 |
| Example-39 | 11.10 |
| Example-40 | 78.65 |
| Example-41 | 15.84 |
| Example-42 | 26.81 |
| Example-43 | 35.94 |
| Example-44 | 25.79 |
| Example-45 | 49.92 |
| Example-46 | 11.63 |
| Example-47 | 13.76 |
| Example-48 | 13.51 |
| Example-49 | 23.52 |
| Example-50 | 2.56 |
| Example-51 | 25% at 300 nM |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

The invention claimed is:

1. A compound of general Formula (I)

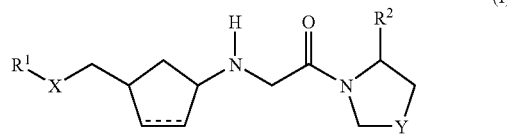

wherein:

Y is —$CH_2$—, CHF, or —$CF_2$;

X is $NR^3$, O or $S(O)_m$;

m is 0, 1 or 2;

the dotted line [----] in the carbocyclic ring represents an optional double bond;

$R^1$ is a substituted or unsubstituted 6-membered heteroaryl ring having at least one nitrogen atom or a substituted or unsubstituted 6-membered heterocyclic ring having at least one nitrogen atom;

$R^2$ is hydrogen, nitrile (—CN), COOH, $SO_3H$, $B(OH)_2$, $PO_3R^4R^5$, $SO_2NR^4R^5$, a tetrazole, an amide, an ester or an acid anhydride;

$R^3$ is hydrogen, hydroxy, acetyl, substituted or unsubstituted alkyl, and substituted or unsubstituted alkoxy; and $R^4$ and $R^5$ may be same or different and are independently hydrogen, nitro, hydroxy, cyano, formyl, acetyl, halogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroalkyl, or a tautomeric form, regioisomer, stereoisomer, enantiomer, diastereomer, solvate, N-oxide, or pharmaceutically acceptable salt thereof.

2. A compound according to claim 1 wherein one or more of $R^1$, $R^3$, $R^4$ and $R^5$ is independently substituted by one or more substituents wherein each substituent is independently hydrogen, hydroxy, halogen, carboxyl, cyano, amino, nitro, oxo (=O), thio (=S), optionally substituted alkyl, optionally substituted alkoxy, optionally substituted alkenyl, optionally substituted alkynyl, optionally substituted aryl, optionally substituted arylalkyl, optionally substituted cycloalkyl, optionally substituted aryl, optionally substituted heteroaryl, optionally substituted heteroarylalkyl, optionally substituted heterocyclic ring, —$COOR^x$, —$C(O)R^x$, —$C(S)R^x$, —$C(O)NR^xR^y$, —$C(O)ONR^xR^y$, —$NR^xCONR^yR^z$, —$N(R^x)SOR^y$, —$N(R^x)SO_2R^y$, —(=N—$N(R^x)R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$, —$OR^x$, —$OR^xC(O)NR^yR^z$, —$OR^xC(O)OR^y$—, —OC(O)

R$^x$, —OC(O)NR$^x$R$^y$, —R$^x$NR$^y$R$^z$, —R$^x$R$^y$R$^z$, —R$^x$CF$_3$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, —ONO$_2$, wherein R$^x$, R$^y$and R$^z$is independently hydrogen, substituted or unsubstituted alkyl, haloalkyl, substituted or unsubstituted arylalkyl, substituted or unsubstituted aryl, substituted or unsubstituted cycloalkyl, substituted or unsubstituted cycloalkylalkyl substituted or unsubstituted heterocyclic ring, substituted or unsubstituted heterocyclylalkyl, substituted or unsubstituted heteroaryl or substituted or unsubstituted heteroarylalkyl.

3. A compound according to claim 1, wherein X is —NR$^3$—wherein R$^3$ is hydrogen.

4. A compound according to claim 1, wherein X is O.

5. A compound according to claim 1, wherein X is —S(O)$_m$— and m is 0 or 2.

6. A compound according to claim 1, wherein Y is —CH$_2$—.

7. A compound according to claim 1, wherein Y is —CHF—.

8. A compound according to claim 1, wherein R$^1$is pyridin-2-yl.

9. A compound according to claim 1, wherein R$^1$is 5-cyanopyridin-2-yl.

10. A compound according to claim 1, wherein R$^1$ is Pyrimidin-2-yl.

11. A compound according to claim 1, wherein R$^2$ is hydrogen.

12. A compound according to claim 1, wherein R$^2$ is nitrile (—CN).

13. A pharmaceutical composition comprising, as an active ingredient, a compound according to claim 1 or a pharmaceutically acceptable salt thereof together with a pharmaceutically acceptable carrier or diluent.

14. A method for the treatment of diseases which are associated with DPP-IV, selected from the group consisting of Type II diabetes (non-insulin dependent diabetes mellitus), impaired glucose tolerance, inflammatory bowel disease, ulcerative colitis, Crohn's disease, and obesity, which method comprises administering to a patient suffering therefrom a therapeutically effective amount of a compound according to claim 1.

15. The method of claim 14, wherein the compound is administered in admixture with a pharmaceutically acceptable excipient, diluent, or carrier.

16. A method of treating insulin resistant non-impaired glucose tolerance in order to prevent or delay the onset of noninsulin-dependent diabetes mellitus comprising administering to a patient suffering therefrom a therapeutically effective amount of a compound according to claim 1.

17. A pharmaceutical composition comprising, as an active ingredient, a compound according to claim 1 or a pharmaceutically acceptable salt or prodrug or hydrate thereof together with a pharmaceutically acceptable carrier or diluent.

18. A compound selected from cis-(±)-6-(3-[2-(1-Pyrrolidinyl)-2-oxoethylamino]cyclopentylmethylamino)nicotinonitrile;
   6-((1SR,3RS)-3-{2-[(2S)-2-Cyanopyrrolidin-1-yl]-2-oxoethylamino}cyclopentyl-methylamino)nicotinonitrile;
   6-((1SR,3RS)-3-{2-[(2S)-2-Cyanopyrrolidin-1-yl]-2-oxoethylamino}cyclopentyl-methylamino)nicotinonitrile dihydrochioride;
   6-((1SR,3RS)-3-{2-[(2S)-2-Cyanopyrrolidin-1-yl]-2-oxoethylamino}cyclopentyl-methylamino)nicotinonitrile maleate;
   6-((1SR,3RS)-3-{2-[(2S)-2-Cyanopyrrolidin-1-yl]-2-oxoethylamino}cyclopentyl-methylamino)nicotinonitrile fumarate;
   6-((1SR,3RS)-3-{2-[(2S)-2-Cyanopyrrolidin-1-yl]-2-oxoethylamino}cyclopentyl-methylamino)nicotinonitrile citrate;
   6-((1S,3R)-3-{2-[(2S)-2-Cyanopyrrolidin-1-yl]-2-oxoethyl amino}cyclopentyl methylamino)nicotinonitrile;
   6-((1S,3R)-3-{2-[(2S)-2-Cyanopyrrolidin-1-yl]-2-oxoethylamino}cyclopentyl methylamino)nicotinonitrile dihydrochioride;
   6-((1R,3S)-3-{2-[(2S)-2-Cyanopyrrolidin-1-yl]-2-oxoethyl amino}cyclopentyl methyl-amino)nicotinonitrile;
   6-((1R,3S)-3-{2-[(2S)-2-Cyanopyrrolidin-1-yl]-2-oxoethyl amino}cyclopentyl methyl-amino)nicotinonitrile dihydrochioride;
   6-((4SR,1RS)-4-{2-[(2S)-2-cyanopyrrolidin-1-yl]-2-oxoethyl amino}-2-cyclopentenyl-methylamino)nicotinonitrile;
   6-((1RS,3RS)-3-{2-[(2S)-2-Cyanopyrrolidin-1-yl]-2-oxoethyl amino}cyclopentyl-methylamino)nicotinonitrile;
   6-((1SR,3RS)-3-{2-[(2S,4S)-2-Cyano-4-fluoropyrrolidin-1-yl]-2-oxoethylamino}cyclopentylmethylamino) nicotinonitrile;
   6-((1S,3R)-3-{2-[(2S, 4S)-2-Cyano-4-fluoropyrrolidin-1-yl]-2-oxoethylamino }cyclopentylmethylamino)nicotinonitrile;
   (2S)-1-{2-[(4S,1R)-4-(2-Pyridylsulfanylmethyl)cyclopent-2-ene amino]acetyl}-pyrrolidine-2carbonitrile;
   (2S)-1-{2-[(1S,3R)-3-(2-Pyridylsulfanylmethyl)cyclopentylamino]acetyl}-pyrrolidine-2carbonitrile;
   (2S)-1-{2-[(1S,3R)-3-(2-Pyridylsulfonylmethyl)cyclopentylamino]acetyl}-pyrrolidine-2-carbonitrile;
   6-((1SR,3RS)-3-{2-[(2S)-2-Cyanopyrrolidin-1-yl]-2-oxoethylamino}cyclopentyl-methylsulfanyl)nicotinonitrile;
   6-((1SR,3RS)-3-{2-[(2S)-2-Cyanopyrrolidin-1-yl]-2-oxoethylamino}cyclopentyl-methylsulfanyl)nictinonitrile maleate;
   6-((1SR,3RS)-3-{2-[(2S)-2-Cyanopyrrolidin-1-yl)-2-oxoethylamino}cyclopentyl-methylsulfonyl)nicotinonitrile;
   (2S)-1-{2-[(3S,1R)-3-(2-Pyrimidinylsulfanylmethyl)cyclopentylamino]acetyl}-pyrrolidine-2-carbonitrile;
   (2S)-1-{2-[(3SR,1RS)-3-(2-Pyrimidinylaminomethyl)cyclopentylamino)acetyl}-pyrrolidine-2-carbonitrile;
   (2S)-1-{2-[(3SR,1RS)-3-(2-Pyrimidinylaminomethyl)cyclopentylamino)acetyl}-pyrrolidine-2-carbonitrile dihydrochloride;
   (2S)-1-{2-[(3S,1R)-3-(2-Pyrimidinylaminomethyl)cyclopentylamino)acetyl}-pyrrolidine-2-carbonitrile;
   (2S)-1-{2-[(3R,1S)-3-(2-Pyrimidinylaminomethyl)cyclopentylamino]acetyl}-pyrrolidine-2-carbonitrile;
   or a pharmaceutically acceptable salt thereof.

19. A pharmaceutical composition comprising a compound according to claim 18 or a prodrug or hydrate thereof and a pharmaceutically acceptable carrier or diluent.

20. 6-((1SR,3RS)-3-{2-[(2S)-2-Cyanopyrrolidin-1-yl]-2-oxoethylamino}cyclopentyl-methylamino)nicotinonitrile or a pharmaceutically acceptable salt thereof.

21. 6-((1S,3R)-3-{2-[(2S)-2-Cyanopyrrolidin-1-yl]-2-oxoethylamino}methylamino)nicotinonitrile or a pharmaceutically acceptable salt thereof.

22. 6-((4SR,1RS)-4-{2-[(2S)-2-cyanopyrrolidin-1-yl]-2-oxoethylamino}cyclopentenyl-methylamino)nicotinonitrile or a pharmaceutically acceptable salt thereof.

23. 6-((1RS,3RS)-3-{2-[(2S)-2-Cyanopyrrolidin-1-yl]-2-oxoethylamino}cyclopentyl-methylamino)nicotinonitrile or a pharmaceutically acceptable salt thereof.

24. 6-((1S,3R)-3-{2-[(2S,4S)-2-Cyano-4-fluoropyrrolidin-1-yl]-2-oxoethylamino}cyclopentyl-methylamino)nicotinonitrile or a pharmaceutically acceptable salt thereof.

25. A pharmaceutical composition comprising a compound according to claim 20 and a pharmaceutically acceptable carrier or diluent.

26. A pharmaceutical composition comprising a compound according to claim 21 and a pharmaceutically acceptable carrier or diluent.

27. A pharmaceutical composition comprising a compound according to claim 22 and a pharmaceutically acceptable carrier or diluent.

28. A pharmaceutical composition comprising a compound according to claim 23 and a pharmaceutically acceptable carrier or diluent.

29. A pharmaceutical composition comprising a compound according to claim 24 and a pharmaceutically acceptable carrier or diluent.

* * * * *

UNITED STATES PATENT AND TRADEMARK OFFICE
CERTIFICATE OF CORRECTION

PATENT NO.         : 7,230,002 B2
APPLICATION NO.    : 11/050663
DATED              : June 12, 2007
INVENTOR(S)        : Abraham Thomas et al.

It is certified that error appears in the above-identified patent and that said Letters Patent is hereby corrected as shown below:

On the Cover Page: Item [63]

Delete "Provisional application No. 60/549,759, filed on July 29, 2004" and insert -- Provisional application No. 60/549,759, filed on March 2, 2004--

Signed and Sealed this

Seventh Day of August, 2007

JON W. DUDAS
*Director of the United States Patent and Trademark Office*